(12) United States Patent
Agrawal et al.

(10) Patent No.: US 9,913,476 B2
(45) Date of Patent: Mar. 13, 2018

(54) ANTIMICROBIAL ARTICLES OF MANUFACTURE PRODUCED FROM MASTERBATCHES

(71) Applicant: Agienic, Inc., Tucson, AZ (US)

(72) Inventors: Anoop Agrawal, Tucson, AZ (US); Donald R. Uhlmann, Tucson, AZ (US); Nicholas R. Krasnow, Tucson, AZ (US)

(73) Assignee: Agienic, Inc., Tucson, AZ (US)

( * ) Notice: Subject to any disclaimer, the term of this patent is extended or adjusted under 35 U.S.C. 154(b) by 0 days.

(21) Appl. No.: 14/948,022

(22) Filed: Nov. 20, 2015

(65) Prior Publication Data

US 2016/0135470 A1     May 19, 2016

Related U.S. Application Data

(63) Continuation of application No. 14/866,400, filed on Sep. 25, 2015, now abandoned, which is a continuation-in-part of application No. 14/089,146, filed on Nov. 25, 2013, now Pat. No. 9,155,310, and a continuation-in-part of application No. 13/480,367, filed on May 24, 2012, now abandoned, said application No. 14/089,146 is a continuation-in-part of application No. 13/685,379, filed on Nov. 26, 2012, now abandoned, which is a continuation-in-part of application No. 13/480,367, filed on May 24, 2012, now abandoned.

(60) Provisional application No. 61/800,122, filed on Mar. 15, 2013, provisional application No. 61/820,561, filed on May 7, 2013, provisional application No. 61/881,318, filed on Sep. 23, 2013, provisional application No. 61/519,523, filed on May 24, 2011, provisional application No. 61/582,322, filed on Dec. 31, 2011.

(51) Int. Cl.

| | |
|---|---|
| *A01N 59/20* | (2006.01) |
| *A61K 8/19* | (2006.01) |
| *A61K 33/34* | (2006.01) |
| *A61K 8/02* | (2006.01) |
| *A61K 9/14* | (2006.01) |
| *A61Q 17/00* | (2006.01) |
| *C09K 8/80* | (2006.01) |
| *A01N 25/12* | (2006.01) |
| *A61K 8/25* | (2006.01) |
| *A61Q 3/02* | (2006.01) |
| *A61K 9/00* | (2006.01) |
| *A61K 9/06* | (2006.01) |
| *A61K 47/32* | (2006.01) |
| *A61K 9/08* | (2006.01) |
| *A61K 8/20* | (2006.01) |
| *C09D 5/14* | (2006.01) |
| *A61K 6/00* | (2006.01) |
| *C09K 8/60* | (2006.01) |
| *A61K 8/81* | (2006.01) |
| *A61K 31/555* | (2006.01) |
| *A61K 33/38* | (2006.01) |
| *C09D 5/16* | (2006.01) |

(52) U.S. Cl.
CPC ............ *A01N 59/20* (2013.01); *A01N 25/12* (2013.01); *A61K 6/0017* (2013.01); *A61K 8/0279* (2013.01); *A61K 8/19* (2013.01); *A61K 8/20* (2013.01); *A61K 8/25* (2013.01); *A61K 8/8176* (2013.01); *A61K 9/0014* (2013.01); *A61K 9/06* (2013.01); *A61K 9/08* (2013.01); *A61K 31/555* (2013.01); *A61K 33/34* (2013.01); *A61K 33/38* (2013.01); *A61K 47/32* (2013.01); *A61Q 3/02* (2013.01); *A61Q 17/005* (2013.01); *C09D 5/14* (2013.01); *C09D 5/1618* (2013.01); *C09K 8/605* (2013.01); *C09K 8/805* (2013.01); *A61K 2800/412* (2013.01)

(58) Field of Classification Search
None
See application file for complete search history.

(56) References Cited

U.S. PATENT DOCUMENTS

| | | | | |
|---|---|---|---|---|
| 4,729,862 A | * | 3/1988 | Salatiello | B29C 41/003 264/310 |
| 2006/0199900 A1 | * | 9/2006 | Matsumoto | B82Y 30/00 524/556 |
| 2008/0193496 A1 | * | 8/2008 | Gabbay | A01N 59/20 424/404 |
| 2009/0057621 A1 | * | 3/2009 | Keulen | C08J 3/226 252/500 |
| 2009/0281210 A1 | * | 11/2009 | Aramaki | C08J 3/226 523/351 |

(Continued)

FOREIGN PATENT DOCUMENTS

| | | | | |
|---|---|---|---|---|
| CA | 2735793 A1 | * | 3/2010 | ............... A61K 9/10 |
| JP | 2006096802 A | * | 4/2006 | |

*Primary Examiner* — Tracy Vivlemore
*Assistant Examiner* — Monica A Shin
(74) *Attorney, Agent, or Firm* — Rothwell, Figg, Ernst & Manbeck, P.C.

(57) ABSTRACT

The invention relates to use of masterbatches containing high concentrations of antimicrobial materials such as copper salts, particularly copper iodide. These masterbatch compositions are added to other materials which are used to form various articles of manufacture with antimicrobial properties. The copper salts may be incorporated in the masterbatches as surface functionalized particles or the salts may be incorporated into porous particles prior to the formation of masterbatches.

6 Claims, 4 Drawing Sheets

(56) References Cited

U.S. PATENT DOCUMENTS

2011/0272641 A1* 11/2011 Bastiaens ............... B82Y 30/00
252/511

* cited by examiner

ANTIMICROBIAL ARTICLES OF MANUFACTURE PRODUCED FROM MASTERBATCHES

CROSS REFERENCE TO RELATED APPLICATIONS

This application is a continuation of co-pending U.S. application Ser. No. 14/866,400, filed on Sep. 25, 2015, which is a continuation in part of U.S. application Ser. No. 14/089,146 (now U.S. Pat. No. 9,155,310), filed Nov. 25, 2013 and issued Oct. 13, 2015, which (1) claims the benefit of US provisional applications 61/800,122 (filed Mar. 15, 2013, 61/820,561 (filed May 7, 2013) and 61/881,318 (filed Sep. 23, 2013), (2) is a continuation-in-part of U.S. application Ser. No. 13/480,367, filed May 24, 2012 (now abandoned), which application in turn claims priority to U.S. Provisional Patent Application Ser. No. 61/519,523 filed May 24, 2011, U.S. Provisional Patent Application Ser. No. 61/582,322 filed Dec. 31, 2011; and (3) is a continuation-in-part of U.S. application Ser. No. 13/685,379 filed on Nov. 26, 2012 (now abandoned) which is a continuation in part of U.S. application Ser. No. 13/480,367 filed on May 24, 2012 (now abandoned). The contents of all of the foregoing applications are incorporated herein by reference entirely.

FIELD OF THE INVENTION

The invention relates to use of masterbatches, concentrates and/or intermediates containing copper iodide and the use of such masterbatches, concentrates and/or intermediates to prepare articles of manufacture.

BACKGROUND OF THE INVENTION

The antimicrobial effect of various metals and their salts has been known for centuries. Its germicidal effects increased its value in utensils and as jewelry. The exact process of silver's germicidal effect is still not entirely understood, although theories exist. One of these is the "oligodynamic effect," which qualitatively explains the effect on some microorganisms, but cannot explain antiviral effects. Silver is widely used in topical gels and impregnated into bandages because of its wide-spectrum antimicrobial activity.

The oligodynamic effect is demonstrated by other metals, specifically gold, silver, copper, zinc, and bismuth. Copper is one such metal. Copper has long been used as a biostatic surface to line the bottoms of ships to protect against barnacles and mussels. It was originally used in pure form, but has since been superseded by brass and other alloys due to their lower cost and higher durability. Bacteria will not grow on a copper surface because it is biostatic. Copper alloys have become important netting materials in the aquaculture industry for the fact that they are antimicrobial and prevent biofouling and have strong structural and corrosion-resistant properties in marine environments. Organic compounds of copper are useful for preventing fouling of ships' hulls. Copper alloy touch surfaces have recently been investigated as antimicrobial surfaces in hospitals for decreasing transmission of nosocomial infections.

Numerous scientific investigations have focused on the role of the metal form of copper, and have concluded that multiple mechanisms may be possible for copper's antimicrobial effect, including increased production of reactive oxidation species such as singlet oxygen and hydroxide radicals, covalent binding of copper metal to reactive sites in enzymes and co-factors, interference with lipid bilayer transport proteins, and interaction of copper ions with moieties of microorganisms analogous to what have been proposed for silver ions.

SUMMARY OF THE INVENTION

The inventors associated with this patent have made the surprising discovery that antimicrobial compositions comprising particles comprising certain low water solubility copper salts have much greater efficacy against a broad range of aerobic and anaerobic microbes, including bacteria, viruses, molds and fungi, than similar silver-based antimicrobial particles. In particular, it has been discovered that particles of copper salts including the copper halide and specifically copper iodide ("CuI"), when formulated in accordance with the teachings herein, is surprisingly effective as a broad-spectrum, fast-acting antimicrobial agent. The particles of these salts are surface functionalized.

In a further embodiment, high water solubility salts may be added to the compositions comprising the inventive particles. In a particularly preferred embodiment, the high water solubility salts comprise at least one halide salt with a room temperature water solubility of greater than 1 g/liter.

In yet another embodiment, organic acids, salts of organic acids, and esters of organic acids may be used as functionalization agents for the particles or as additives to the antimicrobial compositions.

In yet another embodiment, the antimicrobial compositions of this invention may be used to manufacture solid or liquid products with antimicrobial properties.

In a further embodiment, the functionalization agents preferably have a molecular weight of at least 60.

In yet another embodiment, the antimicrobial compositions are used in the petroleum extraction industry, personal care products and wound management.

Another embodiment of the present invention is the use of the above antimicrobial compositions is to kill anaerobic as well as aerobic bacteria.

In yet another surprising discovery, the preparation of the inventive particles using wet grinding processes enhances their economic viability and provides several other benefits. Such processes may be used to produce functionalized particles of other low water solubility salts and compounds such as silver halides.

In a further embodiment, one may deposit the copper salts of low water solubility or silver halides in porous particles, wherein such porous particles are used as additives to various carriers (liquids or solids) or products to impart antimicrobial properties to these.

These and other features of the present invention will become apparent from the following detailed description and the accompanying drawings

DETAILED DESCRIPTION OF EMBODIMENTS OF THE INVENTION

1. Introduction

Figure 1:
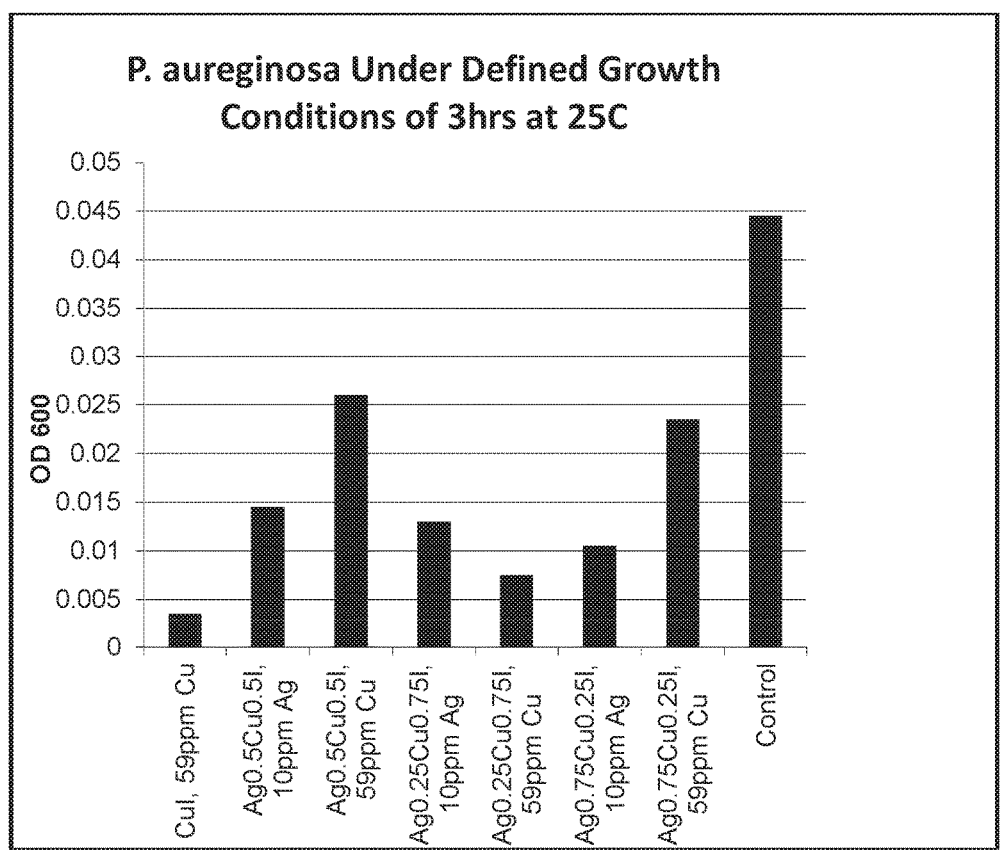
FIG. 1 is a plot of Optical Density (OD, Y-axis) against *P. aeruginosa* growth and/or inhibition by copper iodide particles and Ag—CuI mixed metal halides, and a control.

The present invention is concerned broadly with compositions and particles of oligodynamic metals and their compounds, and with combinations of such compositions and particles with other known antimicrobials. These compositions may be added to articles of manufacture which result in antimicrobial products. These products include liquids and solids, wherein the solids include coatings. The inventors associated with this patent have made the surprising discovery that particles made of certain metal salts have much greater efficacy against a broad range of bacteria, viruses, molds and fungi than known silver-only based antimicrobial particles. In particular, it has been discovered that the copper halide salt, copper iodide ("CuI"), when formulated in accordance with the teachings herein, is surprisingly effective as a broad-spectrum, fast-acting antimicrobial agent. Therefore, a first embodiment of the invention is directed to a composition having antimicrobial activity comprising a particle comprising at least one inorganic copper salt, the particle preferably having an average size of less than about 1000 nm; and at least one functionalizing agent in contact with the particle, the functionalizing agent stabilizing the particles in a carrier such that an antimicrobially effective amount of ions are released into the environs of the microbe.

2. The Compositions and Processing a. Oligodynamic Metals

In one embodiment of the invention, the preferred material compositions comprise at least one metal halide and the combination of one or more metals with at least one metal halide. Preferred metals are copper, zinc, silver and their alloys, and preferred metal halides are copper halides, and silver halides, especially copper iodide, copper (1) chloride, silver iodide, silver bromide and silver chloride. Example of these alloys are those of silver+copper, copper+tin (bronze) and copper+zinc (brass is an alloy of copper and zinc with typical copper concentrations in the range of 40 to 90% by weight, and may have additional elements, e.g., as in phosphor bronze). These alloys may provide better stability of particles in the processing or in end use applications against oxidation or non-desirable surface reactions. In most cases, the material compositions of this invention are preferably added into articles or products as preformed particles. That is, the surface functionalized salt particles are formed before they are added to the end-product or the formulation used to make the end-product. Similarly, porous particles with antimicrobial materials deposited into the pores are preformed prior to their incorporation in the end-product or the formulation used to make the end-product. The functionalized salt particles or the porous particles may undergo additional chemical or physical reactions once they are added to the end-product or the formulation used to make the end-product.

b. Copper Salts

The copper salt embodiments of the present invention include copper salts, both inorganic and organic copper salts. By way of exemplification the following copper compounds are illustrative but not limiting: Copper(II) iodate; Copper(I) iodide; Copper(I) chloride; Copper(I) bromide; Copper(I) oxide; Copper(I) acetate; Copper(I) sulfide; and Copper(I) thiocyanate.

The copper salts may have a range of water solubility characteristics. However, it is preferred that the copper salts of the present invention have low water solubility so that they may have slow and predictable copper cation release characteristics. In some formulations it may be desirable to also add Cu(II) or more soluble salts so that some fraction of Cu ions are quickly available. Cu(I) cations have shown the most efficacy against the various microbes tested. At room temperature, copper salt solubilities of less than about 100 mg/liter are preferred, and more preferred are copper salts having water solubilities less than about 15 mg/liter. In many applications lower water solubility is important, particularly where antimicrobial products come in contact with body fluids and water and long term efficacy is required. In some cases metal salts with high water solubility are added as additional antimicrobial agents so as to release a high concentration of ions over a short period of time. In addition, the human body also regulates the concentrations of several elements (labeled as micronutrients). Interestingly both elements of copper iodide, i.e., copper and iodine, belong to this class of elements. On the one hand, the low solubility of copper iodide allows one to make products with high efficacy where such efficacy is retained for a long time, and further, due to body regulative functions it is also not toxic at the levels at which it is an effective antimicrobial agent.

Other embodiments of copper (I) salts that may be useful in the present invention include halides where some of the copper has been substituted with other cations which may be other metals (forming mixed halide materials), or a given halide may be substituted with other anions. Alternatively, the substitution may be organic in nature, examples of such substitutions include e.g., $AgCuI_2$, $CH_3NCuI_2$, $Rb_3Cu_7Cl_{10}$, $RbCu_3Cl_4$, $CsCu_9I_{10}$, $CsCu_9Br_{10}$, $Rb_4Cu_{16}I_7Cl_{13}$ and $RbCu_4Cl_3I_2$. In general one may express these mixed halide copper salts as $P_sCu_rX_{(s+t)}$, where P is the organic or a metal cation and X is a halide, preferably selected from one or more of Cl, Br and I. An alternative way to express these compositions is $P_sCu_rX$ when $t=1-s$.

c. Copper Halides

Halide salts are particularly preferred, since in addition to the copper ions, these salts also contain anions which have antimicrobial affects. For example, chlorine, bromine and iodine ions are used as antimicrobial agents in several cleaning and medical applications. Copper iodide (CuI), like most "binary" (containing only two elements) metal halides, is an inorganic material and forms a zinc blende crystal lattice structure. It can be formed from a simple substitution reaction in water with copper acetate and sodium or potassium iodide. The product, CuI, simply precipitates out of solution since it is sparingly soluble (0.020 mg/100 mL at 20° C.) in water. Copper iodide powder can be purchased in bulk from numerous vendors. For medicinal or human applications, grade with over 98% purity is particularly preferred.

Copper bromide (CuBr) is also an inorganic material having the same crystal structure as CuI. It is commonly prepared by the reduction of cupric salts with sulfite in the presence of bromideCuBr is also sparingly soluble in water but has a solubility greater than that of CuI. Further, as discussed below for many applications, on the basis of coloration, CuBr is less preferred as its powder has a lower L* value.

Copper chloride shares the same crystal structure with CuBr and CuI and has a solubility of 62 mg/100 mL.

Copper(I) fluoride disproportionates immediately into Cu(II) fluoride unless it is stabilized by complexation, so CuF is not a very useful copper halide particle source. Cu(II)

fluoride is soluble in water and so it is not a source of Cu(I) cations, but is a source of Cu(II) cations.

For many (but not all) applications, the appearance and color of the coatings or the bulk products is important. For these applications the antimicrobial material should not change the appearance significantly. Some examples of these are paints and varnishes for buildings, fixtures and furniture, coatings for cosmetics use, incorporation in molded articles, and coatings and bulk incorporation in fibers for textiles, carpets, gaskets, etc. Thus it is preferred that the additives are colorless or pale in color and do not change the coloration of the product significantly after they are added. For many applications the coloration of these materials may be assessed by looking at the color of bulk powders. In general for applications where appearance is important, the color of the bulk powder should preferably meet certain requirements as discussed in the next section relating to the $L^*a^*b^*$ color coordinates.

d. Non-Copper Salts

In addition to being antimicrobial, preferred metal salts have low water solubility (less than 100 mg/liter or more preferably less than 15 mg/liter at 25° C.). When low water solubility antimicrobial materials are added to coatings or bulk materials, they provide an efficacy that lasts for long periods. The materials of the present invention may be combined with other antimicrobials in a product. These other antimicrobials may include salts with greater water solubility and even water-soluble salts in cases where one wants to provide a quick as well as a sustained antimicrobial efficacy, or if they perform some other function in the formulation.

Besides low water solubility, there are also other desirable attributes of the materials which may be important for specific applications. These include the colorless or weakly colored materials, stability in atmosphere, and stability to temperature for both processing and in use. Table 1 shows water solubility of a few select metal halides and other salts.

TABLE 1

Water solubility of selected metal salts at room temperature

| Material | Water solubility (mg/L) |
| --- | --- |
| AgI | 2.2E−03 |
| AgBr | 1.4E−01 |
| AgCl | 1.9E+00 |
| CuBr | 1.1E+01 |
| CuI | 2.2E−01 |
| $CuCl_2$ | 7.0E+05 |
| CuCl | 6.2E+01 |
| CuSCN | 8.4E−03 |
| $ZnI_2$ | 4.5E+06 |
| $ZnBr_2$ | 4.5E+06 |
| $ZnCl_2$ | 4.3E+06 |
| $BiI_3$ | 7.8E+00 |

Table 2 shows the color coordinates of various copper, silver and some other halides. The color coordinates of various powders were measured on the Colorimeter model UltraScan XE (from Hunterlab, Reston, Va.) in RSIN reflectance mode using the small, 0.375 inch aperture. A glass slide was covered with a piece of double sided tape and a small amount of the powder as received from Sigma Aldrich was placed on the double sided tape to give a smooth, solid dry powder finish. To protect the powder from disengaging into the colorimeter while the measurements were being performed, a second slide (top slide) was then placed over the top of the first and the two slides were taped together. The double slide was then read for $L^*a^*b^*$ coordinates on the colorimeter with the top slide facing the reflectance port.

The colors measured here are not absolute values for a given material, as the color also depends on the level of purity and the type of impurity present in these materials. An $L^*$ value of 100 (maximum) indicates a completely white color and a value of 0 indicates a completely black color. For a low degree of color, the color of the bulk powder should preferably have a $L^*$ value greater than 65, and more preferably greater than 70, and most preferably greater than 80 when measured on a color scale of $L^*a^*b^*$. The desirable values of $a^*$ and $b^*$ are dependent on $L^*$ value, and should be as close to zero as possible. As a rough guideline, when $L^*$ value is at 65, the $a^*$ and the $b^*$ values are preferably within ±5, when $L^*$ value is at 70, the $a^*$ and the $b^*$ values are preferably within ±15, when $L^*$ value is at 75, the $a^*$ and the $b^*$ values are preferably within ±20, and when $L^*$ value is at 80 or greater, the $a^*$ and the $b^*$ values are preferably within ±25 as long as these values are within the $L^*a^*b^*$ color sphere. Color may also be measured for functionalized particles in dry powdered state, and it is also preferred that such powders exhibit low coloration along the above established guidelines.

TABLE 2

Color coordinates of as received powders

| Material | Source, Catalogue number | $L^*$ | $a^*$ | $b^*$ |
| --- | --- | --- | --- | --- |
| BISMUTH (III) IODIDE | Sigma Aldrich, 341010 | 0.01 | 0.09 | 0.02 |
| GOLD (I) IODIDE | Sigma Aldrich, 398411 | 76.6 | −1.98 | 34.55 |
| SILVER BROMIDE | Sigma Aldrich, 226815 | 45.02 | −20.55 | 42.49 |
| SILVER IODIDE | Sigma Aldrich, 204404 | 78.05 | −7.13 | 20.28 |
| SILVER CHLORIDE | Sigma Aldrich, 227927 | 72.46 | 4.01 | 5.05 |
| COPPER (I) BROMIDE | Sigma Aldrich, 254185 | 42.02 | −29.36 | −3.45 |
| COPPER (I) IODIDE | Sigma Aldrich, 205540 | 72 | 2.54 | 10.85 |
| COPPER (I) CHLORIDE | Sigma Aldrich, 229628 | 76.35 | −4.46 | 14.93 |
| COPPER (I) THIOCYANATE | Sigma Aldrich, 298212 | 76.17 | 0.46 | 8.79 |

These indicated color characteristics are required so that the appearance of the product incorporating the functionalized antimicrobial particles (e.g., coatings molded products, fibers) is not compromised. Color is less important for those applications where appearance is not an issue or where the articles already have a strong color.

Temperature stability is dependent on the processing temperature used to produce the product and the temperature seen during the use. Since antimicrobial materials have to go through a long regulatory process, it is difficult to change composition for each application; thus it is desirable that a given composition can be used over a broad range of conditions. Since most molding operations for polymers, including powder coating operations, are carried out at temperatures ranging from about 150 to about 250° C., it is preferable for the compositions to be stable to 150° C. or higher. Since the melting points of nanoparticles in a size smaller than 50-100 nm may be significantly lower than those of bulk materials, the melting point must be notably higher than the expected use temperatures when particles smaller than 50-100 nm are used. The preferred non-copper salts of oligodynamic metals are those of silver. Of these the more preferred salts are silver halides, and in particular AgCl, AgBr and AgI. Of these AgCl and AgI are more preferred due to lower degree of coloration (higher L* value), particularly for those applications where color of the product is important.

Further, the preferred silver halides also have a drawback in that the materials tend to exhibit coloration to light such as the sun. Hence for those products where exposure to light such as sunlight is anticipated, these halides may desirably be doped with other materials so as to reduce the darkening. One way of accomplishing this is to make compounds such as mixed metal halides (or doping one metal halide with another metal halide) to reduce discoloration but still preserve low color, low water solubility and other desirable attributes. Another approach involves silver halide particles with mixed anions. Additional aspects of mixed metal halides are also discussed in the section below. Yet another approach is to make compostions when functionalization agents are materials with strong UV absorption, or even visible radiation (as long as it does not impair the product characteristics) so that they absorb a significant amount of radiation to reduce the impact of radiation on the metal halides.

It should be noted that while some of the copper halides may also exhibit mild discoloration on exposure to light such as sunlight, the extent of such discoloration is markedly less than that of the silver halides, and any such discoloration which can also be reduced by doping.

In addition, attractive economics of the material are also very important for a variety of applications. The cost of copper compounds, such as the preferred copper halides of the present invention, is notably smaller than that of silver compounds. When the functionalized antimicrobial materials of the present invention comprise silver constituents, it is preferred to minimize the extent of such additions of silver constituents consistent with achieving the desired antimicrobial efficacy and other desirable attributes.

Other metal iodides may also be used, in conjunction with the materials of this invention, but many of the metal halides have drawbacks which limit that usefulness in many applications as primary antimicrobial agents. A few select iodides with their principal shortcomings are; germanium (II) iodide (decomposes at 240° C.); germanium(IV) iodide (melting point is 144° C.); tin(II) iodide (is bright red in color); tin(IV) iodide (red in color and hydrolyses in water); platinum(II)iodide (black in color); bismuth(III) iodide (black in color); gold(I) iodide (unstable, decomposes on treating with hot water); iron(II) iodide (black colored and water soluble); cobalt(II) iodide (black colored and water soluble); nickel (II) iodide (black colored and water soluble); zinc(II) iodide (white colored but water soluble); and indium(III) iodide (orange colored). As seen, these iodides are deeply colored, or have low melting point or poor thermal stability, poor stability when exposed to oxygen or moisture, or high water solubility. These or other metal iodides may, however, be used to mix or dope the desirable copper or silver halides as long as the desirable properties of these materials are not compromised.

e. Mixed-Metal Halides

Further embodiments of the invention are directed to mixed-metal halides. These are novel halide salts containing more than a single cation, or containing more than a single anion or containing more than a single cation and more than a single anion. In the mixed-metal halides of the present invention, at least one of the cations is an oligodynamic metal cation, preferably a copper cation. More preferably, all of the mixed-metal cations are oligodynamic metal cations. Embodiments include silver-copper halide, gold-copper halide, silver-gold halide, etc. For example a metal halide of two metals with a common anion may be expressed as $M_1$-$M_2$(X), where $M_1$ is the first metal, $M_2$ is the second metal and X is the halide anion. Another combination is $M_1$-$M_2$($X_1$—$X_2$), where $X_1$ and $X_2$ are different halogen anions. Most preferred embodiments include silver-copper halides. Embodiments may include halogens such as iodide, bromide and chloride. A preferred embodiment is Iodide. Some exemplary embodiments are (Cu—Ag)I, (Cu—Ag)Cl, (Cu—Ag)(Br—I), (Cu—Ag)(I—Cl), Ag(Cl—I) and Cu(Cl—I). Please note that the stoichiometric proportion in the mixed metal halides between the various anion and the cations may be any which can be formed and is suitable for the application. In one embodiment, the particles preferably have more than 21% by weight of copper salts with a solubility of less than 100 mg/liter; more preferably the particles should have more than 51% by weight of such copper salts and most preferably these salts should be about more than 71% by weight.

f. Mixtures of Particles

In other embodiments of the present invention, the functionalized particles comprise mixtures or combinations of functionalized particles of different compositions wherein at least one component are functionalized particles of a salt of oligodynamic metals. In a specific embodiment, compositions comprising copper halide particles especially copper iodide may be combined with silver halides particles, e.g., silver bromide. In a further embodiment, these compositions, particularly compositions comprising copper halides especially copper iodide may be combined with other known antimicrobial or antifungal agents. One may also combine particles of different sizes/composition/solubilities to control the delivery rate and the longevity of the antimicrobial efficacy of the products in which where such particles are incorporated. As an example, one may combine particles about 300 nm in size with those that are less than 30 nm, or one may combine particles larger than 300 nm in size with those that are smaller than 300 nm, etc.

In applications such as those where copper or other compounds are used for antimicrobial effects, one may combine those materials with materials of the present invention. As a specific example, in marine coatings where zinc pyrithione, cuprous oxide or copper thiocyanate are used for their antimicrobial properties, one may prepare these compounds as functionalized particles with sizes smaller than about 300 nm. As another specific example, these materials may be combined with copper iodide as taught in the present invention. As another specific example, one may also use other antimicrobial compounds which are relatively water soluble in conjunction with the materials of the present invention. In such cases, the more water soluble component will result in a fast release of antimicrobial ions when such products are brought in contact with moisture. Some examples are, silver nitrate, copper (II) chloride, zinc chloride, potassium iodide, sodium iodide and zinc iodide.

Embodiments of the mixture of particles are directed to a composition having antimicrobial activity comprising (a) a mixture of particles comprising particles of a copper salt and particles of at least a second inorganic metal compound or metal; and (b) at least one functionalizing agent in contact with at least one of these particles. A further embodiment of the copper salt comprises a copper halide salt, and a still further embodiment of the copper salt comprises copper iodide. One of the preferred materials for use as second metal is silver and the preferred compounds are silver halides.

For many applications cost is an important issue. Addition of precious metals or their salts to the compositions of this invention can make antimicrobial materials less attractive economically. Since the copper salts of the present invention have shown high efficacy against a variety of microbes and are less costly than the silver halides, for many applications mixing copper halides with silver, gold, platinum or other precious metals and their salts is not necessary. If needed for specific applications, the precious metals and their salts may be utilized in much lower concentrations than if they were not combined with the copper salts.

g. Functionalizing Agents

An important embodiment of the present invention is the functionalization of the metal salt particles. In functionalizing the surfaces of the particles of oligodynamic metals and their compounds or salts, a number of chemical species may effectively be used, which may be selected from one or more of the categories below. These functionalizing agents are preferably present while the particles or new surfaces are being formed, either during chemical synthesis, or during physical grinding when they are being ground to a finer size from larger particles. The amount of surface functionalizing agent increases with decreasing particle size in proportion to the overall change in surface area exposed for functionalizing. Any ratio of the relative amounts of the metal salt particles and the functionalizing material may be used, typically these are present in a weight or a molar ratio (metal salt:functionalizing agent) in a range of about 100:1 to about 1:100 and more preferably a range of about 20:1 to 1:20. For polymeric functionalization agents, the molarity is calculated based on average molecular weight of a repeat unit in a polymer chain rather than the molecular weight of the entire polymeric chain. For a specific metal salt and functionalization agent either weight ratio or molar ratio may be used whichever ratio results in larger range. When the organic functionalizing agents are employed, their molecular weight should preferably be greater than 60. One purpose of the functionalizing agents is to reduce the interparticle interaction so that they disperse more easily. Putting higher molecular weight functionalization agents helps to weaken this interaction between the particles and helps dispersion.

Surface functionalization typically imparts one or more of many attributes, such as preventing particles from agglomeration (e.g., promoting suspension stability, particularly in liquid products and in liquid coating formulations), enabling particles to attach to various surfaces of an object or even to the microbes or the interior of the microbes, assisting antimicrobial materials to penetrate the membrane of the microbes and assisting particles to attach to matrix materials when these are incorporated as composites into other materials. This functionalization also helps to disperse the antimicrobial particles easily into these matrices (e.g., blending with thermoset or thermoplastic polymers which are later molded into objects). The functionalization may also assist in transporting these particles and/or the ions generated from them through the microbe outer layers, or through the matrices they are incorporated into. The functionalization may also assist in keeping the physical and chemical properties of the product in which the particles are incorporated from changing in a way that is undesirable.

Several functionalization agents are taught in this section, and many more are taught later in various sections including applications section. It must be understood that any of the functionalization agent listed in this invention may be used for any antimicrobial application and must not be limited by specific examples in which they are discussed.

Use of acids along with other surface functionalization agents or other functionalization agents with mildly reducing properties are desirable when Cu(I) halides (e.g., CuI, CuBr, CuCl) are used as antimicrobial materials. In the presence of or in association with these materials $Cu^+$ ions are prevented from oxidizing to $Cu^{++}$ ions. This is desirable because $Cu^+$ have superior antimicrobial properties. Examples of acids include mineral acids (e.g., hydrochloric acid, nitric acid, sulfuric acid), or organic acids (such as acetic acid, ascorbic acid, citric acid, glutamic acid, sorbic acid, erythorbic acid, thiodipropionic acid, sulfamic acid, adipic acid, gallic acid, alginic acid, caprylic acid, linoleic acid, cinammic acid and alkylbenzene sulfonic acids such as dodecyl benzene sulfonic acid). Examples of reducing agents include alcohols, polyols and aldehydes of the organic materials listed above, and some specific examples also include sugars, glucose, xylitol, sorbose, cinnamonaldehyde, etc.

Salts of many of the above acids (particularly containing cations of lithium, sodium potassium, calcium, zinc and copper) and esters of organic salts of the above acids may also be used and may be combined with additional functionalization agents. Some examples of alkali salts of the above salts are mono, di and tri-sodium citrates, sodium ascorbate, sodium sorbate, sodium iodide, sodium cinnamonate, etc. In addition to sodium some of the other preferred alkali ions are lithium and potassium. Similarly one may use salts of the other mentioned cations. Some other examples of preferred salts are copper citrate, halides of lithium, sodium and potassium, sodium palmitate, sodium oleate, sodium formate, calcium diacetate, sodium gluconate, sodium carboxy methyl cellulose, sodium caseinate, zinc gluconate and zinc stearate. These salts stabilize the $Cu^+$ ions and act as buffers to maintain the pH in a desired range. Some examples of esters of the organic acids are lauryl gallate and ascorbic acid palmitate. Lauryl gallate and ascorbic acid palmitate have low water solubility, and thus may be more suitable for non-aqueous formulations. One has to be careful in using excess acids as they may themselves act as antimicrobial agents, and may also reduce $Cu^+$ to $Cu^o$ which may impart undesirable color or even cause precipitation. These salts or alcohols, polyols and aldehydes of the organic materials listed above may be used as additives to the antimicrobial compositions, wherein the same or different materials may be used as functionalization agents.

Incorporation of soluble salts in the compositions of this invention may impart additional attributes. Some examples of soluble salts include halides and non-halides. As another example, when copper or silver iodide is used, the use of lithium iodide, sodium iodide and potassium iodide along with poly vinyl pyrrolidone and its copolymers promote dispersability, and it is likely that some of these salts form a complex with the polymer to produce a composite which is a more efficient surface functionalization agent.

Further, one may also incorporate materials in their elemental form, e.g., metals and nonmetals into the compositions. If such materials are incorporated preferably they should be less than 5% by weight (based on the weight of the metal salts which are being functionalized), and more preferably less than about 2%.

Functionalization agents may also provide other useful functions to a formulation. As an example, the functionalization agents may also be antimicrobial materials (such as many cationic surfactants, phenoxy ethanol, 1-2 octane diol, etc.), may have UV stabilization (and/or UV absorption) properties (e.g., benzophenones, benzotriazoles, acrylic esters and triazines) which would reduce photochromic or photooxidation, may also have antioxidant properties as discussed earlier (e.g., ascorbic acid, butylated hydroxytoluene, furanones) and may be polymerization initiators (including photoinitiators) or dyes to impart superior polymerization characteristics to the monomer formulations these are added to or certain colors or fluorescence properties. In addition to UV stabilization, benzotriazole is also known to prevent oxidation of metals. One may add more than one of the surface functionalizing agents with different attributes. This allows products to be made economically with low added cost. As discussed later, some of the processing technologies disclosed herein are particularly suitable for achieving this in a facile way.

Besides providing outstanding antimicrobial properties, functionalized cuprous iodide by itself or in combination with cuprous bromide and/or sodium or potassium iodide can also be used to promote thermal stability of some polymers (e.g., nylons). For achieving both the thermal and antimicrobial properties the level of addition of copper iodide functionalized particles in bulk polymers should preferably be at least 0.05% by weight of the polymeric formulation and more preferably be at least about 0.1% (but still less than 5% in both cases).

Well dispersed finer particles in liquids or solids (including coatings) result in a more uniform distribution of the particles in the bulk material or on the coated surface and more of the surfaces of these particles is available to interact with the microbes. For particles that are a few nanometers in size, the surface functionalization can also influence their transportation into the interior of the microbes, such as penetration through the lipid layers. Functionalizing agents that may facilitate transport of nanoparticles to the surface of a microbe include surfactants, amino acids and combinations of amino acids and/or surfactants with peptides, polypeptides and carbohydrates. It was found that when certain embodiments of amino acids are used to functionalize the surfaces of the oligodynamic metal-containing nanoparticles, enhanced antimicrobial activity was obtained. Use of proper functionalization agents may also facilitate the transportation of the particles to the interior of biofilms so that the embedded microbes can be destroyed.

Amino acids which are preferred as amino acid functionalizing agents for the present nanoparticles include aspartic acid, leucine and lysine, although numerous other amino acids can also have efficacy. Also useful are combinations of amino acids, dipeptides, tripeptides and polypeptides. Other embodiments of functionalizing agents include carbohydrates such as mono- and di-saccharides and their derivatives, enzymes, glycols and alcoholic esters (e.g., Schercemol™ and Hydramol™ esters from Lubrizol (Wickliffe, Ohio)). Some of the polypeptides may also enhance the transport of the antimicrobial materials of this invention through the membrane of the microbes. Of the surfactants, anionic or non ionic surfactants are preferred.

Other embodiments of the invention are directed to various polymers that may be used for functionalization. Typically the functionalization procedure is done in a liquid medium in which these polymers are present in a solution and/or an emulsion form. Polyvinylpyrollidone and its copolymers represent one embodiment that can be an effective agent for modifying the surface chemistry of the antimicrobial particles. Examples of other polymeric surface modifiers include polyacrylic acid, copolymers comprising acrylic (including methacrylic acid) groups, soluble cellulosics (e.g., carboxy methyl cellulose), polyacrylamide, polyethylene and polypropylene glycols or oxides (and their copolymers), polyolefins modified with maleic anhydride (e.g., OREVAC® polymers from Arkema Group, King of Prussia, Pa.) polymers with alcoholic groups, urethanes, epoxies and carbohydrate polymers. As taught in several places in this specification, block and graft (including comb like polymers) copolymers are suitable under a variety of circumstances as they can provide good compatibility and dispersion characteristics. Each of the above polymers may have a range of molecular weights, typically in the range of about 1,500 and 1,000,000 Daltons, although molecular weights less than 200,000 are preferred, and molecular weights less than 25,000 are most preferred. Useful functionalizing polymers may also be combined with several of the other functionalization agents mentioned in this specification. Typically at least one of the functionalization agent has a minimum molecular weight of 60. Solubility and solution viscosity of the polymer generally correlates with average molecular weight, with high molecular weights being less soluble in water and resulting in more viscous solutions. When using block or graft copolymers, one may advantageously use those materials where sections in the copolymer have different properties in terms of ionic characteristics or their attraction/compatibility with water. For example, one block or graft may be hydrophobic or ionic, and another block or another graft or the main polymer chain may be hydrophilic or non-ionic, etc.

Another embodiment of functionalizing agents includes mercapto and thiol functionalizing agents in addition to the above-cited functionalizing agents. Thiol modifying agents useful for functionalizing the antimicrobial nanoparticles include aminothiol, thioglycerol, thioglycine, thiolactic acid, thiomalic acid, thiooctic acid and thiosilane. Combinations of thiol modifying agents can also be used in the present invention.

The functionalization of the particles may also provide additional attributes desirable for using them in practical applications. These attributes include the promotion of adhesion of the particles to and/or reaction of the particles with specific matrices such as in bulk materials and coatings and the enhancement of their antimicrobial properties by making the interaction between particles and microbes more attractive or by coupling or combining them with other materials for specific applications. Examples of other materials with which the present antimicrobial particles can be combined include antimicrobial agents which target a specific microbe or group of microbes, or materials that under illumination or humid or anaerobic conditions provide modified antimicrobial activity. The surface functionalization agents may also help disperse these particles in polymers, and for that purpose one may employ typical processing aids which are used in such applications. Some examples are stearic acid and their esters and salts (also see discussion on surfactants).

Examples of coupling agents and monomers for increasing the compatibility of the antimicrobial particles with various polymeric matrices include organosilanes (e.g., epoxy silanes for use in epoxy matrices, mercapto silanes for use in urethane and nylon matrices, acrylic, methacrylic and vinyl silanes for use in reactive polyester and acrylic polymers). Other monomers include those materials which have the ability to attach to the surfaces of the particles and also react or bond with matrices into which such modified particles are introduced. Some examples include polyolys (e.g. diols), silanes (includes silanated quats), metal alkoxides, acrylic polyols, methacrylic polyols, glycidyl ester acrylics and methacrylics.

Metal alkoxides and other metal oxide precursors (e.g., metallo-organic, water soluble silicate, aluminate, titanate and zirconate, mixed metal precursors such as alkoxy aluminum silicates, etc) may be used to functionalize the particles with layers of porous oxides containing materials. Some of the preferred materials contain silica, titania, alumina, zirconia, zinc and mixtures of these. In such cases, $M_1$-O-$M_2$ bonds are formed, where $M_1$ and $M_2$ may be different or the same metals and "O" represents oxygen. Such compositions may also include a proportion of monovalent and divalent metals such as sodium, potassium, calcium, barium, and magnesium to change the density (porosity) of the resulting oxides and their surface properties. There may also include residual organic groups from the precursors. These compositions may also contain organic reactive precursors, particularly hydrophilic precursors such as polyethylene oxide (molecular weight of about 200 to 10,000) to produce networks which are more open or with tailored porosity/hydrophilicity.

Some specific examples of metal alkoxides include tetraethylorthosilicate, tetramethylorthosilicate, titanium isopropoxide, aluminum isopropoxide, aluminum butoxide, zirconium ethoxide; and some specific examples of water soluble silicates include sodium silicate and potassium silicate. In some cases, more than one oxide composition may be used so that a first composition is used to modify the surface of the antimicrobial particles, and then a second or a subsequent composition is used to modify the surface of the first composition. This can assist in tailoring not only the porosity of the multilayer compositions, but also the final isoelectric points/chemistry so that the particles can be tailored to be compatible with any desired matrix.

A judiciously selected surface functionalization of this type can protect the particles from undesired interactions with their environments. This protection helps to maintain the particle integrity in environments where the chemical and/or physical composition of the particles may be degraded in absence of such protection. By tailoring the chemistry and the porosity of these functionalization layers, it is also possible to control the release rate of the antimicrobially-active species from the particles.

Embodiments of the invention also make use of surfactants for surface modification. The term surfactants would mean nonionic, cationic, anionic and amphoteric surfactants, some specific examples being Brij, Tween (polysorbate), Triton X-100, benzethonium, benzalkonium, dimethyldialkylonium, alkylpyridinium and alkyltrimethylammonium cations with any anion, e.g., bromide, chloride, acetate or methyl sulfate, silicone-ethylene oxide/propylene oxide copolymers (e.g., OFX-0190, OFX-0193 and OFX-5329 from Dow Corning, Midland, Mich.), Sodium dodecyl sulfate (SDS), sodium capryl sulfonate, sodium lauryl sulfate, sodium laureth sulfate, cetyltrimethylammonium chloride or cetyltrimethylammonium bromide (all available from Sigma-Aldrich Co, Milwaukee, Wis.), silicone surfactants, fluorosurfactants (e.g., Novec surfactants from 3M (St. Paul, Minn.) such as FC-4430, FC-4432, FC-4434 and FC-5120), salts of organic acids. Some others are fatty alcohol ethoxylates, alkyl phenol athoxylates, phosphate esters, acetylene diols (e.g., ethoxylated acetylene diols), salts of polyacrylic acid (e.g., sodium salts of polyacrylic acid) and soy lecithin. Anionic, amphoteric and nonionic surfactants are preferred, and anionic and non-ionic surfactants are most preferred.

One may also use surfactants (including emulsifiers) to form emulsions (including latex) of polymers and other materials, wherein such emulsions are used to modify the surfaces of the particles. For this purpose the polymers may be hydrophobic. Some examples include polyurethane emulsions, acrylic emulsions, fluorosilicone emulsions and epoxy emulsions. This method is particularly suitable where nanoparticles are made by grinding of larger particles of the antimicrobial materials in a liquid comprising a polymeric emulsion. The nanoparticles formed are functionalized by this emulsion. Alternatively one may grind the AM material in presence of a surfactant and then add this to the polymeric emulsion. Optionally, the functionalized particles may be dried as a powder and then added to the polymeric emulsion.

For oil based paints, one may use a variety of oil based surface modifiers, which may be easily incorporated on the surfaces of the particles by grinding. These may selected from different drying oils such as linseed oil, common industrial oil belonging to the class of polyunsaturated fatty acids. The viscosity of the grinding medium and other attributes may be controlled by adding solvents such as toluene, turpentine and white spirit. For some applications, particularly in preparing functionalized antimicrobial particles for cosmetic and personal care (body care) or for other uses, one may also use in oils and extracts for surface modification derived from natural sources or synthetic methods. These may also impart additional antimicrobial properties such as oils and extracts from eucalyptus, neem, cinnamon, clove and tea tree. One may also use oil emulsions in preparing the functionalized particles in an aqueous medium and then remove the water, before adding these surface modified particles to the oil based paint formulations. Some of the other functionalizing agents for personal care products (see Table 1c which includes toothpaste, soaps, shampoos, creams, other hair care products, deodorants and nail polish) are those which are used in such products, e.g., glycerin, benzyl alcohol, stearyl alcohol, polyethylene glycol or polyperopylene glycol diester of stearic acid, sorbitol, cetyl alcohol, carrageenans, disteearyldiammonium chloride, aloe leaf extract, cetearyl olivate, sorbitan olivate, caprylic/capric triglyceride, soyabean oil, olive oil, safflower oil, butylene glycol, potato extract, barley extract, sea-weed extract, wheat germ oil, cocamidopropyl betaine, lactic acid, sodium hyaluroate, malic acid, algae extract, cholestrol, sucralose, witch hazel extract, hydrogenated lecithin, cycloymethicone, aqualine, linolic aciddimethicone copolyol, xanthan gum, polyethylene glycol (PEG) and polypropylene glycol (PPG) dimethicones, sodium laureth-13 carboxylate, copolymer of methyl vinyl ether and maleic anhydride, bisamino PEG/PPG 41/3 aminoethyl PG-propyl dimethicone, amine functionalized silicones (amidomethicone) and block copolymers of PEG and PPG (e.g., triblock copolymer such as Pluronics™ available from BASF, Germany). PEG and polyethyleneoxide are considered the same in this disclosure.

Other embodiments of functionalizing agents employ ligand-specific binding agents. For example, functionalization using autoinducer or quorum sensing molecules (e.g., N-undecanoyl-L-Homoserine lactone and N-heptanoyl-L-Homoserine lactone) may facilitate the delivery of the antimicrobial materials through biofilms, and may help delay or prevent the formation of biofilms. Functionalizing agents may also have other useful or antimicrobial properties, which may be effectively combined with the antimicrobial particles. As examples, salts of argenine and acidic polymers have been suggested for use in toothpastes for promoting oral hygiene (US 2009/0202456), and chitosans and curcumin have been also suggested for use as antimicrobial materials and all of these may be used as functionalizing agents.

Yet other examples include cecropin, caprylic acid and monocaprylin. As another specific example, it has been demonstrated (Corinne K. Cusumano, et al., Sci Transl Med 3, 109ra115 (2011) (DOI: 10.1126/scitranslmed.3003021 "Treatment and Prevention of Urinary Tract Infection with Orally Active FimH Inhibitors") that mannoside compounds are effective in preventing uropathogenic *E. coli* infections in women by inhibiting the ability of the bacteria to bind to epithelial cells of the bladder via FimH receptors. One may use such compounds to modify the surfaces of particles of this invention to target *E. coli* with specificity. In one embodiment, the mannoside compounds may be used as functionalizing agents for the metal salt nanoparticles of present invention. In another embodiment, mannoside compounds may be included within the coatings used in urinary tract catheters.

The same approach may be used to target specific microbes responsible for specific pathogenic infections. There is an abundant and expanding literature on receptors on cell surfaces to which microbes bind; and utilizing tailored compounds as functionalizing agents which interfere with such binding can readily be carried out. Beyond this, one of ordinary skill will be able to identify various ligand-target combinations to design any manner of ligand-specific targeting agents to use as functionalizing agents for the particles of the present invention.

Other embodiments of the invention include affinity-based targeting mechanisms such as using certain inherent properties of microbes' external structures to target the metal halide nanoparticles to. For example, the peptidoglycan layer of Gram-positive bacteria is a polymer of sugars and peptides and has a generally negative charge. Other polymers, such as PVP or PEG may be attracted to the peptidoglycan surface on the basis of hydrophobic interactions, and once there, may stick to and deliver the stabilized metal halide particles to the surfaces of the microbes, which in turn will deliver the antimicrobial-active ionic species. Likewise, Mannose-binding lectin (MBL) and/or Lipopolysaccharide binding protein (LBP) may be included as functionalizing agents. MBL recognizes certain carbohydrate patterns on microbial surfaces and LBP binds to Lipopolysaccharide, which comprises a majority of the outer membrane of Gram-negative bacteria.

In other embodiments of the present invention, after producing the functionalized particles in liquid media, these may be dried into solid powders. Such solid powders are easier to store and transport and may be also used in downstream processing with greater ease. The size of such dried powders particles will in general be larger than the size of the individual functionalized particles, and the particles of such dried powder particles will contain a number of the functionalized antimicrobial particles. The size of the dried powder particles should be greater than about 1 microns, preferably greater than about 10 microns and most preferably greater than about 100 microns. This allows downstream operations using the dry powders to be conducted safely without having the powder particles become airborne. The larger particles do not get airborne easily and further 100 micron particle size are larger than the thoracic airways of human lungs, Further, with increasing size the particles are difficult to inhale and flowability in processing also improves.

The dried powders may then be used to make antimicrobial products by adding them to a liquid carrier or a solid carrier. Use of solid carriers includes compounding these powders with a polymeric material in the molten state. When these powder particles are added to the carriers (liquid or solid), these particles will generally break down and result in a uniform dispersion of the smaller functionalized particles. Surface functionalization may also assist in the size reduction of the powders when blended with the carriers.

In still other embodiments of the present invention, one may add other agents (preferably other polymers) before the drying step used to form the solid powders. This is useful for producing larger powder particles upon drying. Such added agents can increase the cohesiveness of the assembly of functionalized particles and effectively serve as a binder, which is useful in providing stability during subsequent handling. Polymeric functionalizing agents may provide or contribute to this function. Typically when the molecular weight of the functionalizing agent is less than about 500, it is advantageous to add a polymeric binder which preferably has a molecular weight greater than about 3,000. As an example, one may use PVP, PEO or other polymers along with surfactants, where the surfactants have a molecular weight of less than 500 and the polymers have a molecular weight of greater than 3,000. Preferably, the volume percent of the surface modifiers and the polymeric additives should be in excess of 20%, and more preferably in excess of 40%.

h. Porous Particles and Particles with Core-Shell Geometry

Other embodiments of the invention are directed to compositions having antimicrobial activity comprising a metal halide, and a porous carrier particle in which the metal halide is infused, the carrier particle stabilizing the metal halide such that an antimicrobially effective amount of ions are released into the environment of the microbe. The terms "porous particle" and "porous carrier particle" are used interchangeably herein. In one embodiment, one may form the antimicrobial compositions within the porosity of larger porous carrier particles. Metals and metal compounds or salts, particularly metal halides are preferred materials for this infusion. For example one may infuse silver bromide or particularly copper iodide into the pores. The porous particles should preferably have interconnected pores. A preferred upper range of the carrier particle is below 100 μm, and more preferably below 20 μm and most preferably below 5 μm. The average pore size (average pore diameter) of the carrier particles should be less than about 100 nm, preferably less than about 50 nm and most preferably less than about 20 nm.

In other embodiments it is preferred that the surfaces of the porous particles (including the pore surfaces) are hygroscopic (an abundance of silanol or other hydroxyl groups on the surface leads to hygroscopic materials). One preferred class of carrier particles that can be used are "wide pore" silicas. The carrier particles may be of any shape, e.g., spherical, irregular, angular, cylindrical, etc. For example, SILIASPHERE™ silicas from Silicycle (Quebec, Canada) may be used. The preferred silicas have a pore size (average pore diameter) in the range of 2 to 100 nm, more preferably 4 to 20 nm). Another class of porous particles includes precipitated silicas, such as Zeothix™ and Zeofree™ from Huber Corporation (Atlanta, Ga.) and Sipernat™ from Evonik Industries (Evonik Degussa Corporation, Parsippany, N.J.).

The porous carrier particles containing antimicrobial compositions in the pores can then be incorporated into bulk products, coatings, solutions, low viscosity suspensions such as many shampoos, high viscosity suspensions such as creams and gels to impart antimicrobial properties. These may be added as fillers to polymers which may then be shaped into bulk products via molding, extrusion, etc. Porous particles may also be prepared in a form of a large three dimensional shapes such as plates, tubings or any other desired shapes. The AM material may be incorporated in these using solutions so that the bulk materials acquire antimicrobial properties. For example, a natural tubular material that is mined may be used for this purpose. These are called Halloysite clays and are available from Applied Minerals (New York, N.Y.). These clay tubes are typically between 0.5-3.0 microns in length, with an exterior diameter in the range of 50-70 nanometers and an internal diameter (lumen) in the range of 15-30 nanometers. In addition to imparting antimicrobial properties, the use of these clays in plastics in low concentrations can also lead to enhancements in modulus, strength and abrasion resistance.

These porous materials are not used as ion-exchange materials as are typical synthetic or natural zeolites, bentonite clays, hydroxyapatites and zirconium phosphates. Such ion exchange materials contain molecular channels with a size generally less than 1 nm which typically allow only single ions and very small molecules to pass through. Further, ion exchange is conducted using solutions of salts with high water solubility. For example, when conducting cationic ion exchange the cations from the salt are exchanged with the cations already present in the ion exchange medium. For example, a zeolite or an ion-exchange porous material may contain sodium ions in the framework of the porous material. When this is exposed to e.g., a solution of silver nitrate in water (silver nitrate is highly soluble in water and results in silver and nitrate ions), the sodium ions will be replaced or exchanged with silver ions, so that gradually the aqueous medium will get more concentrated with sodium ions. After the process, the ion exchanged porous particles are washed to remove soluble salts and have a fraction of sodium ions replaced by silver ions.

In contrast to this, a salt or compound deposition process of the present invention is different and does not involve ion-exchange. The antimicrobial salt is deposited in pores of selected porous particles. For example, if one wants to deposit a copper salt or a silver salt, then both the anions and the cations are deposited. Further, the deposition process does not require that some other ion must be exchanged from the porous material. This deposition may be done from solutions which are soaked into the pores and dried, or soaking precursors or precursor solutions in the pores so that they react and desirable salts are formed within the pores, where they get trapped. Further, zeolites and the other ion exchange type materials are crystals with well defined molecular channels. On the contrary, the preferred porous materials used in the present invention are amorphous and usually inexpensive, and their pores are typically larger and irregular. In our invention we deposit salts (both cations and anions) in the channels (or pores) of the porous materials and one can deposit more than one type of antimicrobial salt or a compound. One can certainly mix the materials of this invention with other antimicrobials wherein the other antimicrobials include silver, copper and/or zinc ion-exchanged zeolites. One may even use composite particles where the antimicrobial action comes from both ion-exchanged metals and deposited salts, wherein zeolites with sufficiently large pore size (preferably greater than 2 nm) are ion exchanged to contain at least one of silver, copper and zinc ions, and then in a subsequent process low water solubility salt (e.g., salts of copper and/or silver) are deposited in these pores.

For deposition of metal compounds, particularly metal halides such as copper iodide are dissolved in non-aqueous solvents such as acetonitrile and dimethylformamide (DMF). The porous particles are then treated with these solutions so that they permeate the pores, and then excess solution is removed. As the solvent from the pores is dried, their removal leaves the metal halide coatings/deposits on the particles and within the pores. This infusion of solution into the pores may be assisted by applying vacuum to the solution so as to extract air from within the particles, and then the removal of vacuum allows the solution to penetrate the pores more effectively. The porous carrier particles are then removed (e.g., by centrifugation, filtering, etc.).

Solvent selection plays a fundamental role in the use of porous carrier particles for delivery of inorganic metal compounds. Since an important part of the process is to ensure that solutions easily soak into the pores of the porous particles, it is required that the surfaces of the pores are compatible with the solvents used to form these solutions. In one embodiment, when the surfaces of the pores have hydrophilic properties, solvents with high dielectric constant such as water, ethanol, methanol, acetonitrile, dimethylformamide, etc., are easily wicked into the pores by capillary forces. The rate of release of ions can be tailored by varying the size of the porous particles, particle shape and pore geometry (including pore size). In general, smaller particle sizes, elongated or irregular particle shapes vs spherical particle shapes given the same particle volume, and larger pore sizes will result in increased rates of ion release. One may mix different sized particles and also particles with different pore sizes to tailor release properties to suit both short term and long term release of ions in final products. Generally the size of the porous particles is varied between about 0.5 to 20 microns and pore size between 2 nm to 20 nm, with 4 to 15 nm being more preferred. These particles also have high surface areas. Typically particles with surface areas greater than about 20 $m^2/g$ are desirable, and those with surface areas greater than about 100 $m^2/g$ are preferred.

The particles of this invention may also be fabricated in a core-shell geometry, wherein the core may be a solid support and these are treated with solutions as described above so that these get coated with an antimicrobial material. That is rather then using porous particles, solid particles are used. Examples of core materials are silica, titania, sand and carbon. The amount of antimicrobial material in a core-shell particle is greater than 1% and preferably greater than 20% by weight of the total core shell particle.

Another variation in core shell geometry is where the antimicrobial particles are first formed in a desired size and then these are encapsulated in porous or permeable shells so as to allow the antimicrobial material or the ions to pass through.

In another process embodiment, non-water soluble (or with low water solubility) metal halides may be formed in the pores using aqueous solutions. Aqueous solutions are formed using water soluble salts of the desired metals (precursor salts). The porous carrier particles are treated with these solutions and removed. These particles may be optionally dried. The treated particles are then treated with a second solution comprising another water soluble salt with the desired halide anion. When the second salt solution permeates the pores of the particles and comes in contact with the with the precursor salts, the required metal halides (with low water solubility) form by precipitation as the two salts react and are trapped in the pores of the particles resulting in antimicrobial particles. If surface functionalization of the deposited materials is desired, one of the said halide salt solutions may include surface functionalization agents. After drying, these particles may then be subjected to another series of similar treatment to precipitate more of the target metal or metal compound, or to precipitate a second compound or metal in the pores (e.g., depositing AgBr in pores which previously have been treated to deposit CuI). One may also form antimicrobial particles by mixing different types of porous particles comprising different compositions of metals and metal compounds. One particular embodiment comprises forming antimicrobial compositions by mixing two or more types of particles with different antimicrobial materials trapped in their pores. These formulations may then be added to products in order to form products with antimicrobial properties.

In a process embodiment of the present invention, one may also form antimicrobial porous particles with deposits of silver metal. Such particles can then be used to make antimicrobial formulations. The infusion of silver metal in a porous carrier particle is generally performed by starting with an aqueous solution of a metal salt (e.g. silver nitrate with the surface modifiers (if used) dissolved therein) in water. The porous particles are added to this solution so as to infuse the solution into the pores. This infusion may be assisted by applying vacuum to the solution so as to extract air from within the particles, and then the removal of vacuum allows the solution to penetrate the pores more effectively. The porous carrier particles are then removed (e.g., by centrifugation, filtering, etc.) and optionally dried. The particles (wet or dry) are then added to an aqueous solution of reducing agent (e.g., 0.25% w/w $NaBH_4$) which causes small particles of the metal (in this case, silver) to precipitate within the pores and also on the surfaces of the porous carrier particles.

i. Formation of Functionalized Particles by Grinding

In an earlier section on functionalization materials, several examples were cited which used grinding as a method to produce functionalized particles. Generally the starting particles of the antimicrobial materials have an average size larger than 1 micron, typically in the range of 1 to 1,000 microns. These are reduced in the grinding step to an average size below 1 micron (1,000 nm) or even below 100 nm or even below 10 nm depending on the desired size. This process is described in more detail in this section.

In this operation the functionalization materials are incorporated into the grinding medium or incorporated soon after the grinding operation. There are many advantages of the grinding process which include: (a) increased yield both in terms of amount and the concentration of the particles produced. (b) scalability on an industrial scale; (c) reduced waste both in terms of hazardous chemicals and also in terms of additional equivalents of starting materials that are typically required in chemical synthesis methods; (d) reduced energy requirements in terms of simplified processes and handling, removal and drying of larger quantity of solvents relative to the material produced; (e) reduced cost of production while adopting "clean and green" manufacturing methods; (f) increased versatility in terms of the chemistry of the functionalizing agent; (g enhanced capability in being able to use more than one functionalization agent with different chemistries; (h) avoidance of the long development process which is typically required for each new set of particle composition and functionalization agent when chemical synthesis methods are used; (i) new capability of imparting additional attributes to the antimicrobial materials via the functionalization agents; (j) increased ability to tune/control the size of the resulting particles from a few nanometers to 1,000 nm or above; and improved ability to produce fine antimicrobial particles without introducing undesirable amounts of functionalization agents.

As an example, in many of the chemical synthesis methods where functionalized particles are made in solvent systems, such as making CuI particles functionalized with PVP, the latitude for processing and the materials used is quite limited in terms of the type of the chemistry of the antimicrobial particle being formed and also the chemistry of the surface functionalization material. First, both the antimicrobial material (e.g., CuI) and functionalization agent (e.g., PVP) have to be soluble in a common solvent (such as acetonitrile). Second, the amount of functionalization agent required is very high when small particles are produced—typically the weight ratio of antimicrobial particle material to the surface functionalization agent is about 5:100 or less, and generally 1:100 or less. This results in significant amount of the functionalization agent which ends up in final products and often compromises the properties of those products. In the grinding method one may use a very high weight ratio of antimicrobial particle material to the surface functionalization agent, such as 1:1 or higher, and preferably equal to or greater than 3:1 and more preferably equal to or greater than 9:1. Third, one must handle and dispose of the solvent used in the synthesis, which introduces additional cost and complexity to the process. Fourth, it can be a major undertaking to change the chemistry of the particles or the functionalization agent.

As another example, consider the limitation of the chemical method which is typically used for making silver iodide nanoparticles. These particles are made by taking an aqueous solution of a soluble silver salt such as silver nitrate along with a water-soluble polymer such as PVP. To this under stirring conditions is added another aqueous solution of sodium iodide (sodium iodide is soluble in water as well). This causes silver iodide particles to precipitate. In this case, the ratio of Ag to the functionalization agent is also about 1:100, with an added complication of removing sodium and nitrate ions. Further, if one needs to add 0.1% of the antimicrobial agent to a product, then the functionalization agent would be present in a 10% concentration. Such large additions of the functionalization agents may considerably modify the properties of the product in an undesirable way, unless such functionalization agents are present in the product in significant concentrations to impart other attributes (e.g., plasticizers, carriers, gelling agents, monomers that react to form the polymer—such as in polyurethanes, epoxies, etc.). Still further, difficulties are encountered if one wants to functionalize with materials which are not soluble in water; and new synthesis routes must be explored if one wants to change the chemistry of the antimicrobial particles.

One may also produce functionalized particles by grinding in presence of monomers which include metal oxide precursors. This grinding may be done at a first pH, and after grinding, the pH is changed to a different or a second pH to promote additional reactions. As an example, one may grind the desired metal halide in the presence of a silica alkoxide precursor such as tetraethylorthosilicate (TEOS) in an acidic medium (e.g., pH lower than 7) so that the monomer is able to hydrolyze and attach to the surface of the ground particles. Once the grinding is over the material in a subsequent step is removed and the pH is changed (e.g., it is raised to over 7) so that the silica precursor functionalizing the particles condenses and forms a porous medium around the ground particles. An additional grinding process may be introduced after the previous step to break any particle agglomerates. One may also mix more than one precursor during grinding (e.g. mixtures of metal alkoxides or other precursors of the same metal or of different metals). One may add all of the precursor before grinding or add them sequentially during the grinding process and the addition may even continue even after the grinding is completed. The composition and/or quantity of each addition may be the same or different. The particles obtained after the grinding operation may be refluxed to promote condensation of the functionalization agent while still in a liquid matrix, or dried and then subjected to higher temperature heat treatments for reducing the porosity. Further, one may even heat treat the particles to a sufficiently high temperature to burn off any residual organics which may be present in the formulation. As a variation one may produce functionalized particles with any desirable material (e.g., PVP) by grinding, and then add a monomer and polymerize this to further encapsulate the functionalized particle.

As an additional example, many useful paints and varnishes are deposited from aqueous formulations containing polymeric emulsions. Typically these polymers are not water soluble so that the coatings after drying are water-resistant; but for processing, these polymers are made compatible with water formulations by polymerizing them in water with surfactants so that water-stable emulsions can be formed. Since a wide range of polymers are used with many different kinds of surfactants, it is very challenging to develop chemical methods to accommodate the different emulsions and particles. In contrast, in the preferred process embodiment of the present invention, CuI (or another antimicrobial material) can be ground with these emulsions (or surfactants used to form these emulsions) to make antimicrobial formulations in a simple way. The process does not require addition of any extra ingredients which have the potential to change the properties of products containing the antimicrobial particles. Further, formulations made using the present process invention can be used as such and do not require handling of solvents and their removal, or production of byproducts which need to be removed, all of which lead to greener production technologies with lower energy consumption.

There are many examples and teachings in the present application which demonstrate one or more merits of the grinding method.

One such method of forming the desired microparticles and nanoparticles is by grinding of larger particles in a wet media mill. Such grinding is done in the presence of one or more functionalizing agents in an appropriate liquid medium, e.g. water. Wet media mills are available from several sources such as NETZSCH Fine Particle Technology, LLC., Exton Pa. (e.g., Nanomill Zeta®); Custom Milling and Consulting, Fleetwood, Pa. (e.g., Super Mill Plus); Glen Mills Inc, Clifton N.J. (e.g., Dyno® Mill). These mills typically comprise chambers in which hard ceramic or metal beads (grinding media) are vigorously stirred along with the slurries of the powders which result in grinding of the powders down to finer sizes. Typically, the size of the beads is about 1,000 times or more larger than the smallest average size to which the particles are ground to. In a single step grinding process, it is preferred to use beads about 1 mm or smaller and more preferably in the range of about 0.04 to 0.5 mm and most preferably 0.3 mm or smaller. The grinding procedure may start with a larger bead size to grind initially the large chunks/particles of antimicrobial material to a smaller particle size and then using smaller beads to reduce the particle size further. As an example, when one starts grinding particles which have a starting size in the range of about 30-50 microns, a bead size of 0.3 mm may be used, which will result in particles of about 100-400 nm in average size. In the next stage, one may use beads of 0.1 mm in diameter which results in particles ground to about 30-100 nm, and next one would use 0.05 mm diameter beads which provide particles in the range of about 15-50 nm. The particle size of the ground particles is not only dependent on the size of the beads, and other grinding parameters such as time and speed of grinding, but also on the formulation. As an example, for a given set of grinding parameters, the concentration of material being ground and the type and amount of surface functionalization, the amount of viscosity controller (if any) and other additives will influence the particle size. For a material being ground in water (carrier), the following formulation variables will reduce the particle size when the same grinding parameters are used. These are (a) smaller amounts of material relative to the carrier, (b) use of a functionalizing agent that bind strongly to the surfaces of the particles of the material being ground, and (c) use of functionalizing agents that result in low viscosity. Under certain conditions one can produce particles as small as 5 nm using grinding beads which are 0.1 mm in size. Functionalizing agents may be present at the start of the grinding process (preferred), or more amounts or different agents may be added as the grinding proceeds.

A wide range of particle sizes may be used to provide antimicrobial properties to products incorporating such particles, but particle sizes below about 300 nm are preferred. The liquid media from the grinding containing the ground particles may be directly incorporated in products (e.g., in coating formulations, low viscosity suspensions such as many shampoos, high viscosity suspensions such as creams and gels, etc.), or these may be dried (e.g., using a rotary evaporator unit or by spray drying) so that the particles along with the functionalizing agents are obtained as powders or flakes, where these powders or flakes particles are preferably sufficiently large to minimize potential health issues for workers handling the materials. The particles or flakes may then be incorporated in useful formulations including melt blending with other polymers to form products by molding, extrusion, powder coating, etc.

In order to obtain dry powders, where the size of the powder or flake material is large (preferably greater than 1 microns, more preferably greater than 10 microns and most preferably greater than 100 microns), where powder or flake particle contains several functionalized anti microbial particles, it is preferred that before drying the liquid, sufficient functionalizing agents and/or polymers (e.g., which can provide a binding function) are added, so that the volume percent of the functionalizing agent and the polymeric material is preferably greater than 20% or more preferably greater than 40% in the dry state. The binding additives (if different from the functionalizing agents) may also be added after the grinding process is complete, As a specific example, one may use 60-95% of metal halide (e.g., CuI) particles by weight, with 1-5% of an anionic surfactant and/or other ingredients by weight, and the remainder being a polymeric binder by weight. This would meet the volume percentage criteria taught immediately above. As an example a formulation with 90% CuI and 10% PVP (both by weight as solids), when converted to volume fraction using their respective specific gravities of 5.67 and 1.2 would result in about 66% of CuI by volume and 34% PVP by volume.

It is preferred to add the functionalizing agents while the particles are being ground and smaller particles with fresh surfaces are produced. There is, however, an exception to this process protocol which can be use to advantage. The particles may be produced by grinding so as to reduce the size of the larger particles of the antimicrobial material in water (or acidified water) or even in an inert liquid medium. After the grinding process is substantially over, i.e., after the desired particle size is about reached, the surface functionalization agents are added and a short period of additional grinding is carried out to produce the desired functionalized particles. One may also add more than one functionalization agent, where these may be added together or at different times.

When grinding is carried out in an aqueous medium, where surface hydroxyl groups on the particles (formed as a result of grinding in water), the functionalizing materials should be so selected so that they can interact with these hydroxyl groups and bond to or react with them. If the grinding is carried out in an inert medium, the functionalizing materials should be selected so as to be able to interact with the newly formed surfaces.

In those processes where the functionalizing agent is added after the grinding operation, these agents are preferably added before the particles start agglomerating into larger sizes. From our practical experience we have noted that this addition of the functionalization agent should preferably be done within 48 hours of grinding, and more preferably immediately after grinding. One may even optionally introduce a second step of grinding after adding the surface functionalization agent for more intimate and a quick dispersion of the added material and also to break agglomerates that may have formed during the waiting period. More than one functionalization agents may be added during the grinding process. These may be added together or at separate or different times. For example the grinding may commence with one functionalization agent and later more of the same or a different functionalization agent may be added.

One advantage of using the grinding process to produce functionalized particles of antimicrobial materials is the ability to use minerals which have antimicrobial compounds naturally incorporated in them. Such minerals can be ground to provide antimicrobial materials. Such grinding is preferably done in presence of functionalizing agents. Some examples of minerals with silver or copper halides along with their principal compositions are Iodagyrite (AgI), Bromargyrite (AgBr), Chlorargyrite (AgCl), Iodian Bromian Chlorargyrite (Ag(I, Br, Cl)), Nantokite (CuCl) and Marshite (CuI).

Another significant advantage of grinding is to be able to use several materials for functionalization which may be used simultaneously. More specifically, one can use complete formulation of a product to functionalize the particles. For example, these may be complete or partial personal care formulations, drug formulations, etc. Some specific examples are shampoos, soaps, mouthwash, deodorants, toothpaste, etc. For example in a toothpaste, the formulation used in grinding may be partial i.e., before adding opacifiers or dentrifices, etc. If the formulations are solids then these can be dissolved or diluted using solvents (e.g., dissolving solid soap in water), etc. Solvents may be removed before adding them to the final product or these may be removed after adding them to the final product. This is similar to making a concentrated masterbatch of the functionalized particles using final formulation (or a partial formulation), and then mixing these in the final product in the desired antimicrobial concentration.

The grinding method is generally more suitable for materials which are brittle and have a hardness and toughness lower than that of the grinding beads. The principal material to be ground should be lower in hardness as compared to the grinding beads. On Mohs scale, the hardness of the principal material to be ground should preferably be smaller than that of the grinding media by a factor of at least 2 Moh units or more and more preferably 3 units or more. Further the principal material to be ground should be brittle. In general, brittle materials often have fracture toughness ($K_{1C}$) of less than 2 Mpa-m$^{1/2}$. Many of the metal halides and the preferred metal salts of silver and copper are available as powders, and their fracture toughness is not mentioned or evaluated. However, most of these materials (silver halides, copper halides, CuSCN and Cu$_2$O) are soft and brittle (not malleable) by nature and are easily processed by grinding. Usually copper and silver halides have hardness in the range of 2 to 3 on the Moh's scale, and Cu$_2$O crystals have a hardness in the range of 3.5 to 4 on the same scale. The process of grinding to make functionalized antimicrobial nanoparticles discovered in the present work is applicable to a wide range of metal halides and other copper salts of interest. The process is also useful for preparing functionalized particles of other compounds (e.g., AgBr, AgI), such as brittle metal oxides (e.g., zinc oxide, silver oxide and cuprous oxide).

The lining of the grinding vessel may be ceramic or of metallic or may have a polymeric finish. Typical grinding beads are hard, tough ceramic compositions such as compositions based on zirconium oxides (zirconia). Hard beads with zirconia comprising at least one of yttrium oxide, magnesium oxide, cerium oxide and calcium oxide are commercially available. The. Some suppliers for stabilized zirconia and or alumina beads (grinding media) include yttria stabilized zirconia (YTZ) beads from Tosoh USA (Grove City, Ohio) which have 5% yttria and 95% zirconia with a hardness of HV 1250 and fracture toughness of 6 MPa-m$^{0.5}$, others are Prime Export and Import Company Ltd (China), Stanford Materials (Irvine, Calif.), Inframet Advanced Materials (Manchester, Conn.) and ZGC beads from 3M (St. Paul, Minn.). Typically, the material is ground in a liquid medium which does not solubilize the material being ground. However, it may be beneficial to add a limited amount of solvent (which by itself will solubilize the material being ground) to the grinding medium to increase the process efficiency of grinding. These are added in addition to the surface functionalizing agents. It is preferred that this solvent is compatible with the liquid medium. As an example in grinding copper iodide, one may use water as the grinding media and acetonitrile as the solvent additive. Typically solvent concentration to the liquid medium is less than 20% by volume, and preferably less than 10%. One may also use azeotropic mixtures of the solvent and the liquid medium as long as the solubility of the material is low, preferably less than 100 ppm.

One may grind more than one material to produce functionalized particles of several chemistries simultaneously. For example, one may grind more than one copper salt, or mixtures of copper and silver salts, etc. Some of the preferred combinations include copper halides and silver halides, e.g., CuI and AgBr; or CuI, AgBr and AgI; or CuI and AgI, etc.

We have also found that when the functionalized particles are formed by grinding, small amounts of materials in their elemental form may be added during the process. These include metals. These metals interact with the surface of the particles and the functionalization agents to help control the coloration of the formed materials and also in modification of antimicrobial properties. Some of the preferred metals are gold, silver, copper and zinc. An example of a nonmetal is iodine.

j. Highly Water Soluble Salts

We have also seen that selective water soluble salts help with dispersion, i.e., stabilization of particles in a liquid medium or better dispersability in a solid medium. Typical solubilities of these water soluble salts are preferably in excess of 1 g/liter. These salts (organic or inorganic) typically have strong interactions with the material being ground and are preferably used in association with surface functionalization agents. The addition of water soluble salts with antimicrobial properties may also help in providing antimicrobial efficacy at different time points (e.g., a burst of activity at shorter times). They may also provide buffering effects, or control the redox properties of the ions (e.g., stabilizing cuprous ions, or stabilizing iodide ions in compositions comprising cuprous and/or iodide ions), or provide compatibility with other ingredients in the composition. The antimicrobial compositions may be used as suspensions in aqueous or non-aqueous liquid media, or be solids.

Some example of soluble salts which have shown promise with metal halides of low water solubility (particularly copper and silver halides) include organic salts and salts of elements selected from at least one of lithium, sodium, potassium, calcium, magnesium, barium and zinc. Further, the antimicrobial compositions may also comprise high water solubility salts of copper, silver and nickel. Some specific examples of highly water soluble salts are sodium acetate, sodium citrate, sodium cinnamate, sodium gluconate, similar salts of potassium, calcium, copper and silver; halide salts of lithium, sodium and potassium, calcium, magnesium zinc and copper; silver nitrate, sodium and potassium thiosulfate.

2. Theory

While not wanting to be bound by a particular theory regarding the origin of the surprising antimicrobial effectiveness of the novel compositions of the present invention, it is currently believed that the compositions of the invention (or ions released therefrom) are attracted to the surfaces of target pathogens. Once attached to the surfaces of the pathogens, the active oligodynamic species (generally metal cations but also including anions such as iodide) are transferred from the particles onto and/or into the pathogens. In some embodiments, the interaction between the functionalized particles and the pathogens may be sufficiently strong that the particles become embedded in the outer membrane of the pathogen, which can have a deleterious effect on membrane function. In other embodiments, particularly when the particles are very small (as less than 10 nm in size), the functionalized particles can be transported across the outer membrane of the pathogen and become internalized. Under these conditions, the oligodynamic species can directly transfer from the particles into the pathogen, bind to proteins, organelles, RNA, DNA etc. thereby hindering normal cellular processes. In the case of bacteria, this would correspond to the direct deposition of the active oligodynamic species in the periplasm or cytoplasm of the bacteria. This theory of the operative mechanism of the invention is just that, and is one of many that could explain the underlying efficacy.

3. Uses of the Compositions and Incorporation Methods in Products

The embodiments of the present invention have utility in a wide range of antimicrobial applications. These applications or products may be liquids or solids. Some of these applications are set forth in Table 3 below. Besides their direct use as antimicrobial compounds, other embodiments include several ways in which the functionalized particles can be incorporated into other materials to obtain novel and useful objects.

TABLE 3

Representative applications of functionalized antimicrobial particles

| No. | Application |
|---|---|
| 1. | Antimicrobial agents, administered either orally or via IV infusion |
| 2. | Coatings on medical implants |
| 3. | Constituents of medical implants |
| 4. | Sutures and medical devices |
| 5. | Pacemaker and hearing aid housings and leads |
| 6. | Coatings on or constituents of ventilator equipment, particularly the humidification components of such equipment |
| 7. | Medical and surgical gloves |
| 8. | Masks |
| 9. | Dental adhesives, primers, sealants and composite fillings used for tooth restoration, and other tooth restoration products such as dentures, crowns, bridges and coatings including coatings on implants. |
| 10. | Objects and coatings to prevent formation of biofilms, in medical applications, e.g., urinary tract and long dwell catheters |
| 11. | Topical creams for medical use including use on wounds, cuts, burns, skin and nail infections |
| 12. | Use in wound dressings (includes gauzes, bandages, etc.) |
| 13. | Coatings on bottles, containers or incorporated into the material of the containers used for containing medical or ophthalmic solutions |
| 14. | Clothing for medical personnel, including nurses and surgeons |
| 15. | Textiles including bedding towels, undergarments, socks, sportswear, uniforms and technical textiles (antimicrobial agent is in fibers or as coating on fibers or fabrics) for microbial and odor control |
| 16. | Coatings on and constituents of shopping bags |
| 17. | Upholstery, carpets and other textiles, wherein the particles are incorporated into the fibers or as coatings |
| 18. | Self disinfecting wipes |
| 19. | Coatings on or direct incorporation in components of ventilators, air ducts, cooling coils and radiators (for use in buildings and transportation) |
| 20. | Coatings on furniture for public use, such as in hospitals, doctors' offices and restaurants |
| 21. | Wall coatings in buildings, and incorporation as coatings or in bulk of building components such as floors, appliances, bathroom surfaces, handles, knobs, sinks, toilet seats, shower heads, tables and seating particularly public buildings such as hospitals, doctors' offices, schools, restaurants and hotels |

TABLE 3-continued

Representative applications of functionalized antimicrobial particles

| No. | Application |
|---|---|
| 22. | Coatings or compositions for use in transportation, such as ships, planes, buses, trains and taxis, where the antimicrobial compositions and coatings may be used for/applied to walls, floors, appliances, bathroom surfaces, handles, trays, steering wheels, knobs, tables and seating |
| 23. | Coatings on school desks |
| 24. | Coatings on plastic containers and trays |
| 25. | Coatings on leather, purses, wallets and shoes, and also incorporating antimicrobial materials with the bulk of the materials to make these (e.g. shoe soles, and uppers), odor control |
| 26. | Coating of flowers and flower heads |
| 27. | Incorporation in gloves, and liners for gloves, shoes and jackets |
| 28. | Filters for water supplies and air, water and air delivery systems, air humidifiers |
| 29. | Use as a biocide in aqueous systems |
| 30. | Coatings for prevention of biofilms on marine applications |
| 31. | Coatings on or direct incorporation in keyboards, switches, knobs, handles, steering wheels, remote controls, of automobiles, cell phones, optical video and data disks and other portable electronics |
| 32. | Anodized coatings |
| 33. | Powder and coil coatings including for applications in furniture, appliances, handles, knobs, etc. |
| 34. | Coatings on toys, books and other articles for children |
| 35. | Coatings on or incorporation in gambling chips, gaming machines, dice, etc. |
| 36. | Bottle coatings for infant's bottles |
| 37. | Coatings on cribs and bassinettes |
| 38. | Coatings on handles of shopping carts |
| 39. | Coatings or direct incorporation in personal items/use such as toothbrushes, hair curlers/straighteners, combs and hair brushes, brushes for cosmetic application (both for application of dry and wet materials) |
| 40. | Liquid cleaners/treatments/disinfectants (including sprays) for surfaces in household, industrial and medical facility applications |
| 41. | Nail polish including base and top coats |
| 42. | Shampoos for treating chronic scalp infections, antidandruff shampoos, hair detangling treatments, hair gel and other hair treatments |
| 43. | Incorporation in tooth paste, mouthwash and tooth brushes |
| 44. | Anti-odor formulations, including applications for personal hygiene such as deodorants |
| 45. | Other body care products such as creams (including moisturizing and anti wrinkle creams, UV protection creams), shaving creams/gels, soaps (liquids, gel and solid), sanitizers, powders, mascara, blush, foundation and other cosmetic applications. |
| 46. | Coatings on currency, including paper, tissue paper, plastic and metal |
| 47. | Coatings or direct incorporation in sporting goods such as handles for rackets and bats used in various sports, golf clubs, golf balls, fishing rods and exercise machines. Other sporting goods such as balls for various sports including bowling balls |
| 48. | Foams (flexible and rigid) |
| 49. | Molded and extruded products, including waste containers, devices, tubing, films, bags, packaging (including food packaging), liners gaskets and foam products. |
| 50. | Adhesives (includes caulking materials), gaskets thermosetting materials and composites |
| 51. | Disinfectants for agricultural and food use to kill microbes and prevent their growth on crops, algae control, control of mollusks, insecticide, treatments for meat, vegetables, and fruit. |
| 52. | Biocides to treat water bodies, liquid wastes, industrial processes, hydraulic fracturing fluids, treatment of oil and gas wells, coatings for proppants which contain antimicrobial agents, and their use in other aspects of petroleum industry |
| 53. | Products for pets - toys, treats, food |
| 54. | Printing inks, both for conventional and 3-D printing |

The compositions of this invention may be incorporated in liquid or solid carriers to yield products with antimicrobial properties. Many such examples and methods of incorporation will be discussed below.

Incorporation of the functionalized particles of the invention in molded and extruded thermoplastic products is typically achieved by first making masterbatches, wherein the functionalized antimicrobial compound (or particles infused in porous matrices) are present in relatively high concentrations in polymeric matrices (preferably 1 to 15% of metal by weight (present as metal compound)). The masterbatches are then compounded with the polymer (resin) to make the molded or extruded product. This is typically done by first functionalizing the antimicrobial particles with agents which are compatible with the matrix resins. The functionalized particles are formed in a dry state by removing water or any other solvents which are used in their preparation and mixing them with the desired resins, usually on a mill or a twin screw extruder so that these mix intimately to have a high concentration of the antimicrobial compound. As noted above, this is called a "masterbatch." This masterbatch is typically produced by companies which specialize in homogenously blending the two together and deliver their products as pulverized powders or pellets.

The masterbatches are then used as additives to the matrix resins by processors who use molding and/or extrusion operations to make products. Such plastic processing operations include injection molding, injection blow molding, reaction injection molding, blown film processing, blow molding, rotational molding, calendaring, melt casting, thermoforming, rotational molding and multishot molding. Starting with the antimicrobial concentration in a masterbatch as cited above, the processors use a typical ratio of resin to masterbatch material of 10:1 to about 25:1 or so, which will then result in end products with concentrations of antimicrobial materials of about 0.02 to 1% (based on metallic concentration). Typically for metal halides, these weight fractions are expressed in terms of the weight of the cations only.

To protect the health and safety of the workers employed in such a facility or other downstream processor, it is important to minimize the possibility of getting the nanoparticles airborne. An effective method of accomplishing this involves making the particle size of the dried powders containing the antimicrobial particles relatively large compared with the size of the individual nanoparticles. The size of the dried powders should be greater than 1 micron, preferably greater than 10 microns, and most preferably greater than 100 microns. Such dry powders are easily handled and transported for downstream operators to use in paints, resins and other liquid carriers to create coatings or objects incorporating the functionalized nanoparticles.

The masterbatch can be blended with the neat resin using processing equipment such as injection molding or extrusion machines, which makes the final product. The final products can be a variety of molded products extruded products (including tubes, bottles, fibers for use in fabrics/textiles and carpets). In some materials presence of copper iodide particles may lead to issues related to color fastness. For these one may add additional stabilizers. For example, halide salts (e.g., potassium iodide, see U.S. Pat. No. 4,745,006 and Janssen K. et al, Polymer Degradation and Stability, Vol 49, p 127-133 (1995)) may be added in 5 to 10 times in excess of the iodine provided by copper iodide.

Antimicrobial compositions of this invention may be added to extruded or molded polymer products homogeneously or may be applied to these objects as coating layers using operations such as extrusion or molding. In the latter case, operations such as co-extrusion, in-mold decoration, in-mold coating, multi-shot molding, etc are used where the antimicrobial additive is only present in that resin/material which forms the skin of the product as a result of these operations.

The functionalized microparticles and nanoparticles of the present invention may also be used by combining them with monomeric compositions or with solutions of preformed polymers, where the resulting materials containing the functionalized particles may be used to create two- and three-dimensional objects, adhesives and coatings, where the compositions are polymerized or crosslinked or densified after processing/setting the compositions into their final form. Coatings may also be deposited from solutions and aqueous polymeric emulsions containing the functionalized antimicrobial particles, where the formulations preferably comprise one or more film-forming polymers, or the particles may be employed in powder-coat formulations which are then processed into coatings.

Antimicrobial inks comprising functionalized particles of this invention may be formed using techniques known in the art of printing inks Such inks may be printed using a variety of techniques such as inkjet, flexo, gravure and silk-screening. In some cases, such as in inkjet printing, the size of the functionalized particles should be smaller than about 50 nm. Three dimensional antimicrobial products may be formed by 3-D printing, where the inks incorporate the antimicrobial materials of this invention.

Water based acrylic, epoxy and urethane paints are used in many applications. These are typically emulsions of hydrophobic polymers in water. After application to a surface, the water evaporates and the emulsions coalesce leaving a hydrophobic coating. In order to impart antimicrobial properties to these coatings, one can take these emulsions (preferably before fillers are added) and grind the antimicrobial particles in their presence to produce antimicrobial particles functionalized by these emulsions. The antimicrobial material can be in high concentration and such concentrates may be added to the paint formulations to provide antimicrobial properties to the coated objects. Alternatively, one may also grind the antimicrobial material with a compatible functionalizing agent (such as a surfactant) which may even be the same as the surfactant used as an emulsifier in the paint, and then such powder can be added to the paints. In yet another method, porous carrier particles with antimicrobial particles therein can be produced, which are then added to the paint formulations.

As another specific example, these methods may be used to incorporate particles of this innovation in formulations of nail polish (a coating application), which are available as water or solvent based. Typical solvents used in nail polish are acetates (e.g., butyl acetate). The particles may be ground with using solutions of the polymers and/or surfactants which are used in these applications and are then added to the final nail polish composition. Since the final compositions are quite viscous, it is often desirable to grind the particles separately as suggested above, or the complete nail polish formulation with excess solvent may be used as the liquid medium, and the excess solvent is removed later. While these nail polishes can provide protection by preventing microbial growth, such nail treatments may also be used to actively treat nail fungal infections. Nail polish products include formulations which are used for base coat or a top coat in the nail polish industry. Antimicrobial additives in base coat are particularly desirable to protect fungal or other microbes from one person to be transferred to another person particularly in nail salons. Antimicrobial additives to top coats will prevent any microbe harboring on the surface which may grow and get transferred to others during contact, etc. Nail polish products which may have higher water permeability (or breathability in excess of about 0.4 mg of water/$cm^2$-hr), may be more prone to bacterial infections, and addition of antimicrobial agents and particularly those of this invention would be highly beneficial in keeping the nails microbe resistant. There are many products in the market offering nail polishes with high water permeability. Some examples are are O2M line of enamels from Inglot Sp. Zo.o. (Poland), Acquarella nail polishes from Acquarella LLC (Tucson, Ariz.).

When used in coatings and molded and other three dimensional products, the particles may scatter light, depending on their concentration, size and refractive index relative to the matrix. This can give rise to opacity or haze with increasing product thickness, larger particles, higher particulate concentrations and larger differences between the refractive index (RI) of the particles and the matrix. In many applications, this is not an issue, since the products contain other opacifiers such as titanium dioxide. In other cases, e.g., for optical and ophthalmic products, or products where coatings should not interfere with the appearance of the substrates, optical clarity is important. One may use the materials of the present invention provided the above-cited parameters are controlled. The RI of most common polymers is in the range of 1.4 to 1.6. Silicones will be closer to 1.4, acrylics closer to 1.5 and polycarbonate closer to 1.6. By comparison, the RI of copper iodide (as an example) is 2.35. For high clarity (or low haze, typically less than 2% haze (preferably less than 1% haze and more preferably less than 0.5% haze) in the visible wavelengths as measured by ASTM test method D1003), it is preferred that the average size of CuI particles be less than about 200 nm (preferably less than about 120 nm), volume loading less than about 2% (preferably less than about 1%) and product thickness less than about 0.25 mm (preferably less than about 0.1 mm). AgI, AgBr, CuBr, CuCl and $Cu_2O$ have lower refractive indices compared with that of CuI and will allow relaxation of these numbers (meaning larger particle sizes, higher volume loading and thicker products in products of high clarity). However, some of these materials with lower refractive index may impart stronger colors which may be undesirable.

Functionalized antimicrobial particles may be produced in aqueous media (e.g., by grinding or the other described processes) and added to the leather tanning solutions. When leather is soaked in these solutions and later dried, it will retain the antimicrobial particles which will result in antimicrobial leather. In carrying out this process, the leather may be soaked in the antimicrobial solutions after fats and oils have been removed and washed or may be incorporated within the tanning solution.

As yet another example, one may also produce antimicrobial foams which are used for a number of applications. For example, polyurethane foams are made using a formulation produced by mixing an isocyanate with a polyol (a molecule with three or more hydroxyl groups) a chain extender (a bifunctional hydroxyl molecule), catalysts to promote reaction, surfactant, heat and/or UV stabilizers along with a foaming agent. The foaming agent could be water as it produces carbon dioxide gas when it reacts with the isocyanate. One method of making antimicrobial foams involves producing antimicrobial particles with a surfactant (using a surfactant compatible with the system or the same which is used in the system) or one of the urethane-forming constituents and adding these to the foam formulation. Another alternative involves producing nanoparticles in an aqueous media, such as by grinding them in water along with the desired surfactant and then adding this aqueous mixture to the foam formulation both as a foaming agent and as an antimicrobial source.

Another method by which they may be added to solid carriers is by grinding the antimicrobial materials in liquid plasticizers. As an example, phthalate ester plasticizers may be used as a liquid medium for grinding the antimicrobial material in the presence of a functionalizing agent, and when such ground compositions are added to plasticize polyvinylchloride (PVC), than the resulting plasticized PVC acquires antimicrobial properties. Alternatively, one may also grind the antimicrobial material with a compatible surface functionalizing agent (such as a surfactant) which is then added to the plasticizer before incorporating this mixture into the polymer.

Imparting a thin coating to a surface allows one to obtain antimicrobial properties on a surface without infusing the potentially expensive materials into the bulk of the object. As an example, powder coatings with the antimicrobial additives of this invention can be formed on metals, and even on non conductive surfaces such as wood, ceramics and other polymers (thermoplastics and thermosets). The technology for powder coating of materials is well established (e.g., see "A Guide to High Performance Powder Coating" by Bob Utec, Society of Manufacturing Engineers, Dearborn, Mich. (2002).) The matrices for powder coats are typically epoxies for indoor use where high chemical resistance is required and acrylics and polyesters including epoxy-polyester hybrids for outdoor use where superior UV resistance is needed. In typical powder coating operations, the object to be coated is suspended in a fluidized bed or subject to an electrostatic spray so that particles flowing past this object may stick on its surface (where the particles contact and melt due to higher surface temperature or the particles are attracted due to the static attraction and melted later). Typically, the powders melt and then cure forming a coating. The coating processing temperatures are typically in the range of about 80 to 200° C. In the past, mainly metals were coated with polymeric powders. Recently, however, increasing use is being made of polyurethane powders for coating objects made of thermoset polymers and acrylic powders for coating thermoplastics objects (including acrylics which are cured using UV after the coating is deposited).

To produce powder coatings, one may prepare powders of functionalized antimicrobial particles or incorporate antimicrobial particles in porous materials (such as porous silica) and then dry blend with powder coating resins. Other ingredients such as crosslinking agents, degassers (defoamers) and flow additives may also be added to this blend, which is then mixed in an extruder where the resin melts and is the composition is extruded, and the material pulverized to form a powder. This powder is then used to coat the objects (e.g., by a corona gun) and then heat treated to fuse the powder on the substrates which results in an antimicrobial coating.

The materials of the present invention may also be incorporated in anodized coatings to provide antimicrobial characteristics in addition to the wear and corrosion resistance which these coatings impart to the surfaces. Anodization is used to coat/treat many metals and is most often used for magnesium, aluminum and their alloys. Anodization is an electrochemical process, wherein the metal object or substrate is cleaned and placed in the electrochemical bath, which is typically acidic. There are several variations where organic or inorganic acids are used for this purpose and are well known in the art. The typical thickness of anodized layers is in the range of 0.5 to 150 μm. One method to incorporate the antimicrobial materials of this invention involves treating the anodized objects with solutions of functionalized nanoparticles of the antimicrobial agent so that they can penetrate the porous structure of the anodized layers and get trapped in the interiors (anodized coatings are usually porous with a pore size of 5 to 150 nm). Another method involves incorporating the functionalized antimicrobial particles during the process of anodization. In this process, the antimicrobial nanoparticles are typically functionalized with acids or even acidic polymers such as polystyrene sulfonic acid and then such functionalized particles are added to the anodization bath. Such functionalization imparts negative zeta potential to the particles so that they have sufficient mobility in the applied field towards the anode and get incorporated within the anodized coatings as these coatings form on the surfaces of the objects being anodized.

Other embodiments of products formed from the antimicrobial compositions of the present invention include topical creams for both pharmaceutical and consumer product use (e.g., personal care products). They can impart one or both of antimicrobial and preservative properties. As a specific example, functionalized particles may be added to/formulated with Carbopol® polymers from Lubrizol to produce gels and creams which may be used as antimicrobial creams for treatment of bacterial and fungal infections, wounds, acne, burns, etc. Although any concentration of the functionalized nanoparticles may be used which provides effective treatment, a useful range of metal concentration (from the surface functionalized particles) in the finished product is 10 to 50,000 ppm. The precise concentration of any particular topical treatment can be assessed by testing the cream in any of the assays for antimicrobial effect presented herein, or known to one of ordinary skill.

The functionalized antimicrobial particles may also be formulated in petroleum jelly to provide superior water resistance. One may use additional surfactants and compatibilizers so that while the hydrophobic petroleum jelly protects the application area, it is also able to release the antimicrobial material to the underlying areas which may be hydrophilic. One of ordinary skill in the pharmaceutical art of compounding will know how to create antimicrobially active creams and ointments in combination with the functionalized metal halide powders of the present invention. As an example, one may formulate the materials using PVP/Polyolefin copolymer as functionalization agents which are available from Ashland (New Milford, Conn.) as Ganex® WP-660, Ganex® V-516 and Ganex® P904LC with various levels of olefinic content and hydrophobicity. One may optionally add hydrophobic esters for the reasons as described earlier, some examples are ascorbic acid palmitate and lauryl gallate.

One may also fabricate antimicrobial sutures and wound dressings (including burn dressings) using the materials of the present invention. Dressings consisting of gauze (textiles) or foams or sutures may be made by incorporating the functionalized antimicrobial particles of this invention into the constituent fibers or materials of these dressings or sutures. Antimicrobial dressings may also be formed by soaking gauze, fabrics and foams in aqueous solutions containing functionalized particles and a hydrophillic polymer (e.g., PVP, carboxy methyl cellulose, etc.). For those dressings which use cuprous salts, additives to keep cuprous ions from oxidizing are also preferred. The wound dressings may be formed by laminating various layers where each layer provides different functions. In some cases only some of the layers contain antimicrobial agents. The feel or the drape of the dressings and their adhesion properties to the wounds may be modified by adding non-toxic surfactants, glycols, fatty acids and oils, etc. to the solution compositions. These dressing may have other medications or additives also incorporated in them (e.g., analgesics) in a post treatment or by adding them to the same solution which contains the antimicrobial particles. Additives also include iron sequestering agents so that they would reduce the availability of iron for bacteria to grow and produce biofilms. Some of these agents are phosphates with preferential sequestering of iron, glycol proteins such as ovotransferrin, lactoferrin and sertotransferrin. Additives may also include more water soluble salts to provide immediate release, of antimicrobial anions or cations or both, e.g., these salts may be $CuCl_2$, $AgNO_3$, KI, NaI, etc. The additives may further include materials compatible with the mucus agents which form the biofilms, so as to help with the transport of the antimicrobial materials through these biofilms to deliver the antimicrobial agent to the surfaces of the bacteria or spores.

Examples of some materials with such characteristics include glucose and xylitol. In addition these materials are also known to stabilize the oxidation state of metal (e.g., $Cu^+$) ion. These may be also incorporated as functionalizing agents. To make wound dressings with broader efficacy, one may combine more than one type of metal salt or use solid solutions of metal salts. For example, some preferred combinations are CuI with AgBr, CuI with AgCl and CuI with AgI. These dressings may have several components as discussed above in order to provide antimicrobial properties and other wound management attributes, some additional components are discussed below, such as water soluble halide salts. These dressing may be a part of one or more of the layers of a flexible multilayer wound dressing laminate, wherein preferably the layer in contact with or close to the wound contains the antimicrobial material.

Another embodiment of the functionalized metal halide particles is directed to an antimicrobial composition for wound management, comprising a povidone-iodine solution and at least one type of functionalized antimicrobial particle having an average size of from about 1000 nm to about 4 nm. A further embodiment of the povidone-iodine solution is wherein the antimicrobial particle is selected from the group consisting of copper halide and silver halide, and a further embodiment comprises halides selected from the group consisting of iodide, chloride and bromide, and a still further embodiment comprises CuI. The povidone-iodine compositions of the present invention may also be used to treat animals or humans to treat infected topical areas. As one example, aqueous topical solutions of PVP and iodine (where iodine is about 8 to 12% by weight of the PVP) are commonly used as disinfectants for wounds and for disinfecting skin prior to surgery. BETADINE® is a commercially available PVP-iodine solution. Povidone-iodine (PVP-I) is a stable chemical complex of PVP and elemental iodine. 10% solutions in water are commonly used as a topical antiseptic. One may add the functionalized antimicrobial particles of the present invention (such as AgI and/or CuI particles functionalized with PVP) to such PVP-iodine solutions to obtain new disinfectant solutions with notably enhanced disinfecting ability. Compositions of metal halide particles added to such PVP-I solutions also come within the scope of the current invention. Such a metal halide-enhanced PVP-I solution would be formulated having about 88-99% PVP, 2 to 10% Iodine, and 0.005-10% metal halide particles on a wt/wt basis. One may also add additional water soluble halides such as KI, NaI, LiI to the antimicrobial formulations, and their typical molar concentration ratio is about 0.001 to 0.1 as compared to concentration (molar) of the metal halides in the formulation. One method to make such compositions is by wet-grinding the metal halide(s) in PVP-I solution for surface functionalization of the particles being ground, where we have found that while grinding CuI, NaI functions as a grinding aid in presence of PVP, and thus it is preferred that this be added before or during the grinding operation. These weight proportions are relative to these three components excluding water and other solvents.

For wound management (creams and dressings) the functionalized particle compositions may comprise additional additives. These additives are helpful in maintaining pH (buffers to control pH in the range of 4 to 7) and also increase the efficacy of such compositions. The preferred additives are reducing agents (antioxidants) such as organic acids, aldehydes, alcohols and their salts. Some of the preferred acids and their salts are citric acid, ascorbic acid, cinnamic acid, hyaluronic acid, salts of these acids, and preferably lithium, sodium, potassium, calcium, copper and silver salts of these acids. Some acids which have several groups may be converted to the salts by substituting one or more of these groups. As an example, citric acid can be converted to sodium citrate by reaction with a sodium-containing base. In this way one can form monosodium, disodium and trisodium citrates or their mixtures. Any of these may be used, but trisodium citrate is preferred for wound dressings and creams when used with functionalized metal halide particles, particularly copper and silver halides. A preferred functionalization for these halide particles are polymers used in conjunction with soluble halide salts (such as LiI, NaI and KI). The preferred polymers are those with mildly reducing properties such as PVP, copolymers containing PVP (i.e., copolymers containing vinyl pyrrolidone groups) and carboxy methyl cellulose.

The antimicrobial materials of this invention may also be used as additives to other drug formulations including other antibiotic creams or formulations for infection control or related purposes. The antimicrobial materials of this invention may be added in a burn cream, which while assisting the repair of burned tissue will also keep infection away, or it may be mixed with other antibiotics, infection reducing/prevention analgesic materials such as bacitracin, neomycin, polymyxin, silver sulfadiazine, polyenes, selenium sulfide, zinc pyrithione and paramoxine, Many of these compositions listed above are available in commercial products, and the antimicrobial materials of this invention can be added to them to result in a concentration that is most effective.

The compositions of the present invention can also contain any combination of additional medicinal compounds. Such medicinal compounds include, but are not limited to, antimicrobials, antibiotics, antifungal agents, antiviral agents, anti thrombogenic agents, anesthetics, anti-inflammatory agents, analgesics, anticancer agents, vasodilation substances, wound healing agents, angiogenic agents, angiostatic agents, immune boosting agents, growth factors, and other biological agents. Suitable antimicrobial agents include, but are not limited to, elemental iodine, biguanide compounds, such as chlorhexidine and its salts; triclosan; penicillins; tetracyclines; aminoglycosides, such as gentamicin and Tobramycin™; polymyxins; rifampicins; bacitracins; erythromycins; vancomycins; neomycins; chloramphenicols; miconazole; quinolones, such as oxolinic acid, norfloxacin, nalidixic acid, pefloxacin, enoxacin, and ciprofloxacin; sulfonamides; nonoxynol 9; fusidic acid; cephalosporins; and combinations of such compounds and similar compounds. The additional antimicrobial compounds provide for enhanced antimicrobial activity. Some of these may be treat humans or animals as a whole (e.g., by oral administration, injection, etc).

Several antimicrobial treatments may require use of sprays (e.g., aerosol spray-on bandages or topical treatments of infections), or even spray-on paints and household cleaners. In many of these cases, it is not desirable to have very small functionalized particles present in these compositions, since during the spray operation, many of the particles could become airborne and enter the human airways. There are several ways of overcoming this while using the antimicrobial materials of the current invention in the nanoparticle form. One method is to form clusters of functionalized nanoparticles typically larger than 1 micron which keep their togetherness by using a binder which does not allow the nanoparticles to come apart in the spray solvent, For example, the binder may be water soluble while the solvent for the spray (e.g., dimethyl ether, $CF_3CHF_2$, $CF_3CH_2F$) would be a non-solvent for the binder and would keep the clusters intact. Another method involves infusing the particles in non-ion exchange porous particles which are greater than about 1 micron in size (as discussed in an earlier section) and incorporate these particles in the aerosol medium. Yet another method uses particles which are greater than 100 nm in size.

In cases where it is desired to use functionalized antimicrobial particles in the treatment of lung infections, it is preferred to employ particles with substantial water solubility combined with water-soluble functionalizing agents. In this way, aerosols can be prepared using a nebulizer and delivered to the patient's lungs to provide the desired high dose of antimicrobial activity, and over reasonable periods of time the particles will be eliminated by dissolution. In cases where deep penetration of the antimicrobial agent into the airways is desired, use of small nano-sized particles may be desirable.

Other embodiments of the present invention comprise medical devices that are rendered antimicrobial using methods comprising contacting the surfaces of the devices with the functionalized salt compositions of the invention. Medical devices, without limitation, include catheters (venous, urinary, Foley or pain management, long dwell catheters or variations thereof), stents, abdominal plugs, pacemakers, hearing aids, masks (including ventilators), cotton gauzes, fibrous wound dressings (sheet and rope made of alginates, CMC or mixtures thereof, crosslinked or uncrosslinked cellulose), collagen or protein matrices, hemostatic materials, adhesive films, contact lenses, lens cases, containers for cleaning solutions, bandages, sutures, hernia meshes, mesh based wound coverings, ostomy and other wound products, breast implants, hydrogels, creams, lotions, gels (water based or oil based), emulsions, liposomes, ointments, adhesives, porous inorganic supports such as silica or titania and those described in U.S. Pat. No. 4,906,466, the patent incorporated herein in its entirety by reference, chitosan or chitin powders, metal based orthopedic implants, metal screws and plates etc.

The compositions of this invention may be added into the resin from which the products are made and then extruding or molding these objects, or they may be added as coatings. One may prepare the antimicrobial functionalized metal salt particles by any one of the disclosed methods, and then redisperse them in a liquid medium and apply them to the desired substrate. Alternatively, as discussed in an earlier section, one may use solutions of metal salts such as metal halides with functionalizing agents to form coatings or impregnate objects such as wound dressings.

The compositions of this invention may also be used for tooth restoration. These include applications such as dental adhesives, primers, sealants and composite fillings and products such as dentures (including antimicrobial solutions to treat dentures), crowns, bridges and coatings including coatings on implants. The methods of incorporating the antimicrobial agents of this invention in solutions, sealants/adhesives and coatings for dental applications are very similar to those employed for other applications discussed throughout this patent application. As an example, in several dental sealants and adhesives the surfaces bonded are dentin while in some others these are enamels. It is important for the antimicrobial materials which contact the dentins are biocompatible with such surfaces. Some of the standard materials used in restorative composites are UV cured resins comprising methyl methacrylate, 2-hydroxyethyl methacrylate urethane dimethacrylate oligomer, bisphenol A-glycidyl methacrylate. triethyleneglycol methacrylate, ethyleneglycol dimethacrylate and silanes are also used for adhesion promotion. One may use particles of this invention where the functionalization agents are chosen from the above materials, as an additive to the dental compositions. Alternatively porous particles formulations as discussed earlier may also be used.

Yet another application of these materials involves the production of household and industrial disinfectants. Depending on the composition of the disinfectants, they may provide a rapid kill when these contact or are sprayed onto surfaces. After wiping the treated surfaces, the disinfectants may be formulated to leave a residue which will provide continuing protection against microbes which subsequently contact the surface.

Rapid kill is typically less than 5 minutes, preferably less than two minutes and most preferably 30 seconds or less. This is achieved by including in the formulation components in a concentration which kill microbes rapidly. Many of these components may be combined to produce synergistic effects, while keeping the concentration of each of these low. Such components typically result in a rapid change in pH, hydration or damage to the protective microbe membrane. These include acids such as acetic acid, citric acid, alcohols and ethers such as isopropanol, ethanol and propylene glycol monobutyl ether, quaternary ammonium cations including silanized versions, water soluble salts of active cations such as silver and copper, and certain functionalized particles of this invention. Long-time protection is typically greater than two hours, preferably greater than 24 hours and most preferably greater than 1 week. Such long term protection is provided by formulating the disinfectants with appropriate concentrations of functionalized particles together with a film-forming polymer or polymers.

The preferred disinfectant formulations are aqueous based, with a pH in the range of about 2 to 7. The pH may be controlled by acids and buffering materials. Some of the preferred acids and their salts are acetic acid, citric acid, ascorbic acid and cinnamic acid and salts of these acids for buffer control. Some of the preferred salts are lithium, sodium, potassium, calcium, copper and silver salts of these acids. Particularly preferred acids include acetic acid and citric acid. Particularly preferred salts include sodium and potassium salts of these acids.

The disinfectants may also include surfactants, alcohols, and ethers to clean fatty residues from the surfaces to which they are applied and also to provide better wetting of the surfaces (e.g., isopropanol, ethylene glycol monohexyl ether, sodium lauryl sulfate, etc.). These materials may also be used as functionalizing agents.

The film forming polymers used in the disinfectant formulations include PVP, copolymers comprising PVP, chitosan, ionic polymers (e.g., anionic polymers comprising carboxylic or sulfonic acid groups and their salts where the protons are substituted by lithium, sodium, potassium, etc). These polymers may be used both as functionalization agents and as film formers. The resulting films maintain a fraction of the antimicrobial particles trapped in the coatings on the surfaces after the liquid carrier has evaporated. Examples of other additives are viscosity modifiers, soluble salts, fragrances, colorants and compounds to promote antimicrobial ion stability.

As another example, the compositions of this invention may be included in hair care products or other body care (personal care) products such as antidandruff shampoos, body washes, deodorants, nail polish and moisturizing and other creams. In such cases, one may grind the particles using the matrix compositions of the respective formulations as the grinding fluids. One may also carry out the grinding in a different medium (e.g., an aqueous medium containing a surfactant, dispersant or a polymer used in the product formulation), and adding these suspensions to the end products.

Yet as another example, pet products such as toys, treats (e.g. chews) and food items (e.g. kibbles) may have the antibacterial compositions of this invention coated or infused within these products. Many of these products are recalled for bacterial infection, particularly Salmonella. As a specific example, many pet chews are made from animal hide or pig ears. These products are processed by washing hides/pig ears in hot water and then shaping and drying them at about 80 to 90 C for a period of about 20 to 48 hours. Although the hot water baths and drying procedures are expected to kill many of the bacteria, it is possible that some spores may survive or the product surfaces pick up infection from surfaces they contact in post processing operations. One treatment method comprises adding the compositions of this invention in the last aqueous bath so that these infuse into the products before they are dried. Alternatively these products may also be sprayed with the present antimicrobial compositions. Such treatments will not only kill residual bacteria, but also stop bacterial colonies from growing if the product surfaces are later come in contact with microbial contamination. When using functionalized copper salt particles, their concentration in the bath could be any; but a preferred range is about 1 to 500 ppm (measured as copper concentration). It is further preferred that the overall copper salt (e.g. CuI) concentration in a chew or a food product is typically less than 0.01% by weight, although the surfaces of these products may have higher concentrations. When functionalized metal salt particles are used some of the preferred functionalization agents include amino acids, carbohydrates and PVP. The functionalized antimicrobial particles of the present invention can also be added to baste formulations used in manufacturing pet products, so that coatings of these on the pet products also provide benefit of antimicrobial protection in addition to other attributes. For incorporating the disclosed materials in polymers used either for packaging or in pet toys one can follow the methods used for as discussed earlier for bulk polymers where masterbatches were discussed.

Also contemplated by the present invention are antimicrobial fabrics (including carpets), such as those based on synthetic fibers, e.g., nylon, acrylics, urethane, polyesters, polyolefins, rayon, acetate; natural fiber materials (silk, rayon, wool, cotton, jute, hemp or bamboo) or blends of any of these fibers. The fibers or yarns may be impregnated with suspensions of the functionalized antimicrobial particles, or for synthetic fibers the functionalized nanoparticles may be incorporated into resin melts/solutions (e.g., using the masterbatch approach discussed earlier) that are used to form the fibers. In an alternative embodiment, the fabrics may be provided with coatings containing the antimicrobial compositions of the present invention. Devices, medical including dental and veterinary products and non-medical, made of silicone, polyurethanes, polyamides, acrylates, ceramics etc., and other thermoplastic materials used in the medical device industry and impregnated with functionalized particles using liquid compositions of the present invention are encompassed by the present invention.

Various coating compositions for different polymeric, ceramic glass or metal surfaces that can be prepared from liquid compositions are also contemplated by the present invention, as are coating compositions which are impregnated with functionalized antimicrobial particles after their deposition. Metal alkoxides and other metal oxide precursors (e.g., metallo-organic, water soluble silicate, aluminate, titanate and zirconate, mixed metal precursors such as alkoxy aluminum silicates, etc) may be used to form porous ceramic/glass coatings. In one embodiment, the antimicrobial metal salts functionalized by metal oxide precursors (including porous particles of metal oxides with infused metal salts) may be added to coating solutions formed by metal oxide precursors. In some cases both the precursor used for functionalization and for forming the coating may be similar for enhanced compatibility. The coating compositions deposited from liquid solutions can be hardened by solvent loss or cured by thermal or radiation exposure or by incorporation of polymerization (e.g., cross-linking) agents in the coating formulations. The resulting coatings may be hydrophobic, oleophobic (or lipophobic) or hydrophilic. The oleophobic coatings are typically used on display screens, particularly touch screens and imparting of an antimicrobial character to such surfaces can be valuable. Further for touch screens the coatings should be transparent and abrasion resistant.

Antimicrobial medical and non-medical devices of the present invention can be made by treating the devices with the functionalized metal salt compositions of the present invention by different methods. One disclosed method of the present invention comprises the steps of making the compositions in a dry particulate form that may be redispersed in an aqueous or nonaqueous carrier liquid, then contacting the compositions and the device surfaces for a sufficient period of time to allow accumulation of particles and then rinsing the excess of said composition away and drying the device. A modification of the disclosed method may involve drying or curing the surface of material first and then rinsing off the surface to remove excess. The method of contact may be dipping the device in the compositions or spraying the compositions on the device or coating blends of polymer solution and the compositions.

In other cases, the functionalized antimicrobial particles or porous particles containing antimicrobial compounds may be incorporated in polymer-based coating solutions from which antimicrobial coatings are deposited by end users. For example, the compositions of the invention may be applied to marine surfaces as a bactericidal agent. As another example, the compositions of the invention may be incorporated in polyurethane coating solutions and applied to furniture or flooring by the end users.

In another aspect, the present invention provides methods and compositions for applying antifouling coatings to an article such as a boat hull, aquaculture net, or other surface in constant contact with a marine environment. Materials that are immersed for long periods of time in fresh or marine water are commonly fouled by the growth of microscopic and macroscopic organisms. The accumulation of these organisms is unsightly and in many instances interferes with function. The natural process of accumulated growth is often referred to as fouling of the surface. There are a number of agents that may be applied to the surfaces to inhibit this growth, and may usefully be combined with the materials of this invention. These agents are known in the art as antifouling agents. While many of these agents are highly effective, some of them may be toxic that often leech from the surface of the article and accumulate in the local environment. In one embodiment, the present invention provides a composition for treating a marine surface comprising a particle having at least one inorganic copper salt, and at least one functionalizing agent in contact with the particle, the functionalizing agent stabilizing the particle in suspension such that an amount of ions are released into the environment of a microbe sufficient to prevent its proliferation.

Another application of the present inventions involves stopping the proliferation of microorganisms and the resultant formation of slime (biofilm) in "aqueous systems". The materials of this invention are particularly effective when the pH is acidic or has reducing characteristics, or alternatively the metal halide particles are functionalized with such materials and then incorporated in coatings or in bulk. The microbes of concern include bacteria, fungi, and algae. The relevant "aqueous systems" include both industrial and residential applications. Examples of these application include water cooling systems (cooling towers), pulp and paper mill systems, petroleum (oil and gas) operations, water and slurry transportation and storage, recreational water systems, air washer systems, decorative fountains, food, beverage, and industrial process pasteurizers, desalination systems, gas scrubber systems, latex systems, industrial lubricants, cutting fluids, etc.

In petroleum applications, particularly in oil and gas extraction, transportation, storage and further processing (i.e., collectively called petroleum extraction industry), antimicrobial materials (or biocides) of this invention may be used in a number of areas, some of these are:

1. Drilling, completion and workover fluids.
2. Fracturing (fracking) fluids.
3. Coatings on proppants used during fracking
4. Flood and injection water during production of oil and gas.
5. Pipelines, tank flush, pipeline pigging and scraping and packer fluids (maintenance).
6. Coatings for pipelines (including transmission pipelines) and storage tanks
7. Molded and coated components such as valves, lids, actuators, gauges, sensors, etc., which come in contact with oil and gas.
8. Incorporated into the cements used for the wells.

Injection fluids are also used to deliver biocides in the wells on a regular basis (e.g. daily or a weekly) in order to control bacteria, corrosion and formation of slimes due to bacterial growth in these wells.

The bacteria of concern may be aerobic (e.g., *Pseudomonas aeruginosa* and *Staph. aureus*) or anaerobic (e.g., sulfate reducing bacteria (SRB) and acid producing bacteria (APB)). Generally one finds mixtures of bacteria and biofilms of multi-species bacteria in oil wells including, heterotrophic bacteria as well as SRB and APB. Anaerobic bacteria are also found in various waste water streams. Thus the antimicrobial compositions of the present invention may also be used in the waste processing industry where waste water is collected or processed.

The biocides should be compatible with the other additives which are included in the fluid compositions. Some of the additives used in fluids for this application besides biocides such as gluteraldehyde and quat include scale and corrosion inhibitors (e.g., ethylene glycol), viscosity modifiers (e.g., polyacrylamide), emulsion breakers (e.g., ammonium persulfate), acids to dissolve minerals (e.g., hydrochloric acid), organic acids to avoid iron precipitation so as to reduce scale formation (e.g., citric acid), gelling agents (e.g., guar gum), clay stabilizers (e.g., potassium chloride), oxygen scavengers (e.g., ammonium bisulfate), pH control agents (e.g., carbonates of potassium and sodium), proppants (e.g. sand) and surfactants (e.g. sodium lauryl sulfate, isoproanol).

The functionalized particles of this invention may be used as a total or partial replacements of the biocides used in the fluids in order to lower the toxicity of the fluids, and still provide superior antimicrobial properties. It is highly preferred that such particles are pre-formed and added to these fluids and remain in particulate form in the fluids at the time of injection. In order to increase the compatibility of the functionalized particles with these fluids, one may use one or more of the components already present in the fluid as functionalization agents—e.g., polyacrylamide, organic acids such as formic acid, acetic acid, citric acid, salts and esters of these acids, and also aldehydes such as gluteraldehyde, cinnamonaldehyde, ethylene glycol, surfactants, etc.

The fluid compositions (including biocide chemistry and concentration) are customized depending upon the geographic location of the well, type of operation and the function being carried out at that time. This is due to different types of bacteria which may be present there; and whether the bacteria need to be killed in planktonic form or already exist in biofilm form; the speed at which the antimicrobial action is desired (minutes, hours, days, etc); geological composition; and the type of water being used. For example, one may use sea-water or fresh water; and the desired characteristics of the biocide may be different for a hydrofracking operation where a relatively rapid biocidal action is desired, vs. periodic biocide treatment of a well where a slower but a longer lasting biocidal action is desired.

When particles of the present invention are employed in fluid formulations used for fracking and are present alongside of the proppant particles (also present in these fluids), they provide antibacterial properties over a long period of time by limiting biofouling of the fissures formed in the fracking process. When particles of this invention are used in fluid formulations with proppants, their average particle size should preferably be similar to but somewhat smaller than (as about 10-25% smaller than) the size of the proppants. One may even use more than one size of antimicrobial particles so that these would be trapped at different places in the oil field/well. The particles may also be sized and functionalized so that they are attracted to and transported into the already formed biofilms, and then kill the bacteria in these biofilms. One may also use particles of different sizes and different functionalizing agents so that some of these are designed to kill the bacteria more efficiently in planktonic form and others in biofilm form.

The materials of the present invention when added to such fluids are effective at low metal concentrations; and as discussed above different applications within the petroleum industry may require different concentrations. A preferred range of concentrations expressed as metal concentration of the antimicrobial material is preferably in the range of 1 to 1,000 ppm.

One may also use antimicrobial additives in compositions used to coat pipes, storage tanks, valves, probes (sensors), or used as liners, or other service components in the petroleum extraction industry or other industries where prevention of bacterial biofouling (slime) is important. These single or multilayer coatings and liners may comprise polymeric or glass matrices such as epoxy, polyolefins, urethane, alkyds, acrylic, polyester, silica and silicates. These coatings may be deposited from liquid formulations or may be fusion bonded (powder coatings). In these coatings (or at least in one of the layers of a multilayer coating system), the weight fraction of the active materials (e.g., copper salts) of this invention may be any, and is preferably lower than lower than 5%. The biocides of this invention prevent bacteria from proliferating in wells, pipes, and storage tanks, and specifically control or reduce the formation of bacterial biofilms/slimes on their surfaces. They also prevent the release of foul smelling gases (e.g. hydrogen sulfide) by SRB & the corrosion of ferrous pipes and tanks with the formation of iron sulfide. Thus the addition of the materials of this invention also helps with corrosion control of iron and steels components. The antimicrobial materials may also be incorporated in the bulk of materials (e.g., plastics) used to make components for the industry.

Proppants used in the oil and gas industry are particles of sand and ceramics. Their size typically ranges from several tens of microns to several hundred microns. These are mixed in fracking fluids and get trapped in the cracks and fissures which are produced during fracking. These particles keep the cracks and fissures open and allow the product (gas or/and oil) to be extracted. In many instances the proppants are coated with polymers (resins) to increase their performance. The resin coated proppants (RCPs) increase the crush strengths of the proppants so fissures formed in the rocks stay open for a longer period of time, and also if these proppants even get crushed their debris is contained within the proppant coating and does not block the path for the petroleum fluids. Since bacteria can cause biofilms to form and block these paths, it is advantageous to include antimicrobial materials into the resins used for coating the proppant particles. The proppants are coated prior to their use in the fracking operations, i.e., before the fracking fluids with proppants are introduced into the wells or even before they are mixed with the other fracking fluid ingredients. The most used resins employed for proppant coatings comprise thermosets, and some examples are epoxies, phenolics, silicones, urethanes polyesters, alkyds, their mixtures, etc. These coatings may also contain reinforcing materials such as glass fibers and.or toughening agents. The toughening agents in a crosslinked polymeric matrix is typically incorporated as a second phase present as discrete particles or phase separated domains in the matrix. These domains have a different modulus (e.g., rigid polymeric matrix with a dispersed elastomeric phase). The antimicrobial agents may also be predominantly located within the second phase.

Figure 4:
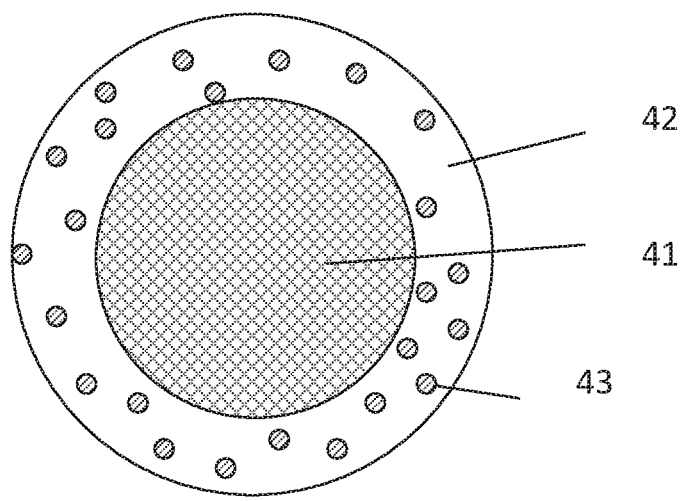
FIG. 4 shows a schematics of a proppant particle with a polymeric coating which has emb

For incorporation in proppant coatings, only some antimicrobial agents are useful. For example, many such agents will react with resin and become permanently bound to the coating. In contrast, the antimicrobial agents of use in the present invention are those which can diffuse out (or whose constituents can diffuse out) of the coating and provide microbe-free regions around the proppant particles for long periods of time. That is, the coatings release an antimicrobially effective active agent (active agent) into the environment of the proppant. Preferred antimicrobial materials are particles which have low water solubility (less than 100 mg/liter or more preferably less than 15 mg/liter at 25° C.) and may be incorporated into the coatings in a particulate form. The particle size (average diameter) of such antimicrobial materials should be less than the thickness of the coating thickness, preferably less than one tenth of the coating thickness. Usually the coatings are several microns thick, and a preferred particle size of the antimicrobial material is less than 1000 nm and preferably less than 300 nm. Further these particles are preferably surface modified (functionalized), and even further the surface modifiers should preferably have a molecular weight of at least 60. FIG. 4 shows schematics of this concept. A proppant particle 41 is coated with a polymeric coating 42 which contains antimicrobial particles 43. This figure shows that the antimicrobial particles are contained within the polymeric coating. The antimicrobial particles may be surface functionalized preformed particles, phase separated domains, porous particles comprising antimicrobial materials, etc. Functionalized preformed particles are the preferred antimicrobial materials for this application.

The antimicrobial agents for coatings on proppants are preferably selected from metal compounds (especially the compounds of the oligodynamic metals (e.g., Cu, Ag, Zn, etc) including metalorganics, but may also comprise organic materials. The most preferred antimicrobial agents are the materials described throughout this specification, i.e., preformed particles of copper and zinc compounds, which are surface modified (functionalized). The use of metal compounds is preferred over metals since the metals are already in the ionic form in the compounds and hence can be more effectively released from the coatings. One may also incorporate the antimicrobial materials in porous particles and then add them to the coating formulations. In this case, the antimicrobial materials may be solids (the typical case) or liquids. In either case, the porous particles readily absorb liquids, which may solidify upon drying, and behave like solids in terms of their handling and incorporating them in the liquid coating formulations. Such porous particles containing antimicrobial materials are described at length in published US Patent Application 20120301533, whose teachings are hereby incorporated by reference.

One may also use zeolitic particles comprising ion exchanged antimicrobial ions such as copper and zinc. The antimicrobial agents from these porous particles are then released in the environment surrounding the proppants once the proppants are deployed in the field.

The current invention whereby antimicrobial materials are incorporated in polymeric coatings on proppants is superior to the approach of depositing antimicrobial particles onto proppant particles or onto coatings on proppant particles. The current approach provides much greater durability of the antimicrobial structure, the ability to tailor the release rate of the active antimicrobial agent, etc. In the present invention, a preferred way of incorporating the antimicrobial materials is to mix them with the the coating formulation (composition) or its constituents prior to the application of the coating to the proppants. The coating formulation also comprises at least one of a polymer or a polymer precursor (monomer). After coating the proppants, the resin is cured or dried to get the RCPs. One may also create encapsulated particles (capsules or particles) comprising antimicrobial agents which are then mixed with the polymers or their precursors and then coated onto the proppant particles. In the oil wells under high pressure and temperature, these capsules will then release the antimicrobial materials or their constituents which will be transported (or diffuse through) the proppant coatings to provide an antimicrobial environment around the proppants.

The amount of antimicrobial additive will depend on several factors, such as cost, diffusion rate through the proppant coating, amount of antimicrobial agent required to create an effective concentration in a region large enough around the proppants, time period over which the biocidal efficacy must be maintained, etc. Considering many of these factors, the antimicrobial agent concentration should preferably be in a range of about 0.05% to 20%, and more preferably in a range of about 0.1 to 5%, most preferably between 0.1 and 3%. Some examples of low water solubility materials other than the compounds discussed elsewhere in this application are zinc pyrithione, selenium sulfide, 5-chloro-2-(2,4-dichlorophenoxy)phenol and 2,3,4,5,6-Pentachlorophenol—(Pentachlorophenol); 2-(Thiocyanomethylthio)benzothiazole—(fungicide, Busan™, Buckman Laboratories, Memphis, Tenn.). In some cases, the antimicrobial materials may be solubilized in the coating formulation, but when the coating is deposited on the proppants and as it dries out or cures, the antimicrobial materials may form a new phase (i.e., phase separate). These phase separated domains may also be considered particles according to this invention. The particles may be solid at room temperature and pressure, and in the oil wells under high temperature and pressure they may change state (e.g., liquefy) and release the antimicrobial component more rapidly.

One may use a mixture of types of antimicrobial materials some of which result in a rapid release when the proppants are put in place in the oil wells, and other(s) release the active agent more slowly with time. One may also incorporate materials which demonstrate antimicrobial characteristics after they contact another material. For example, materials such as n-halamines may be incorporated into the proppant coatings, and when the well is treated with another material, the antimicrobial activity of the particle increases. In case of halamines, if the wells are treated with sodium hypochlorite (i.e., bleach) the proppant would come "activated" for some time. One may also add materials to resin coated proppants which release materials and when these come in contact with the fluid environment around the proppants, they react with at least one ingredient in the environment to produce an antimicrobial agent. One may add several types of antimicrobial agents or even mix them in different forms such as antimicrobial agents as surface functionalized particles and also as same or different antimicrobial agent in porous particles within the same coating.

These compositions, particularly those which comprise CuI can also work as corrosion inhibitors even in the absence of anaerobic bacteria. In the past it has been shown that CuI imparts corrosion resistance to ferrous metals at high temperatures. For example, in U.S. Pat. No. 3,773,465, CuI is combined with an efficient corrosion reducer under highly acidic conditions—e.g., using 15-30% HCl. If other corrosion inhibitors are not included even at use levels of 2.5% or 25,000 ppm of CuI, the treatment is not effective for corrosion control. There is no hint in this patent on any effect of CuI on bacteria. The teachings of this patent are consistent with the general knowledge that "Copper iodide is used in acid muds to bind corrosion inhibitors to the iron drills" (Richardson, Wayne H., Chapter on "Copper compounds" in Uhlmann's encyclopedia of Industrial Chemistry, Vol 9, (2003) p 473-502). It should also be noted that when one adds 1,000 ppm copper as copper iodide (which means 3,000 ppm of copper iodide) to 15 or 30% HCl, a clear liquid is formed. This shows that the CuI has completely solubilized or reacted to form products which are soluble. Thus the addition of CuI particles to highly acidic systems will result in their dissolution, and the injection liquid or the product of manufacture will not comprise functionalized particles.

When large quantities of water are used, the use of such acidic formulations is not practical. Hydraulic fracturing of a single well may require 10 million liters of water (and 10 to 15 such operations may be required during the operation of the well). Even the use of HCl at a concentration of 5% results in a water pH of 1.9, and higher amounts of acid will lead to lower pH's. When large amounts of water are injected, it is important that the toxicity of such aqueous formulations be low, and the pH be above 2, preferably above 4, and more preferably above 5. When using the functionalized particles of the present invention as biocides in petroleum extraction operations the copper concentration the fluids associated with the added CuI particles should preferably be less than about 1,000 ppm, more preferably less than about 150 ppm and most preferably less than 60 ppm. The particles of this invention can be combined with known corrosion inhibitors (e.g., glycols such as ethylene glycol, Mannich reaction products, quaternary amine compounds and their mixture, e.g., also see published US patent application 20110100630); and when this is done, use of the particles of this invention makes it possible to use lower concentration of corrosion inhibitors. One may also use corrosion inhibitors as functionalizing agents.

Applications of the above teachings is not limited in petroleum (oil and gas) industry, as applications encompass various chemical and industrial processes where corrosion and slime formation or health issues due to anerobes or aerobic bacteria is important.

Yet another application of the present invention is to situations where human waste is collected for a period of time before it is disposed—for example, in waste control in portable toilets. Such toilets are extensively used to provide facilities for temporary use such as in construction and other military and civilian activities, and the application also includes toilets used in the transportation industry such as planes, buses, trains, boats, ships and space travel. In these applications, it is important to control microbial proliferation in the tanks holding such wastes for days to months. The antimicrobial particles of this invention may be added to the contents of these tanks as additives and/or may be incorporated in coatings on the interior of the tanks. One may also incorporate the antimicrobial materials in disposable liners in these tanks. One may also add the antimicrobial materials of this invention introduced in porous or permeable cakes which may be added to the tanks, or to the flushes of toilets (portable or non-portable types) so as to provide antimicrobial ions into the water body for a long period of time (or/and multiple flushes).

Another example is incorporation of the materials of this invention in personal care (or body care) products. A non-exhaustive list of these include nail polish, shaving creams, shampoos, hair detangling solutions, hair gels and colorants, deodorants, toothpaste, toothbrushes, mouthwash, body creams ((including moisturizing and anti wrinkle creams), powders, mascara, blush, foundation, and other cosmetics, etc. Many of these formulations use preservatives such as parabens to ensure that the product has long life and that any bacterial contamination carried into the container from an applicator (e.g., brush) or by reintroducing the unused product by the user does not end up multiplying and then pose a hazard. The antimicrobial materials of the present invention may be used to replace parabens in cosmetics and body care products. Brushes and pads (e.g. foams) used to apply these products may also comprise antimicrobial materials of the present invention. These antimicrobial materials may be incorporated within the fibers which are used in making these brushes (including toothbrush bristles) or may be applied as coatings on these fibers. Similarly in pads they may be incorporated in the bulk of the materials to make these pads or incorporated as coatings on surfaces. For example open cell foams used for these applications may be treated with solutions/suspensions of the antimicrobial materials to coat the pore surfaces.

Antimicrobial applications include their use in construction materials, including wood preservatives, mold and mildew resistant products, and anti-fouling in other building and construction products such as non-fluid (including dry walls, insulating materials, faucets, sinks, toilet and other bathroom and kitchen products) and fluid products including paint, adhesive and caulks. This protection may be imparted to the fluid products while many of these products are in the containers (as preservatives) and/or they continue to have antimicrobial properties after they are applied in the field.

Applications include formulations comprising materials of this invention in formulations for treatment of water bodies for microbial and also for algae control; these include aquaculture facilities, fountains, lakes, reservoirs (crop and non-crop irrigation, potable), stocking (tank, water trough and ponds) and irrigation canals, drainage systems (canal, ditch and lateral), ponds (farm, industrial and recreational) sewage lagoons. The materials of this invention may be applied as coatings, as liquid suspension additives to the water bodies, or as porous or permeable cakes which will continue to elute the antimicrobial materials (or ions) for a long time.

Applications also include use in formulations for agricultural uses such as all food/feed crops; this includes orchard, row, field, and aquatic crops. The formulations of this invention may be applied by spraying from aqueous suspensions. Some examples of crops include: root and tubers, bulb vegetables, leafy vegetables (including *brassica*), fruiting vegetables, citrus, pome fruit, stone fruit, legumes, berries, cucurbits, cereals and tree nuts, ornamental crops, which includes flowering/non-flowering plants and trees. In addition uses also include wash treatments for fruits and vegetables to get rid of the microbes and other pests. One of the preferred methods of adding the metal salt particles (e.g., CuI) of the present invention is by producing functionalized particles using surface functionalizing agents which are already present as ingredients in the product. These functionalizing agents may be derived from natural sources (e.g. vegetable extracts) or formed synthetically. A non-exhaustive list of some of the materials used in body care products for functionalization is given in the section labeled "Functionalization agents". A preferred way to functionalize the particles is to grind the antimicrobial material (e.g., metal salts such as metal halides) in presence of these surface functionalizing agents as also described in the section on "Formation of functionalized particles by grinding". Typical concentration levels of antimicrobial halides are preferably less than 1% and more preferably less than 0.1% (as calculated based on the weight of the metal from the antimicrobial metal salt to the total formulation weight).

In many of these examples, the materials of this invention may be combined with other known antimicrobial materials used for that particular application.

As shown in numerous examples the materials of this invention may be added to any liquid or solid products to impart antimicrobial properties. Liquids include high viscosity and/or thixotropic liquids or any of those soft materials which will show predominantly viscous flow. Examples of high viscosity liquids at room temperature are body creams, ointments, toothpaste, deodorant sticks, uncured caulking material, waxy polishes, etc. Solid materials (including coatings) are typically able to support their weight and the soft materials upon deformation are able to regain their original shape. Examples of solids which are soft at room temperature are elastomers, foams and any other deformable bodies with chemical and physical crosslinks, etc.

Although the primary application of the functionalized salt particles of this invention are for antimicrobial agents, in several cases their use can be extended to other uses, where they show a superior effect as compared to the use of the same salts but where the particles are not functionalized. In addition functionalized particles of these salts may also be made inexpensively by grinding processes. These may be used as additives for improving thermal stability of nylon resins (e.g., nylon 6; nylon 6,6; nylon 6,10, etc.); catalytic agents for chemical reactions; improve both the processability and the properties of semiconductors made from metal salts; and finding drugs and/or treatments for those medical treatments which are not microbial in nature, such as in anticancer (or tumor reduction) agents.

Functionalized particles of compounds of this invention hold great promise for the future of cancer therapeutics. Some of the functionalized particles of these compounds under defined conditions induce apoptotic cell death, believed through the generation of intracellular reactive oxygen species (ROS). During one study, these particles elicited a dose-dependent decrease in cell viability. Oxidative stress is often hypothesized to be an important factor in cytotoxicity of many types of cells. The uptake of these particles can be enhanced through specific functionalization or active targeting for cancer cells. If designed appropriately, these particles will act as a drug vehicle able to target tumor or diseased cells and tissues. Through this functionalization it is believed that these particles can increase the selectivity for killing cancer cells and decrease the peripheral toxicity in healthy tissues and cells and allow for a dose escalation of a therapeutic. The ability to tailor the chemical composition, size and surface properties will allow for better pharmacokinetics properties.

The antimicrobial materials of the present invention may also be useful in preventing so-called mad cow disease. The prions responsible for this disease are specific proteins which occur in specific conformations. Interaction of such proteins with the materials of this invention can result in denaturation of the proteins with a change in their conformation, rendering them innocuous.

For most applications, the range of addition of the inventive active antimicrobial component (e.g., low solubility copper salt such as CuI) is about 0.001 to less than 5% by weight and preferably 0.001 to 3% by weight in the final end-use product. For those formulations where solutions (or suspensions) are used as end-use products, a preferred range of the active antimicrobial component is below 3% by weight. In order to produce these commercial end-use products one may utilize intermediate compositions, wherein the concentration of the active antimicrobial component may be very high, e.g., in a range of 30 to 95%. Examples of these intermediate compositions are masterbatches, concentrated powder or liquid mixes, etc. These intermediates may be produced in high concentration so that they can be easily transported, stored, and have characteristics so that they are easily miscible during the manufacturing of the final end-use products. As specific examples, these may be added to a resin on an injection molding machine before molding the end-use product, or to the resin before spinning the fibers, or to adhesive and caulking formulations, injection fluids in petroleum extraction, paint and coating formulations, etc. For those formulations which are dried by a loss of solvent (e.g., aqueous and solvent borne coatings), the concentration of the active antimicrobial material is calculated after drying. Preferred concentration range of the active antimicrobial material in personal care products, disinfectants, etc., is also below 5%, and preferably below 3%. In some applications higher concentration of the active antimicrobial may be used. The following examples are illustrations of the embodiments of the inventions discussed herein, and should not be applied so as to limit the appended claims in any manner.

4. Examples

Unless mentioned specifically in the examples, the following microbiological processes were used for testing of antimicrobial suspensions for efficacy against bacteria, mycobacteria, viruses, and fungi a. Microbial Assays The antimicrobial efficacy of the functionalized particles was evaluated using the following methods.

Maintenance and Preparation of Bacterial Isolates:

Test bacteria were obtained from the American Type Culture Collection (ATCC, Manassas, Va.) or The University of Arizona, Tucson, Ariz.: *Escherichia coli* (ATCC #15597), *Enterococcus faecalis* (ATCC #19433), *Pseudomonas aeruginosa* (ATCC #27313, ATCC #9027), *Staphylococcus aureus* (ATCC #25923), *Mycobacterium fortuitum* (ATCC #6841), *Salmonella enterica* serovar *Typhimurium* (ATCC 23564), and *Streptococcus mutans* (ATCC #25175). *Escherichia coli* 77-30013-2 (a copper resistant strain) was obtained from Dr. Chris Rensing and *Bacillus cereus* was obtained from Dr. Helen Jost at the University of Arizona, Tucson, Ariz.

Bacterial isolates used in these studies were routinely cultured on Tryptic Soy Agar (TSA; Difco, Sparks, Md.) at 37° C. or in Tryptic Soy Broth (TSB) medium at 37° C. on an orbital shaker at 200 r.p.m. In the case of *M. fortuitum*, Tween 80 (polyethylene glycol sorbitan monooleate; Sigma Aldrich, St. Louis, Mo.) was added to the broth to a final concentration of 0.1% (v/v) to inhibit the formation of bacterial aggregates.

Preparation of Bacterial Spore Cultures:

One-liter cultures of *B. cereus* were grown in 2 L Erlenmeyer flasks containing trypticase soy broth (TSB; Difco, Sparks, Md.) inoculated with exponential-phase cells from trypticase soy pre-cultures. The cultures were incubated at 37° C. on a rotary shaker at 200 rpm. Spore development was visualized by phase contrast microscopy. The cultures were harvested after 72 hours. All harvesting and washing procedures were performed at 25° C. Spores were harvested by centrifugation and resuspended with one-quarter culture volume of a solution containing 1M KCL and 0.5M NaCl. Centrifugation was repeated and cultures were resuspended in one-tenth culture volume of 50 mM Tris-HCL (pH 7.2) containing 1 mg lysozyme/mL. Cell suspensions were then incubated at 37° C. for 1 hour followed by alternate centrifugation and washing with 1M NaCl, deionized water, 0.05% sodium dodecyl sulfate (SDS), 50 mM Tris-HCl (pH 7.2), 10 mM EDTA, and three additional wash steps in deionized water. Spore suspensions were heat-shocked at 80° C. for 10 min and stored at 4° C. until use (Nicholson, W. L. and P. Setlow. 1990. Sporulation, germination, and outgrowth. pp. 391-450. In Harwood, C R and Cutting, S M (eds.) Molecular biological methods for *Bacillus*. John Wiley & Sons, New York).

Maintenance and Preparation of Viruses:

Test viruses were obtained from the ATCC or Baylor College of Medicine Houston, Tex.: MS2 coliphage (ATCC#15597-B1) and Poliovirus 1 (strain LSc-2ab) Baylor College of Medicine Houston, Tex.

MS2 was maintained as described: Test tubes containing approximately 5 ml of molten TSA containing 0.8% Bacto agar (Difco, Sparks, Md.) at 45° C. were inoculated with overnight cultures of *E. coli* and approximately $1 \times 10^5$ plaque forming units (PFU) of MS2. The molten agar overlay suspensions were gently vortexed and poured evenly across the top of TSA plates and allowed to solidify. Following incubation of 24 hours at 37° C., 6 ml of sterile phosphate buffered saline (PBS; pH 7.4; Sigma-Aldrich, St. Louis, Mo.) was added to the agar overlays and allowed to sit undisturbed for 2 hours at 25° C. Following the incubation, the PBS suspension was collected and centrifuged (9,820×g for 10 min) to pellet the bacterial debris. The remaining supernatant containing MS2 was filtered through a 0.22 μm (Millex; Millipore, Bedford, Mass.) sterile membrane pre-wetted with 1.5% beef extract and stored in sterile tubes at 4° C. until use. To determine the MS2 titer, the double-agar overlay method as described above was used; however, after the 24 hour incubation at 37° C., MS2 was enumerated by plaque formation to determine the number of PFU/ml.

Poliovirus 1 (strain LSc-2ab) was maintained as described: Poliovirus 1 was maintained in cell culture flasks containing BGM (Buffalo green monkey kidney; obtained from Dr. Daniel Dahling at the United States Environmental Protection Agency, Cincinnati, Ohio) cell monolayers with minimal essential medium (MEM, modified with Earle's salts; Irvine Scientific, Santa Ana, Calif.) containing (per 100 ml total volume) 5 ml of calf serum (CS; HyClone Laboratories, Logan, Utah), 3 ml of 1 M HEPES buffer (Mediatech Inc., Manassas, Va.), 1.375 ml of 7.5% sodium bicarbonate (Fisher Scientific, Fair Lawn, N.J.), 1 ml of 10 mg/ml kanamycin (HyClone Laboratories, Logan, Utah), 1 ml of 100× antibiotic-antimycotic (HyClone Laboratories, Logan, Utah), and 1 ml of 200 mM glutamine (Glutamax; HyClone Laboratories, Logan, Utah) at 37° C. with 5% $CO_2$.

Viruses were propagated by inoculating BGM cell monolayers. Following the observation of ≥90% destruction of the cell monolayer, the cell culture flasks were frozen at −20° C. and thawed three successive times to release the viruses from the host cells. The culture suspension was then centrifuged (1000×g for 10 min) to remove cell debris, and then precipitated with polyethylene glycol (PEG; 9% w/v) and sodium chloride (5.8% w/v) overnight at 4° C. (Black et al. "Determination of Ct values for chlorine resistant enteroviruses," J. Environ. Sci. Health A Tox. Hazard Subst. Environ. Eng. 44: 336-339, 2009). Following the overnight incubation, the viral suspension was centrifuged (9,820×g for 30 min at 4° C.) and the viral pellet re-suspended in 10 ml PBS. A Vertrel XF extraction was performed at a 1:1 ratio to promote monodispersion of the virus and the removal of lipids (centrifugation at 7,500×g for 15 min at 4° C.) (Black et al., 2009). The top aqueous layer containing the virus was carefully removed using a pipette and aliquoted in 1 ml volumes in sterile cryogenic vials (VWR, Radnor, Pa.). A viral titration for poliovirus 1 was performed using a 10-fold serial dilution plaque-forming assay described by Bidawid et al., "A feline kidney cell line-based plaque assay for feline calicivirus, a surrogate for Norwalk virus." J. Virol. Methods 107: 163-167. (2003). BGM cell monolayers in 6-well tissue culture plates (Corning Inc., Corning, N.Y.) were rinsed twice with TRIS buffered saline[0.32 L TBS-1 (31.6 g/L Trizma base, 81.8 g/L NaCl, 3.73 g/L KCl, 0.57 g/L $Na_2HPO_4$— anhydrous) in 3.68 L ultrapure $H_2O$] and then inoculated with 0.1 ml volumes of 10-fold serial dilutions of the virus stock and incubated at 37° C. for 30 minutes. Following this incubation period, 3 ml of a molten solution of MEM containing (per 100 ml) 0.75% Bacto-agar (Becton, Dickenson and Co., Sparks, Md.), 2% FBS (HyClone Laboratories, Logan, Utah), 3 ml of 1 M HEPES buffer (Mediatech Inc., Manassas, Va.), 1 ml of 7.5% sodium bicarbonate (Fisher Scientific, Fair Lawn, N.J.), 1 ml of 10 mg/ml kanamycin (HyClone Laboratories, Logan, Utah), 1 ml of 100× antibiotic-antimycotic (HyClone Laboratories, Logan, Utah), and 1 ml of 200 mM glutamine (Glutamax; HyClone Laboratories, Logan, Utah) was added as an overlay to each well and allowed to solidify. The plates were then incubated at 37° C. with 5% $CO_2$ for two days. Following incubation, the agar overlays were removed and the cell monolayers were stained with 0.5% (w/v) crystal violet (Sigma-Aldrich, St. Louis, Mo.) dissolved in ultrapure water and mixed 1:1 with 95% ethanol. Plaques were counted to enumerate infectious viruses.

Maintenance and Preparation of Mold Isolates:

Test molds were obtained from the American Type Culture Collection (ATCC, Manassas, Va.) or The University of Arizona, Tucson, Ariz.: *Trichophyton mentagrophytes* (ATCC #9533), *Streptoverticilium reticulum* (ATCC #25607). *Penicillium* and *Aspergillus niger* isolates were obtained from Dr. Charles Gerba at the University of Arizona.

*T. mentagrophytes, Penicillium* and *Aspergillus niger* isolates were maintained on Sabouraud's agar (Neogen Corporation, Lansing, Mich.) slants at 25° C. *S. reticulum* isolates were maintained on Yeast Malt Extract Agar (ISP Medium 2) containing (per 1 liter deionized water), 4.0 g yeast extract (Beckton Dickinson, Franklin Lakes, N.J.), 10.0 g malt extract (Amresco, Solon, Ohio), 4.0 g dextrose (Hardy Diagnostics, Santa Maria, Calif.), and 20.0 g agar (EMD Chemicals, Gibbstown, N.J.). For preparation of *Penicillium* and *Aspergillus niger* spore suspensions, mature slant cultures containing fruiting bodies were washed repeatedly with 10 mL of sterile PBS to release spores. The spore suspension was then transferred to a 15 mL conical tube and vortexed to disperse the spores. For preparation of *T. mentagrophytes* spore suspensions, methods were adapted from the ASTM 2111-05 standard (ASTM Standard 2111, 2005, "Standard Quantitative Carrier Test Method to Evaluate the Bactericidal, Fungicidal, Mycobactericidal, and Sporicidal Potencies of Liquid Chemical Microbicides." ASTM International, West Conshohocken, Pa., 2005.). A small section of mycelial mat from mature slant cultures was transferred to 3-4 plates of Sabouraud's agar. These were incubated for 10-15 days at 25° C. Mature mycelial mats were removed from the agar surface and placed into a 250 ml Erlenmeyer flask containing 50 ml sterile saline (0.85% NaCl) and glass beads. The flask was shaken vigorously to release conidia spores from the fungal hyphae and the suspension was filtered through sterile cotton to remove hyphae fragments.

1) Liquid Suspension Testing

Bacterial Reduction Assay.

Overnight suspensions were harvested by centrifugation (9,820×g, 15 min, 20° C., JA-14 rotor, Beckman J2-21 centrifuge; Beckman Coulter, Inc., Fullerton, Calif.) and resuspended in 100 ml of sterile PBS. The above centrifugation process was carried out two additional times to wash the cells and the final harvest was resuspended in 10 ml of PBS. Bacterial suspensions were then adjusted in PBS to an optical turbidity (measured using a BIOLOG turbidimeter, Hayward, Calif.) equivalent to a McFarland number 0.5 standard. Sterile 50 ml polypropylene conical tubes (Becton Dickinson and Company, Franklin Lakes, N.J.) containing PBS were inoculated with test suspensions to a final concentration of approximately $1.0\times10^6$ CFU/ml. Functionalized particles of the present invention were evaluated at either 10 ppm silver or 60 ppm copper. Test samples were then placed on an orbital shaker (300 rpm) at 25° C. for the duration of the experiment. At predetermined time intervals (e.g., 1, 3, 5, 24 hours), 100 μl samples were collected and neutralized with Dey Engley neutralizing broth (D/E; Difco, Sparks, Md.) at a ratio of 1:10. Bacterial samples were serially diluted in sterile PBS and enumerated using the spread plate method (Eaton et al., "Spread Plate Method," in Standard Methods for the Examination of Water & Wastewater, $21^{st}$ ed., American Public Health Association, Washington, D.C., pp. 9-38-9-40. 9215C. 2005) with incubation at 37° C. for either 24 hours (*E. coli, P. aeruginosa, S. aureus*, S. *Typhimurium* and *E. faecalis*) or 48 and 72 hours (*M. fortuitum* and *S. mutans*).

Evaluation of Antimicrobial Properties of Porous Silica Particles:

Experiments for porous silica particles without antimicrobial salt and those comprising antimicrobial salt were conducted in 100 ml of sterile PBS in 250 ml Erlenmeyer flasks. Bacterial suspensions were added to a final concentration of $1.0 \times 10^6$ CFU/ml. Powdered silica samples were tested at 0.1 g dry weight per 100 ml of PBS. A control with bacteria but no added particles was also included. Powdered silica samples were added to each flask and kept in suspension by agitation using stir plates (VWR VMS-C7, VWR, Radnor, Pa.) for the duration of the experiment at 25° C. At predetermined time intervals (e.g. 0.25, 1, 6, 24 hours), 1 ml samples were collected and neutralized with D/E neutralizing broth at a ratio of 1:2. Samples were then diluted and enumerated as described before.

Viral Reduction Assay.

Poliovirus 1 experiments were conducted in 10 ml of sterile PBS in 50 ml sterile polypropylene conical tubes (Becton Dickinson and Company, Franklin Lakes, N.J.). MS2 experiments were conducted in 50 ml of sterile PBS in 250 ml sterile covered Pyrex beakers. The purified stocks of the viruses were added separately to the tubes/beakers to achieve the desired final test concentration of approximately $1.0 \times 10^6$ PFU/ml. Functionalized particles of the present invention were evaluated at either 10 ppm silver or 60 ppm copper. The tubes/beakers were then placed on an orbital shaker (300 rpm) for the duration of the experiment. Experiments were performed at 25° C. At predetermined time intervals (e.g., 3, 5, 7, 24 hours), 100 µl samples were collected and neutralized with D/E neutralizing broth at a ratio of 1:10. Functionalized particle efficacy was determined by the agar overlay method as described above in maintenance and preparation of viruses section.

Mold Reduction Assay.

Sterile 50 ml polypropylene conical tubes (Becton Dickinson and Company, Franklin Lakes, N.J.) containing 10 ml PBS were inoculated with mold spore suspensions of approximately $1.0 \times 10^6$ CFU/ml. Functionalized particles of the present invention were evaluated at either 10 ppm silver or 60 ppm copper. Test samples were then placed on an orbital shaker (300 rpm) at 25° C. for the duration of the experiment. At predetermined time intervals (e.g., 1, 3, 5, 24, 48, 72 and 96 hours), 100 µl samples were collected and neutralized with D/E neutralizing broth at a ratio of 1:10. Mold samples were serially diluted in sterile PBS and enumerated with the spread plate method (Eaton et al., "Spread Plate Method," in Standard Methods for the Examination of Water & Wastewater, 21$^{st}$ ed., American Public Health Association, Washington, D.C., pp. 9-38-9-40. 9215C, 2005) with incubation at 25° C. for 48 and 72 hours.

Determination of Antimicrobial Activity by Optical Density Measurements.

Bacterial suspensions with or without antimicrobial particles where monitored for growth using a turbidimetric measurement. Turbid or cloudy suspensions indicated growth or increase in biomass whereas clear suspensions indicate no growth or no increase in biomass. A deficiency or lack of growth correlates to the effectiveness of the antimicrobial particles. Optical densities where monitored using a spectrophotometer such as an Eppendorf Bio Photometer cuvette reader (Eppendorf North America, Inc, Enfield, Conn.) or Biotek Synergy 2 multiwell plate reader (Biotek Inc., Winooski, Vt.).

Determination of Antimicrobial Activity Against Bacterial Spore Germination.

To determine antimicrobial activity against bacterial spores, sterile 2 mL polypropylene tubes were inoculated with *B. cereus* spore suspensions and treated with approximately 2 pM or 60 ppm of nanoparticles for 24 hours at room temperature (22° C.). After 24 hours of incubation, suspensions were pelleted by centrifugation at 13,000×g, and the supernatant removed and discarded. Pellets were resuspended in 200 µl of TSB. The tubes were then incubated for 24 hours at 25° C. and 37° C. Germination characteristics of *B. cereus* spores after 24 hours of incubation with nanoparticle chemistries were determined by optical density (Eppendorf Bio Photometer) at a wavelength of 600 nm (OD600).

2) Coated Surface Testing

Experiments for coated stainless steel or aluminum surfaces with and without functionalized particles were conducted based on the Japanese Industrial Standard Z 2801: 2000 method (JIS Z 2801:2000, "Antimicrobial products—Tests for antimicrobial activity and efficacy", Japanese Standards Association, Tokyo, Japan, 2000.) with minor modifications. Prior to the experiment, 50×50 mm square coupons of steel or aluminum with the desired coating were disinfected with 70% ethanol twice and air dried. Overnight cultures of bacteria were washed and standardized as mentioned previously. Bacterial suspensions with a final concentration of $1.0 \times 10^7$ cfu/ml were prepared in PBS and 0.4 ml was inoculated onto each test surface. The inoculum was held in contact with the surface using UV sterilized 40×40 mm polyethylene film cover slips. A set of control surfaces coated with polymer but containing no functionalized particles was also inoculated for a zero hour time point to determine the initial inoculum concentration and at each time interval following to determine the change in organism concentration without antimicrobial. All inoculated surfaces were incubated in a sealed environment at 25° C. and >95% relative humidity (RH). At predetermined time intervals (e.g. 3, 6, 24 hours), the cover slip was aseptically removed and the bacteria were recovered by swabbing the surface and the cover slip with a cotton swab pre-moistened in sterile PBS. The swab was then neutralized in 1 ml of D/E neutralizing broth and the cotton tip of the swab was broken off into the tube containing D/E. Samples were then vortexed for 30 seconds and diluted/enumerated as described previously. Three replicate samples for each surface treatment were tested for each time interval in this manner. Bacterial reductions were determined by comparing the recovery of bacteria from the untreated control samples (polymer coated coupons without functionalized particles) to those recovered from treated samples containing functionalized particles at each exposure interval.

A revised version of the JIS method was later developed to enable more rapid testing of polymer coatings. The method above was performed with smaller surfaces (25×25 mm square coupons) and smaller polyethylene coverslips (20×20 mm). Surfaces were disinfected with a slightly different method to better preserve coating integrity; each surface was disinfected once with 70% ethanol and immediately irrigated with sterile deionized (DI) water before air-drying prior to the experiment. Surfaces were inoculated with 0.1 ml of a of $1.0 \times 10^7$ cfu/ml bacterial suspension and were incubated as previously described. At predetermined time intervals (e.g. 3, 6, 24 hours), samples were neutralized by completely submersing both the surface and the cover slip in 10 ml of D/E neutralizing broth in sterile polypropylene bottles. These bottles were sealed and sonicated (30 seconds, nominal main frequency 67 KHz, Cavitator®

Ultrasonic Cleaner, Mettler Electronics, Anaheim, Calif.) to recover bacteria from the surface and cover slip. The D/E solution was diluted/enumerated as described before. Three replicate samples for each surface treatment were tested for each time interval in this manner. Bacterial reductions were determined as described previously.

Certain coatings were tested under more rigorous experimental conditions set forth in the EPA "Test Method for Efficacy of Copper Alloy Surfaces as a Sanitizer" with some modifications. Cultures of *Staphylococcus aureus* ATCC 25923 were grown for 48±4 hours. To simulate organic soil load, fetal bovine serum (FBS) and Triton X-100 were added to an aliquot of the overnight culture for a final concentration of 5% FBS and 0.01% Triton X-100. Test surfaces with the desired coating (25×25 mm square coupons) were disinfected as described for the revised JIS method above. Each test surface was inoculated with 20 µl of the culture with organic load and spread uniformly on the surface with a sterile glass rod and allowed to dry completely (approx. 20 min at 22° C., 20-45% RH). No cover slip was used for this experiment. A set of control surfaces coated with polymer but containing no functionalized particles was also inoculated for a zero hour time point to determine the initial inoculum concentration after drying and at the 120 minute time interval to determine the change in organism concentration without antimicrobial. At the end of the drying period, samples were incubated at room temperature (22° C., 20-45% RH) in sterile covered petri dishes for 120 minutes. Samples were then neutralized in D/E and sonicated for 30 as described previously. The D/E solution was diluted/enumerated as described before. Three replicate samples for each surface treatment were tested for each time interval in this manner. Bacterial reductions were determined as described previously.

3) Spray Antimicrobial Testing

The following procedure was used to determine the efficacy of functionalized particles used in spray applications. Test carriers (glazed 4.25"×4.25" ceramic tiles) were washed, treated with 10% bleach, and rinsed before being sprayed with 70% ethanol and allowed to air dry. Spray bottles were checked prior to testing to determine that each bottle dispensed similar volumes of liquid when sprayed. The bottles and spray nozzles were thoroughly washed and rinsed with DI water followed by 70% ethanol. The ethanol was allowed to dry and each bottle/nozzle was rinsed with sterile DI water. The bottles were emptied and the test samples were added aseptically to each bottle. In addition to test sprays, a solution of phosphate buffered saline (PBS) was used as a control (non-antimicrobial) spray. An overnight culture of the bacteria of interest was prepared in 100 ml of tryptic soy broth and centrifuged and washed in PBS as previously described. After the final centrifugation step, the bacterial pellet was re-suspended in 1/10 of the original volume (10 ml) in PBS. From this solution, 0.1 ml was inoculated onto each test carrier and spread uniformly across the surface with a sterile glass rod. Each carrier was allowed to dry completely before spray testing (approx. 20 min at 22° C., 20-45% RH). Each carrier was sprayed uniformly (fine mist setting) with the test solutions just to the point of covering the surface (approx. 2.5 ml). A set of samples sprayed with PBS were sampled immediately after spraying as a zero hour to serve as a control sample to determine the initial inoculum concentration on each carrier. The remaining surfaces were incubated at room temperature (22° C., 20-45% RH) in open air. At predetermined time intervals (e.g. 0.25, 1, 6 hours), bacteria were recovered by swabbing the surface with a cotton swab pre-moistened in sterile D/E neutralizing broth. The swab was then neutralized in 1 ml of D/E and the cotton tip of the swab was broken off into the tube containing D/E. Samples were then vortexed for 30 seconds. In some cases, where the spray samples were more acidic and thus were not completely neutralized at a 1:10 dilution, the sample was immediately diluted following the vortex step in 1:100 in PBS. In both cases, the neutralized sample was diluted/enumerated as described before. Three replicate samples for each spray treatment (including the PBS control solution) were tested for each time interval in this manner. Bacterial reductions were determined by comparing the recovery of bacteria from the control carriers (those sprayed with PBS solution) to those recovered from carriers sprayed with test samples containing functionalized particles at each exposure interval.

The following procedure was used to determine if sprays containing functionalize particles could impart some residual antimicrobial effect on sprayed surfaces. Test carriers and spray bottles were prepared as previously described for spray testing. Spray bottles were filled with test samples and phosphate buffered saline (PBS) was used as a control spray. An overnight culture of bacteria was prepared as previously mentioned for spray testing but was not immediately applied. Each test carrier was sprayed uniformly with the test solutions just to the point of covering the surface (approx. 2.5 ml). A set of samples sprayed with PBS was also included for each time interval. Each spray sample was allowed to sit undisturbed on the surface for a two minute conditioning time after which the surface was wiped with a paper towel to remove excess liquid. The surfaces were held at room temperature (22° C., 20-45% RH) for a predetermined "residual time" (e.g. 0, 3, 24 hours). Following this, 0.1 ml of the bacterial concentrate were inoculated onto each test carrier and spread uniformly across the surface with a sterile glass rod. The surfaces were incubated at room temperature (22° C., 20-45% RH) in open air. Immediately after inoculation and at predetermined "post-inoculation" time intervals (e.g. 1, 3, 6 hours), the bacteria were recovered by swabbing and neutralized as described previously for spray testing. The neutralized sample was diluted/enumerated as described previously. Three replicate samples for each spray treatment (including the PBS control solution) were tested for each time interval in this manner. Bacterial reductions were determined as described previously for spray testing.

4) Cream/Shampoo Antimicrobial Testing

Experiments for cream, lotion, and shampoo based samples with and without functionalized particles were conducted based on the USP <51> method ("Antimicrobial Effectiveness Testing.", U.S. Pharmacopeia, Rockville, Md.) with minor modifications. Briefly, overnight cultures of bacteria were centrifuged, washed and standardized in PBS as detailed in previous sections. The bacterial suspension was diluted as needed for a specific experiment, ranging from $1 \times 10^7$-$1 \times 10^9$ cfu/ml. For each sample, 1 g aliquots were placed into sterile polystyrene tubes. In addition, 1 ml aliquots of PBS were used as a control solution. Each aliquot was inoculated with 0.01 ml of the washed bacterial suspension containing 10 times the desired final test concentration and mixed with a sterile wooden applicator or lightly vortexed depending on the viscosity of the sample. At predetermined time intervals (e.g. 7, 14, 28 days), samples were taken by adding 1 ml D/E neutralizing broth to the sample and vortexing lightly to mix. Samples were then diluted/enumerated and bacterial reductions were determined as described previously. All samples were tested in duplicate.

A zone of inhibition type assay was also used to determine the efficacy of functionalized particles in cream and petroleum gel products. Overnight cultures of bacteria were centrifuged, washed and standardized in PBS as described previously. The standardized bacterial solution was diluted to a concentration of $1\times10^4$ cfu/ml. Plates of tryptic soy agar (TSA) were inoculated with 0.1 ml of the diluted bacteria. A sterile agar punch (approx. 5 mm in diameter) was used to remove a plug of agar from each inoculated plate, creating a well in the center of the plate. Samples of cream or petroleum gel with and without functionalized particles were added until the entire well was filled with sample (approx. 0.05 ml). A plate with agar plug removed but without added sample was also included as a positive growth control sample. All plates were covered and incubated at 37° C. for 24 hours. The diameter of the resulting zone of inhibition (area with no bacterial growth or inhibited bacterial growth) was measured for each sample and compared with both the positive growth control and samples without functionalized particles to determine their relative antimicrobial efficacy.

5) *Streptoverticilium reticulum* Polymer Staining Test

Anti-staining experiments for polymer foams containing functionalized particles were conducted based on ASTM E1428-99 standard method (ASTM E1428-99, "Standard Test Method for Evaluating the Performance of Antimicrobials in or on Polymeric Solids Against Staining by *Streptoverticilium reticulum* (A Pink Stain Organism)", ASTM, West Conshohocken, Pa., 2009). Briefly, samples of polymer foam were cut to predefined dimensions (e.g., 10 mm, 30 mm square coupons). Plates of yeast malt extract agar (ISP Medium 2, see above in Maintenance and preparation of mold isolates) were poured to a depth of 5 to 8 mm and allowed to solidify before testing. A stock plate of *S. reticulum* was grown prior to experimentation for 7-14 days. In order to harvest *S. reticulum* cells, 3 ml of sterile PBS were added to the stock plate and a sterile cotton swab was used to break up the fungal mat. This swab was used to streak fungal cells onto plates of ISP Medium 2. A coupon of the sample foam was applied to the center of the inoculated plate and pressed lightly to ensure good contact between the agar surface and the sample. In addition, a foam sample containing no functionalized particles was also tested. Samples with and without functionalized particles were also applied to ISP Medium 2 without the presence of inoculum to determine if staining occurred in foam samples as a result of the agar alone. Three replicate samples were tested for each treatment. All plates were covered and incubated at 30° C. under humid conditions (approx. 95% RH) for 14 days. All plates were observed for zones of inhibition present in the newly grown fungal mat. Samples were then removed from the agar surface to observe for staining Samples were rated on a scale from 1 to 5 with a value of '1' pertaining to the color of fresh, untested foam samples and a value of '5' pertaining to the maximum amount of stain observed on foam samples containing no antimicrobial exposed to *S. reticulum*. Samples exposed to agar without inoculum were also scored against this scale.

6) Wound Dressing Antimicrobial Testing

The following procedure was used to determine the antimicrobial efficacy of wound dressings containing functionalized particles. Wound dressings were provided as sterile 10 mm diameter disks. An overnight culture of *P. aeruginosa* (ATCC #9027) was prepared as previously described but was not centrifuged or washed. Polycarbonate membrane films (25 mm diameter, 0.2 µm pore size, Whatman) were sterilized by autoclaving and placed in the center of TSA plates. The overnight culture was diluted 1:10,000 in PBS and 0.01 ml was inoculated as a single spot in the center of each membrane filter. These plates were incubated at 37° C. for 24 hours to allow for the formation of bacterial biofilms. After growth, each membrane filter was transferred to a fresh TSA plate. Wound dressing samples were moistened with 0.05-0.2 ml DI water and applied gently to the biofilm spot. The biofilms with wound dressings were incubated at 37° C. for 18 hours. Each wound dressing and membrane filter were transferred to 10 ml of D/E neutralizing broth, vortexed for 1 min and sonicated for 1 minute (described previously) to release bacteria from the surfaces. The neutralized samples were diluted/enumerated as described previously. Bacterial reductions were calculated and compared with the control samples containing no functionalized particles and biofilm control samples with no applied wound dressings.

7) Pet Chew Antimicrobial Testing

The following procedure was used to evaluate the antimicrobial efficacy of pet chews treated with functionalized particles. Treated and untreated pet chews (pig ears) were cut to 1"×0.5" pieces and placed into empty sterile petri dishes. All pet chews were incubated in sealed containers at room temperature (22° C., >95% RH) in order to reduce liquid absorption by the pet chews. Overnight cultures of bacteria were centrifuged and washed as described previously. A $1\times10^{10}$ cfu/ml solution of bacteria was prepared and 0.1 ml was inoculated onto each pet chew. A sterile glass spreading rod was used to spread the inoculum to cover the top surface of the pet chew. A set of untreated pet chews containing no functionalized particles was also inoculated for a zero hour time point to determine the initial inoculum concentration and for each time interval following to determine the change in organism concentration without antimicrobial. All samples were incubated in sealed containers at 22° C. and >95% RH. At predetermined time intervals (e.g. 1, 6, 24 hours), samples were neutralized by submerging the entire pet chew in 10 ml D/E neutralizing broth, vortexed for 30 seconds and sonicated (described previously) for 1 minute to release bacteria from the surfaces. The D/E solution was diluted/enumerated as described previously. Bacterial reductions were calculated and compared with untreated control samples containing no functionalized particles.

Preparation of Materials and Results

Example 1: Synthesis of CuI Particles Functionalized with PVP at Cu/PVP=1/3.3 w/w 10% PVP solution was made by dissolving 1 g Polyvinylpyrrolidone, mol. wt.=10,000 (Sigma-Aldrich #PVP10) in 9 g water. 2.232 g of this solution solution was added into the solution of 0.211 g Copper(II) acetate monohydrate (Sigma-Aldrich #217557) solution prepared by dissolving 1.057 mmol of the monohydrate in 6.227 g water under stirring. Afterwards, 0.3168 g sodium iodide (2.114 mmol) dissolved in 5 g water was dropped slowly into the copper solution and stirred overnight. Next day, the CuI suspension was washed to remove the formed iodine by extracting 7-10 times 2.5-3 ml with diethyl ether. The remaining ether was separated from the solution by evaporation under vacuum and then water was added to compensate for the loss of weight during processing. The final concentration of copper based on the calculation of metallic copper is 0.48% w/w. Reaction: $Cu^{2+}+2I^-\rightarrow CuI_2\rightarrow CuI_{(s)}+I_2$. 10% Aspartic acid solution was made using 0.296 g NaOH pellets (7.4 mmol) which was dissolved in 8.6 g water, 0.988 g Aspartic acid (7.4 mmol) (Sigma #A9006) added into the sodium hydroxide solution and then stirred until a clear solution was obtained. The aspartic acid solution was added to the CuI solution in a proportion so that the ratio of PVP/Aspartic acid (molar) was 1:2.5.

This solution was tested against Poliovirus (PV-1 LSc-2ab). The testing was carried out on Poliovirus (at 60 ppm copper concentration). Functionalized CuI particles were found to be particularly effective against poliovirus, with decreases in microbial populations 3.11 $\log_{10}$ reduction being found in 24 hours. A further encouraging result of the testing on poliovirus was the observation of the cell culture work carried out here, which showed no adverse effect of the functionalized particles on cell viability and reproduction in culture.

Example 2: Synthesis of CuI-PEG Dispersion w/pH Modifier

A dispersion of CuI surface modified with polyethylene glycol (PEG) was prepared in water using nitric acid as a pH modifier. To a reaction flask fitted with a stir bar was added 4.5 g of PEG (MW=10,000), and 0.0476 g CuI (99.999%) and 50 ml of acetonitrile. The mixture was stirred at room temperature for about 30 minutes to give a light green solution. The reaction flask was placed on a rotary evaporator and the solvent removed at 25° C. to a paste-like consistency. The temperature was then increased to 45° C. to complete removal of acetonitrile. This resulted in a yellow powder. This powder was dispersed in 50 ml of DI water and 0.05 ml (0.07 g) of concentrated nitric acid was added to form an off-white mixture. Upon stirring in the dark over night the dispersion became clear to give a light yellow dispersion.

Example 3: Preparation of Ag/PVP Dispersion

To a round bottom flask fitted with a condenser was added 50 ml of DI water (18 Mohm-cm) and 20 g of PVP (10,000 MW, Sigma Aldrich Cat. # PVP10). The mixture was stirred at room temperature to form a clear yellow solution. To this solution was added 0.04926 g of silver nitrate (≥99.0% ACS reagent Sigma Aldrich Cat. #209139) and the solution heated to 70° C. for 7 hours while stirring. During this time the reaction was followed by optical absorption with the formation of the Plasmon peak at 425 nm due to the reduction of silver nitrate to silver metal by PVP. The final dispersion of Ag nano-particles was orange/brown in color and was transparent. Dynamic light scattering on a dilute sample of the dispersion gave a mean particle size of 7 nm.

Example 4: Synthesis of AgBr/PVP Dispersion

A silver bromide dispersion was prepared by dissolving 20 g of PVP (10,000 MW, Sigma Aldrich Cat. # PVP10) in 40 ml of DI water (18 Mohm-cm). To this solution while stirring was added 0.0492 g of silver nitrate, (≥99.0% ACS reagent Sigma Aldrich Cat. #209139), resulting in a clear yellow solution. In a separate reaction vessel a reducing solution was prepared by dissolving 0.0357 g of potassium bromide (anhydrous powder 99.95% Sigma Aldrich Cat. #451010), in 10 ml DI water (18 Mohm-cm). This KBr solution was added drop wise to the $AgNO_3$/PVP solution to form a yellow/orange transparent dispersion of AgBr. Dynamic light scattering on a dilute sample of the dispersion gave a mean particle size of 4 nm.

Example 5: Synthesis of CuI/PVP Dispersion

To a reaction flask containing 50 ml of anhydrous acetonitrile, (99.8% Sigma Aldrich Cat. #271004), was added 10 g of PVP (10,000 MW, Sigma Aldrich Cat. # PVP10) and stirred to form a light yellow solution. To this solution was added 0.0476 g of CuI (98.0% Sigma Aldrich Cat. #205540) and after stirring for 30 minutes this resulted in a clear pale green solution. Then the bulk of the acetonitrile was removed under reduced pressure at 30° C. to form a viscous paste. The temperature was then increased to 60° C. to completely remove the solvent to give a pale green solid. To this solid was added 50 ml of DI water (18 Mohm-cm) and stirred to form a transparent bright yellow dispersion. Dynamic light scattering on a dilute sample of the dispersion gave a mean particle size of 4 nm.

Example 6: Synthesis of PVP-BASF-CuCl Dispersion

To a reaction flask containing 50 ml of anhydrous acetonitrile (99.8% Sigma Aldrich Cat. #271004) was added 14 g of PVP (BASF K17) and stirred to form a clear solution. To this solution was added 0.0239 g of CuCl (ACS reagent >99.0% Sigma Aldrich Cat. #307483) and after stirring for 30 minutes this resulted in a green/yellow solution. The bulk of the acetonitrile was removed under reduced pressure at 30° C. to form a viscous paste. The temperature was increased to 60° C. to completely remove the solvent to give a pale green solid. To this solid was added 50 ml of DI water (18 Mohm-cm) and stirred to give a transparent bright yellow dispersion.

Example 7: Synthesis of CuI/PVP-BASF+Acetic Acid+$HNO_3$

To a reaction vessel were added 4.05 g of PVP (BASF K17) and 50 ml of anhydrous acetonitrile (99.8% Sigma Aldrich Cat. #271004). This was capped and left to stir at room temperature to form a clear colorless solution. To this solution was added 0.0476 g of CuI (99.999% Sigma Aldrich Cat. #215554) and stirred at 25° C. for 30 minutes to form a transparent light yellow solution. The bulk of the acetonitrile was removed under reduced pressure at 30° C. to form a viscous paste. The temperature was increased to 60° C. to completely remove the solvent to give a yellow uniform solid. To this solid was added 50 ml of DI water (18 Mohm-cm) and stirred to give a cloudy white dispersion. This was left to stir for 3 days in the dark the dispersion remained cloudy with a light white precipitate. While stirring 0.3 ml of glacial acetic acid (ACS reagent ≥99.7% Sigma Aldrich Cat. #320099) was added and immediately the dispersion turned a orange/yellow color but was cloudy with a slight precipitate. To this mixture was added 0.05 ml of concentrated nitric acid (ACS reagent ≥90% Sigma Aldrich Cat. #258121) and the solution cleared up to give a transparent light yellow solution.

Example 8: Synthesis of CuI/VP-VA Copolymer-BASF+$HNO_3$ Dispersion

To a reaction flask containing 50 ml of anhydrous acetonitrile (99.8% Sigma Aldrich Cat. #271004) was added 6.75 g of the copolymer PV-VA (BASF Luvitec VA 64) and stirred to form a clear solution. To this solution was added 0.0476 g of CuI (99.999% Sigma Aldrich Cat. #215554) and after stirring for 30 minutes this resulted in a green/yellow solution. The bulk of the acetonitrile was removed under reduced pressure at 30° C. to form a viscous paste. The temperature was then increased to 60° C. to completely remove the solvent to give a yellow uniform solid. To this solid was added 50 ml of DI water (18 Mohm-cm) and stirred to give a cloudy light yellow slurry. Under stirring 0.05 g of concentrated nitric acid (ACS reagent ≥90% Sigma Aldrich Cat. #258121) was added to the mixture and it turned a light yellow color and was transparent.

Example 9: Synthesis of CuI/PVP-BASF+HNO$_3$

To a round bottom flask fitted with a stir bar were added 4.275 g of PVP (BASF K17) and 50 ml of anhydrous acetonitrile (99.8% Sigma Aldrich Cat. #271004). This was capped and left to stir at room temperature to form a clear colorless solution. To this solution was added 0.225 g of CuI (99.999% Sigma Aldrich Cat. #215554) and stirred at 25° C. for 30 minutes to form a transparent light yellow solution. The bulk of the acetonitrile was removed under reduced pressure at 30° C. to form a viscous paste. The temperature was then increased to 60° C. to completely remove the solvent to give a yellow uniform solid. To this solid was added 50 ml of DI water (18 Mohm-cm) and stirred to give a cloudy light yellow dispersion. While stirring 0.07 g of concentrated nitric acid (ACS reagent ≥90% Sigma Aldrich Cat. #258121) was added to the mixture and it turned colorless and lightly cloudy with no precipitate. Dynamic light scattering on a diluted sample of the dispersion showed a bimodal distribution for volume fraction analysis with particles with peaks at diameter of 263 and 471 nm.

In another preparation following the above route, the proportion of components was changed. The amount of PVP (BASF K17) was 2.25 g in 50 ml acetonitrile. To this was added 0.0476 g of CuI (99.999%). This was processed as before and the dry powder was redispersed in 60 ml DI water. The solution was milky/pale yellow. After stirring 0.05 ml of nitric acid was added and stirred for two days. The solution became clear yellow with no precipitate. The solution remains stable after this process. The particle size was 4 nm.

Example 10: Synthesis of $Ag_{0.5}Cu_{0.5}I$ and $Ag_xCu_{1-x}Br$ Nanoparticles

This method results in "solid solutions," meaning not separate distinct liquid phases of CuI and AgI but where one metal is substituted for the other randomly throughout the crystal or a non-crystalline lattice structure of the solid. For example, $Ag_{0.5}Cu_{0.5}I$ may be considered a solid solution of CuI and AgI where both are present in equimolar quantities, or one may consider CuI is about 51% by weight and AgI is 49% by weight. 10 g of PVP (10,000 MW, Sigma Aldrich Cat. # PVP10) was dissolved in 40 ml of DI water (18 Mohm-cm) and to this was added 0.0246 g (0.145 mmol) of silver nitrate (≥99.0% ACS reagent Sigma Aldrich Cat. #209139). To this pale yellow solution was added 0.0350 g (0.145 mmol) of copper nitrate trihydrate, (≥98% Sigma Aldrich Cat. #61197), to give a dark yellow solution. In a separate vessel 0.0481 g (0.29 mmol) of potassium iodide, (≥99.0% ACS reagent Sigma Aldrich Cat. #60400), was dissolved in 10 ml DI water (18 Mohm-cm) and added drop wise (0.34 ml/minute) to the silver, copper nitrate PVP solution. This resulted in a pale yellow dispersion of a solid solution of silver-copper iodide ($Ag_{0.5}Cu_{0.5}I$). Dynamic light scattering on a dilute sample of the dispersion gave a mean particle size of 29 nm.

Silver-copper-bromide nanoparticles were synthesized following the same procedure as for silver-copper-iodide using KBr instead of KI. Silver-copper-iodide-bromide nanoparticles were prepared in the same fashion using a combination of KI and KBr in a (1-y):(y) mole ratio.

Example 11: Synthesis of $Ag_{0.25}Cu_{0.75}I$ Nanoparticles

Nano-particle dispersion of silver copper iodide solid was prepared according to Example #10 except that the molar concentrations of the metal ions were adjusted according to the formula $Ag_{0.25}Cu_{0.75}I$. Dynamic light scattering of a dilute sample of the dispersion gave a mean particle size of 10 nm. In this example, $Ag_{0.25}Cu_{0.75}I$ may be considered a solid solution of CuI and AgI where both are present in molar ratio of 25% AgI and 75% CuI, or one may consider CuI is about 71% by weight and AgI is 29% by weight.

Example 12: Synthesis of $Ag_{0.75}Cu_{0.25}I$ Nanoparticles and Antimicrobial Activity of $Ag_xCu_{1-x}I$ Nano-particle dispersion of silver copper iodide solid was prepared according to Example 10 except that the molar concentrations of the metal ions were adjusted according to the formula $Ag_{0.75}Cu_{0.25}I$. Dynamic light scattering of a dilute sample of the dispersion gave a mean particle size of 8 nm. In this example, $Ag_{0.75}Cu_{0.25}I$ may be considered a solid solution of CuI and AgI where both are present in molar ratio of 75% AgI and 25% CuI, or one may consider CuI is about 21% by weight and AgI is 79% by weight.

Figure 2:
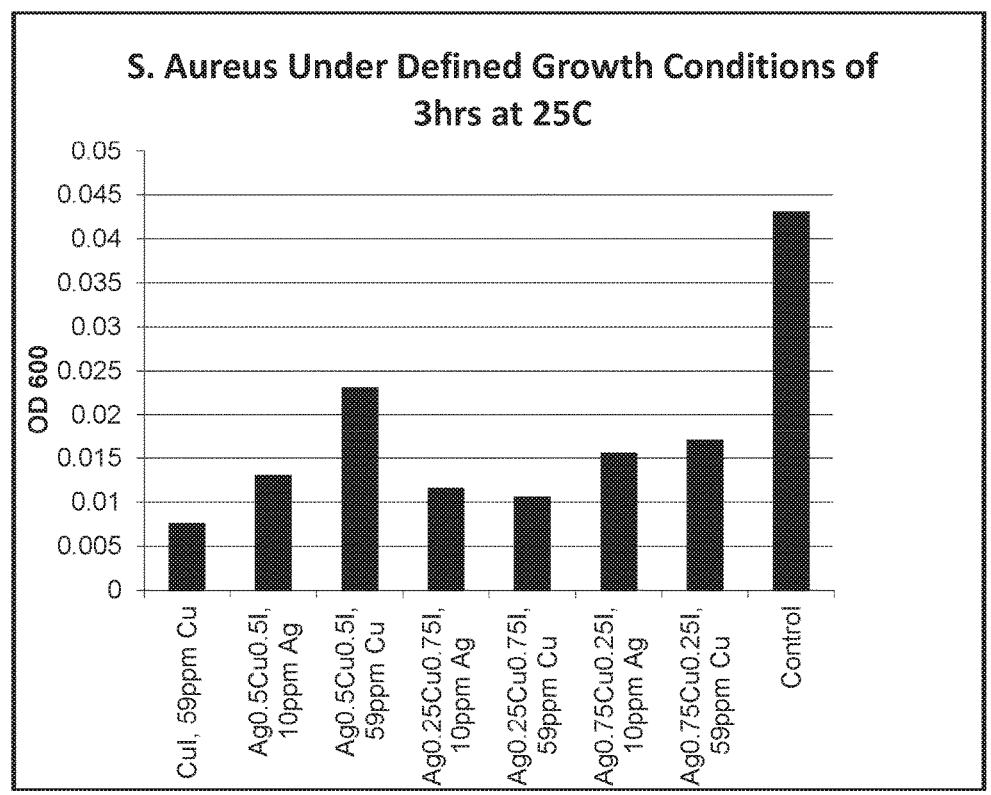
FIG. 2 is a plot of Optical Density (OD, Y-axis) against *S. aureus* growth and/or inhibition by copper iodide particles and Ag—CuI mixed metal halides, and a control.

Antimicrobial testing of Ag—Cu mixed metal halides (made in Examples 10, 11 and this one, i.e., Example 12) and their performance comparison with CuI was done using optical density method. FIG. 1 is a plot bar chart of Optical Density (OD, Y-axis) as a measure of growth against the effect of copper iodide particles and Ag—CuI mixed metal halides, and a control. Optical density was measured after treating the bacterial solutions with the nanoparticles of mixed metal halides (or solid solutions of mixed metal halides). Lower optical density implies growth inhibition and showed higher effectiveness. $Ag_{0.25}Cu_{0.75}I$, $Ag_{0.5}Cu_{0.5}I$, and $Ag_{0.75}Cu_{0.25}I$ all showed effective antimicrobial properties against P. aureginosa (FIG. 1) and S. aureus (FIG. 2), however, none were as effective as CuI nanoparticles alone (CuI was made as in Example 5 by using the acetonitrile process). The data shows that with increasing copper content in the solid solution the efficacy of the material increased.

Example 13: Infusion of Metal and Inorganic Metal Compounds into Porous Particles The copper halide-porous particle composition is demonstrated by two process embodiments which were used to infuse copper halide into porous silica carrier particles. Various types of porous silica particles were used from Silicycle Inc. (Quebec City, Canada). These were IMPAQ® angular silica gel B10007B hydrophilic silica. They had average particle size of 10 μm and a pore size of 6 nm, with pore volume of about 0.8 ml/g and a surface area of >450 m$^2$/g; or silica with particle size of 0 to 20 μm range (pore size 6 nm, surface area 500 m$^2$/g); or silica 0.5 to 3 μm in range (product number R10003B, pore size 6 nm).

Method 1

0.6 g of CuI (from Sigma Aldrich, 98.5% purity) was dissolved in 20 ml acetonitrile at room temperature (use of about 0.68 g of CuI would have saturated the solution). 1 g of silica powder (0-20 μm) was added to this solution. The solution was stirred for three hours at room temperature (this time period could have varied from a few seconds to more than three hours), then filtered through 0.45 μm nylon filter (from Micron Separations Inc., Westboro, Mass.) and finally dried at 70° C. The process may be repeated to increase the halide content. Using a spatula, the material is easily broken down into a fine powder. The analysis of this silica using inductively coupled plasma (ICP) atomic absorption spectroscopy at a commercial laboratory showed that the copper by weight was 1.88% of silica.

Example 14: Infusion of Metal and Inorganic Metal Compounds into Porous Particles: Method 2

In this method the solvent for CuI was 3.5 M KI solution in water. KI solution was prepared by dissolving 29 g of KI in 40 ml of deionized water, stirring and adding water to complete a final volume of 50 ml. The volume of the KI solution after mixing was measured to be 50 ml. 1.52 g of CuI was added and stirred at room temperature. The solution turned yellow immediately and by the next day it darkened somewhat. To 6 ml of this solution, 0.5 g of porous silica carrier particles (0.5 to 3 μm) were added and stirred for six hours. The silica particles were filtered and were then added to water so as to precipitate CuI trapped on the surface of the silica. The analysis of this silica using ICP AA instrument showed that the copper by weight was 1.46% of silica.

Example 15: Preparation of Polyurethane/CuI Dispersions by Wet Grinding

The samples were ground in a wet grinding mill produced by Netzsch Premier Technologies LLC (Exton Pa.), equipment model was Minicer®. The grinding beads were made of YTZ ceramic (300 μm in diameter). The interior of the mill was also ceramic lined. 99.9% purity CuI was used to be ground to finer particle size using aqueous media. Two different types of aqueous media were used. In the first case the material was an aliphatic urethane 71/N aqueous dispersions (35% solids) sold under the Tradename of ESACOTE® obtained from Lamberti SpA, (Gallarate, Italy). This material is used for aqueous furniture varnishes and also for metal coatings. The second material was a PVP (Aldrich molecular weight 10,000) solution in water.

For the polyurethane dispersion, 10 g of copper iodide was added for every 100 ml of dispersion. As the grinding proceeded, the viscosity increased and the dispersion was diluted with a mixture of 7% n-ethyl pyrrolidone and 93% water by weight. 60 ml of diluents was added throughout the process. The samples started out with 50 grams CuI and 500 grams of the PU dispersion. It should be noted that the surface of the ground particles was being functionalized by the PU dispersion (which comprised of hydrophobic polyurethane and a surfactant amongst other additives). A total of 60 grams of 7% 1-ethyl-2-pyrrolidone was added periodically throughout the milling process as follows: 25 grams at 75 minutes, 10 grams at 105 minutes, 15 grams at 120 minutes, and 10 grams at 150 minutes. Approximately 100 mL of product was taken out of the mill at 75 and 105 minutes (before the addition of the solvent), and the remainder was pumped out at the 210 minute mark. At the end the process, the total solids content including CuI was 35%, the polymeric content was 27.2% and the % of CuI to that of the polymer was 28.6%. During grinding the maximum temperature was 38° C. After 210 minutes of grinding, the particle size was measured. The circulation speed and agitation speed settings on the equipment were both at six. Particle size measurement was conducted by HORIBA Laser Scattering Particle Size Distribution Analyzer (model LA-950A). The average particle size was 68 nm with a standard deviation of 7.4 nm. To test the stability of the suspension with ground particles, the particle size was measured again the next day which gave the mean size as 70 nm with a standard deviation of 8.2 nm.

Example 16: Preparation of PVP/CuI Dispersions by Wet Grinding

For the PVP dispersion, the formulation was 480 grams: 20 grams CuI, 60 grams PVP (Aldrich 10,000 MW), 400 grams de-ionized water. Grinding parameters were the same as in Example 15. Samples were pulled out after 45, 120 and 210 minutes of grinding under the same conditions as above (Example 15), the particle size (mean size) was respectively 920 nm (bimodal distribution with peaks at 170 and 1,500 nm), 220 nm and 120 nm respectively, when measured using the HORIBA apparatus as described above.

Example 17: Effect of CuI Particles on Inhibiting the Growth of Spores

Figure 3:
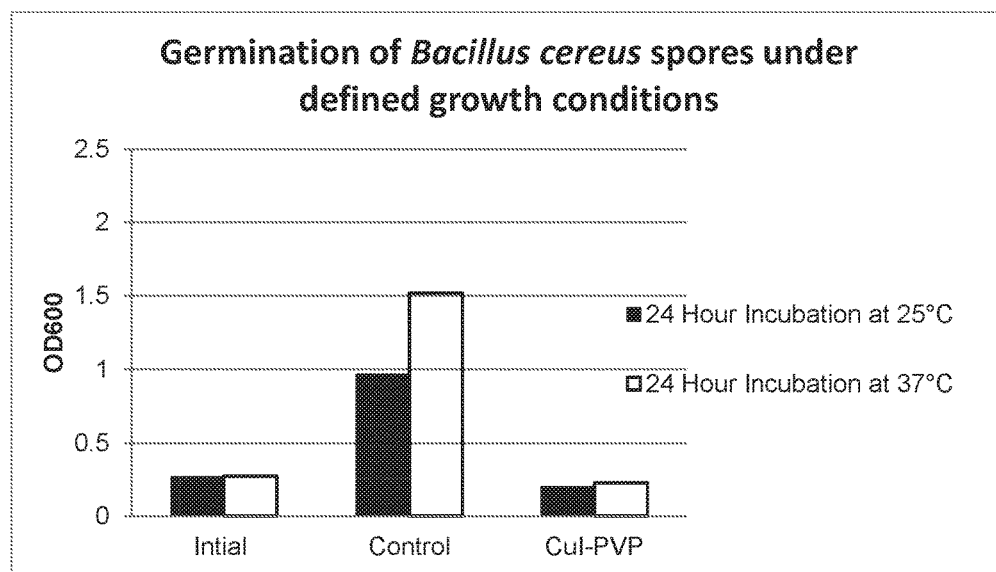
FIG. 3 is a bar chart showing the effectiveness of CuI against the growth of *Bacillus cereus* spores.

FIG. 3 is a bar chart that shows the effect of CuI/PVP inhibition on *B. cereus* spores growth. CuI/PVP suspensions were made as in Example 5, and the copper concentration was 59 ppm in the final medium comprising CuI/PVP and the bacterial broth. This figure clearly shows the effectiveness of CuI/PVP in preventing *B. cereus* spores growth, and in fact even achieving a slight reduction as compared to the starting spore concentration.

Examples 18-23 Additional Antimicrobial Results Using Particulate Suspensions

Antimicrobial testing was carried out on the following microbes:

Ex. 18—*Pseudomonas aeruginosa* (ATCC 27313) (Table 5)

Ex. 19—*Staphylococcus aureus* (ATCC 25923) (Tables 6)

Ex. 20—*Streptococcus mutans* (ATCC 25175) (Table 7)

Ex. 21—*S. enterica Typhimurium* (ATCC 23564) (Table 8)

Ex. 22—*Penicillium* (Table 9)

Ex. 23—*Aspergillus niger* (Table 10)

Table 4 is a list of samples, particle sizes and functionalization used in subsequent tables 5-10 with antimicrobial results. The particle size in this table was measured using dynamic light scattering (here and above, unless mentioned otherwise). In some cases the particle size was confirmed by optical absorption or by scanning electron microscopy (SEM). For measurement by dynamic light scattering, the particle suspensions were diluted in DI water by taking one to two drops of the suspension and adding several ml of water to ensure that a clear (to the eye) solution was obtained in a 1 cm path length cuvette. If the particles were large, the solutions were stirred just before measurement. Several measurements were made to ensure repeatability and reproducibility of samples. Most measurements were carried out using a Malvern Zetasizer Nano ZS light scattering analyzer (available from Malvern Inc, Westborough, Mass.) at ambient temperature, with a backscatter mode at a 173° scattering angle or using DynaPro NanoStar by Wyatt Technologies (Santa Barbara, Calif.), with a Laser Wavelength (nm)=661). Commercial polystyrene spheres with known size (60 nm) were used for instrument calibration. Some of the measurements were also made on the Nanotrac particle analyzer (available from Microtrac Inc, Montgomeryville, Pa.), also in the backscattering mode using a fiberoptic probe. The data was converted and reported in the volume fraction mode.

TABLE 4

| Sample number | Preparation method (Example#) | Metal or halide (CuI purity, %) | Surface Modification | Particle size*, nm |
|---|---|---|---|---|
| S10 | 4 | AgBr | PVP-Aldrich | 4 E |
| S11 | 3 | Ag | PVP-Aldrich | 7 E |
| S12 | 5 | CuI (98) | PVP-Aldrich | >15 E |
| S13 | 10 | Ag$_{0.5}$Cu$_{0.5}$I | PVP-Aldrich | 29 |
| S14 | 5 | CuI (98) | PVP-Aldrich | >30 E |
| S16 | | | | |
| S17 | 5 | CuI (98) | PVP-Aldrich | 4 E |
| S18 | 4 | AgBr | PVP-Aldrich | 4 E |
| S19 | 4 | AgBr | PVP-Aldrich | 4 E |
| S26 | 5 | CuI (98) | PVP-Aldrich | 4 E |
| S28 | 8 | CuI (99.999) | VP-VA Copolymer-BASF + HNO$_3$ | 4 E |
| S33 | 5 | CuI (98) | PVP-BASF | 5 |
| S34 | 2 | CuI (99.999) | PEG(10k, Aldrich) + HNO$_3$ | 4 E |
| S34 | 6 | CuCl | PVP-BASF | 4 to 10 E |
| S35 | 3 | Ag | PVP-Aldrich | 6 |
| S36 | 4 | AgBr | PVP-Aldrich | 4 E |
| S37 | Purchased | AgI | PVP (AgI nano from ChemPilots) | 25 |
| S38 | 9 | CuI (99.999) | PVP-BASF + HNO$_3$ | 4 |
| S39 | 6 | CuCl | PVP-BASF | <10 E |
| S40 | | No AM material | Porous silica | Silica 0.5 to 3 μm |
| S41 | 13 (1) | CuI (98.5) | Porous silica | Silica 0 to 20 μm |
| S42 | 13 (2) | CuI (98.5) | Porous silica, | Silica 0.5 to 3 μm |
| S43 | 5 | CuI (98) | PVP-Aldrich | 6 |
| S51 | 16 | CuI (99.5%) | PVP-Aldrich (Ground) | 120 |
| S52 | 16 | CuI (99.5%) | PVP-Aldrich (Ground) | 220 |
| S53 | 16 | CuI (99.5%) | PVP-Aldrich (Ground) | 920 (bimodal 170 and 1,500 nm) |

*"E" stands for those particles whose size was estimated. Estimated particle size is based on comparison to previously measured particle sizes for particles made according to the same process.

Example 18: Efficacy Against *P. aeruginosa* of Various Functionalized Particles Table 5 shows the reduction of *P. aeruginosa* by exposure to various type of metal halide particles and their combinations, and also in different concentrations, sizes and surface modifications. All of these were tested with controls (meaning without metal halide particles or other known antimicrobial materials). The results from control are not shown, as they all uniformly showed either no growth or moderate growth of microbes under the same conditions. Experiments were conducted in duplicate. Further, in many cases, e.g., in Table 5, result R11 (at 24 hr), the results show >4.41 log reduction. In the same table at 24 hrs the result R40 also shows >5.19 log reduction. This does not imply that the result in the second case is more effective than in the first, all it says is that given a starting concentration of microbes, at that point there were too few too count. Thus use of the symbol ">" in all of these tables means that the maximum log reduction for that experiment was reached. That is to say, after the indicated time, there were no viable microbes seen. Sample number (starting with "S" in column 2) when stated will correspond to the sample number in Table 4. If exactly the same result number (Column 1, starting with "R") is used in various tables (Tables 5 to 10), then that corresponds to the same formulation and batch being tested for different microbes. For example R28 result in Table 5 was obtained on *P. aeruginosa*, and the same suspension was used to obtain the R28 result against *S. aureus* in Table 6.

TABLE 5

| | | | | *P. aeruginosa* | | | | | |
|---|---|---|---|---|---|---|---|---|---|
| | | | Conc, PPM, | Time | | | | | |
| Result | Sample # | Particles | Ag, Cu | 15 min | 30 min | 1 hr | 2 hr | 6 hr | 24 hr |
| R7 | S12 | CuI | 0, 59 | 4.32 | >4.47 | >4.47 | >4.47 | | |
| R8 | S11 + S12 | Ag + CuI | 10, 59 | >4.47 | >4.17 | >4.47 | >4.47 | | |
| R9 | S10 + S12 | AgBr + CuI | 10, 59 | 4.17 | >4.47 | >4.47 | >4.47 | | |
| R10 | S11 + S12 | Ag + CuI | 10, 6 | 0.09 | 0.07 | 0.08 | 0.20 | | |
| R11 | S12 | CuI | 0, 12 | 0.31 | 0.33 | 0.33 | 0.42 | 1.22 | >4.41 |
| R12 | S11 + S12 | Ag + CuI | 2, 12 | 0.3 | 0.3 | 0.42 | 0.46 | 1.32 | >4.41 |
| R13 | S10 + S12 | AgBr + CuI | 2, 12 | 0.34 | 0.25 | 0.34 | 0.41 | 1.13 | >4.41 |
| R14 | S11 + S12 | Ag + CuI | 10, 59 | 2.35 | >4.41 | >4.41 | >4.41 | >4.41 | >4.41 |
| R23 | S17 | CuI | 0, 59 | 2.30 | 2.97 | 3.81 | 4.76 | >4.77 | |
| R26 | S26 | CuI | 0, 59 | >4.65 | >4.65 | >4.65 | >4.65 | >4.65 | |
| R28 | S28 | CuI | 0, 59 | >6.76 | >6.76 | >6.76 | >6.76 | >6.76 | |
| R30 | S32 | CuI | 0, 59 | 4.11 | >4.78 | 4.36 | 4.54 | >4.78 | |
| R31 | S33 | CuI | 0, 59 | >4.19 | >4.48 | 4.63 | >4.78 | >4.63 | |
| R32 | S35 | Ag | 60, 0 | 0.05 | | −0.05 | −0.02 | 0.06 | 1.57 |
| R33 | S36 | AgBr | 60, 0 | 0.01 | | −0.11 | −0.01 | 0.15 | 3.67 |
| R34 | S37 | AgI | 60, 0 | 0.01 | | 0.01 | 0.06 | 0.19 | 0.29 |
| R35 | S38 | CuI | 0, 60 | >4.56 | | >4.56 | >4.56 | >4.56 | >4.56 |
| R36 | S39 | CuCl | 0, 60 | 0.05 | | 0.03 | 0.19 | 0.47 | 1.21 |
| R37 | S40 | No AM material | 0, 0 | 0.24 | | 0.2 | | 0.04 | 0.02 |
| R38 | S41 | CuI | 0, 19 | 0.97 | | 2.32 | | >4.59 | 3.58 |
| R39 | S42 | CuI | 0, 15 | 1.50 | | 3.89 | | >5.16 | 4.57 |
| R40 | S43 | CuI | 0, 59 | >5.04 | | >5.19 | | >5.19 | >5.19 |

TABLE 5-continued

| | | | *P. aeruginosa* | | | | | | | |
|---|---|---|---|---|---|---|---|---|---|---|
| | | | Conc, PPM, | Time | | | | | | |
| Result | Sample # | Particles | Ag, Cu | 15 min | 30 min | 1 hr | 2 hr | 6 hr | 24 hr | |
| R48 | S51 | CuI | 0, 59 | >4.53 | | >4.53 | | >4.53 | >4.53 | |
| R49 | S52 | CuI | 0, 59 | 4.38 | | >4.53 | | >4.53 | >4.53 | |
| R50 | S53 | CuI | 0, 59 | 3.91 | | 3.84 | | >4.53 | >4.53 | |

Results on *P. aeruginosa*, a gram negative bacterium, are shown in Table 5. Result R9 in this table shows that efficacy at much shorter times, i.e., at 15 minutes is surprisingly high. This high efficacy is seen even in those formulations where only CuI is used, such as in R7. All of the above formulations use suspensions with a copper concentration of 59 ppm.

When the copper concentration is dropped to 12 ppm, such as in R11, the efficacy at short times suffers, but one is still able to achieve high efficacy at 24 hrs. Addition of silver as silver metal or silver bromide to copper iodide (compare R11 to R12 or R13; or compare R7 to R8 or R9), does not improve the efficacy, showing that CuI by itself is quite effective.

Further, for *P. aeruginosa*, different surface modifications were used on CuI, such as PVP from Aldrich, PVP from BASF, VP-VA copolymer from BASF, Polyethylene glycol, and even acids for surface peptization (see results R26 to R31), and all of these show that each of these suspensions were maximally effective. Comparison of results \One may also mix different metal halides or metal halide and a metal, and also particles with different surface modifications with high efficacy against *P. aeruginosa* as shown in numerous results in this table.

Results R32 to R36 compare particles of various silver salts (AgBr and AgI), silver metal and various copper salts (CuCl and CuI), all of these surface modified with PVP and by themselves only, and all of them at metal concentration of 60 ppm. This data clearly shows CuI has the highest efficacy and the other materials show lower efficacy against this microbe.

Results R37 through R39 were on porous silica particles. R37 was for silica particles with a size in the range of 0.5 to 3 μm which do not have any CuI. Result R38 was for silica particles with a size in the range of 0 to 20 μm which had CuI infused by the method of Example 13 (method 1). The copper metal content in these particles was 1.9% by weight. Result R39 was for silica particles with a size in the range of 0.5 to 3 μm which had CuI infused by the method in Example 14 (method 2). The copper metal content in these particles was 1.5% by weight. These were tested for antimicrobial effect in a suspension, where the silica particles were added with and without CuI. The copper concentration in samples R38 and R39 was 19 and 15 ppm respectively. As expected the sample without antimicrobial additive (result R37) did not show antimicrobial properties. The other two showed a high efficacy.

Results R48 to R50 (on samples S51 to S53 respectively) are the results of suspension testing of particles made by wet grinding in the presence of PVP comprising an aqueous solution using the process described in Example 16. These three samples were obtained from the same run but extracted at different periods of grinding. The average particle size of these three samples was 120, 220 and 920 nm respectively. The last sample, S53 with an average particle size of 920 nm, had a bimodal distribution with particles average sizes peaking at 170 and 1,500 nm. All of these show high antimicrobial efficacy, with the smallest particle size sample (Result R48 on Sample S51) showing a great efficacy at shorter time periods.

Example 19: Efficacy Against *S. aureus* of Various Functionalized Nanoparticles

TABLE 6

| | | | *S. aureus* | | | | | | |
|---|---|---|---|---|---|---|---|---|---|
| | | | Conc, PPM, | Time | | | | | |
| Result# | Sample # | Particles | Ag, Cu | 15 min | 30 min | 1 hr | 2 hr | 6 hr | 24 hr |
| R7 | S12 | CuI | 0, 59 | >4.07 | >4.31 | >4.31 | >4.31 | | |
| R8 | S11 + S12 | Ag + CuI | 10, 59 | >4.31 | >4.31 | >4.31 | >4.31 | | |
| R9 | S10 + S12 | AgBr + CuI | 10, 59 | >4.31 | >4.31 | 4.07 | >4.31 | | |
| R10 | S11 + S12 | Ag + CuI | 10, 6 | 0.05 | 0.04 | 0.06 | 0.09 | | |
| R11 | 12 | CuI | 0, 12 | 0.79 | 0.95 | 1.35 | 1.81 | 2.96 | >4.34 |
| R12 | S11 + S12 | Ag + CuI | 2, 12 | 0.69 | 0.88 | 1.20 | 1.66 | 3.16 | >4.34 |
| R13 | S10 + S12 | AgBr + CuI | 2, 12 | 0.79 | 1.04 | 1.30 | 1.71 | 3.03 | >4.34 |
| R14 | S11 + S12 | Ag + CuI | 10, 59 | 0.58 | 2.71 | >4.34 | >4.34 | >4.34 | >4.34 |
| R28 | S28 | CuI | 0, 59 | >6.47 | >6.47 | >6.05 | >6.47 | >6.47 | >6.47 |

Table 6 shows results from similar experimentation on *S. aureus*, a gram positive bacterium responsible for common staph infections. CuI in small particle size by itself or mixed with silver metal or silver bromide was highly effective as seen in results R7, R8 and R9. Similar conclusion for *S. aureus* as for *P. aeruginosa* can be drawn on concentration of the compounds, mixture of different metal halides or metal halide and a metal, and particles with different surface modifications.

Example 20: Efficacy Against *S. mutans* of Various Functionalized Particles

TABLE 7

| | | | Conc, PPM, | Time | | | | | |
|---|---|---|---|---|---|---|---|---|---|
| Result# | Sample # | Particles | Ag, Cu | 15 min | 30 min | 1 hr | 2 hr | 6 hr | 24 hr |
| R27 | S27 | CuI | 0, 59 | >4.75 | >4.75 | >4.60 | >4.75 | >4.75 | >4.75 |
| R28 | S28 | CuI | 0, 59 | >4.75 | >4.75 | >4.75 | >4.75 | >4.75 | >4.75 |

To test the broad efficacy of metal halides, and in particular for copper iodide, we also tested functionalized particles of this material against several other microbes. One of these is a strep bacterium *S. mutans*, commonly found in mouth infections. R27 and R28 in Table 7 shows that CuI particles modified with PVP and the copolymer (VP-VA) both resulted in effective reduction of populations of this bacteria.

Example 21: Efficacy Against *S. enterica* Typhimurium of Various Functionalized Nanoparticles

TABLE 8

| | | | Conc, PPM, | Time | | | | |
|---|---|---|---|---|---|---|---|---|
| Result# | Sample # | Particles | Ag, Cu | 15 min | 30 min | 1 hr | 2 hr | 6 hr | 24 hr |
| R23 | S17 | CuI | 0, 59 | >4.85 | >4.85 | >4.85 | >4.85 | >4.85 | |

Table 8 shows that at 59 ppm, CuI surface modified with PVP showed a high degree of effectiveness (R23) against the microbe *S. enterica* when used alone or in combination with AgBr modified with thiomalic and aspartic acids (R16). This was more effective as compared to AgBr alone with a silver concentration of 10 ppm in the suspension (R15).

Example 22: Efficacy Against *Penicillium* of Various Functionalized Nanoparticles

TABLE 9

| | | | Conc, PPM, | Time | | | |
|---|---|---|---|---|---|---|---|
| Experiment # | Sample # | Particles | Ag, Cu | 24 hr | 48 hr | 72 hr | 96 hr |
| R27 | S27 | CuI | 0, 59 | >3.98 | >3.98 | >3.98 | >3.98 |
| R28 | S28 | CuI | 0, 59 | >3.98 | >3.98 | >3.98 | >3.98 |

To examine the effectiveness of the inorganic metal salts against molds, experiments were done against *Penicillium* as shown in Table 9. R27 and R28 in this table show that CuI particles modified with PVP and the copolymer (VP-VA) both resulted in effective reduction of this mold.

Example 23: Efficacy Against *A. niger* of Various Functionalized Nanoparticles

Table 10 shows the results for another mold *A. niger*. The strongest response is shown by CuI (R35) by itself.

TABLE 10

| | | | Conc, PPM, | Time | | | | |
|---|---|---|---|---|---|---|---|---|
| Result # | Sample # | Particles | Ag, Cu | 6 hr | 24 hr | 48 hr | 72 hr | 96 hr |
| R33 | S11 | Ag | 50, 0 | −0.09 | −0.01 | 0.01 | 0.00 | −0.16 |
| R34 | S10 | AgBr | 50, 0 | 0.06 | −0.14 | 0.16 | 0.21 | 0.15 |
| R35 | S14 | CuI | 0, 295 | 0.06 | 0.82 | 0.77 | 1.43 | 1.99 |
| R36 | S10 + S14 | AgBr + CuI | 50, 295 | −0.02 | 0.39 | 0.78 | 0.62 | 0.81 |

Example 24: Preparation of Coatings with CuI and their Antimicrobial Testing

Materials and Methods

For this example two sources for CuI were used. The first was bulk copper iodide powder (99.5% Sigma Aldrich) and the second nano-particles of CuI functionalized with PVP prepared from the acetonitrile process and isolated as a dry powder. For the nano-particles two high loadings of CuI in PVP were prepared namely 60 and 50 wt % CuI in PVP. The CuI used was 99.5% from Sigma Aldrich and the PVP was 10,000 MW from Sigma Aldrich. A typical high loading preparation was as follows.

To a liter pear shaped flask fitted with a stir bar was added 4.05 g of CuI powder and 300 ml of anhydrous acetonitrile. This was stirred to give a pale yellow solution. In a separate flask fitted with a stir were added 4.05 g of PVP and 200 ml of anhydrous acetonitrile. This was stirred for 2 hours to give a straw yellow colored solution. While stirring the CuI solution the PVP solution was slowly added to it to give a transparent yellow solution. Upon stirring at room temperature this solution slowly turned a light green color; this took about one hour for completion. This solution was dried under reduced pressure at 30° C. to form a light green powder with a CuI content of 50 wt %. This procedure was repeated except the initial CuI concentration was increased to 6.07 g to give a concentration of CuI in the powder of 60 wt %.

Preparation of Urethane Coating Containing CuI

To a beaker was added 5 g of an aliphatic urethane 71/N aqueous dispersions (35% solids, maximum viscosity 200 cP) sold under the tradename of ESACOTE obtained from Lamberti SpA, (Gallarate, Italy). To this was added 0.118 g of CuI powder (99.5% from Sigma Aldrich, particles not functionalized). This was stirred vigorously and 0.1 g of the cross linking agent PZ28 (Polyfunctional Aziridine manufactured by PolyAziridine, LLC Medford, N.J.) was added to the coating formulation. The urethane coating was applied to stainless steel substrates 2"×2" by brush application and cured at room temperature for 12 hours followed by two hours at 70° C. The cured coating was transparent with a slight brown tint. It was durable and hard with good chemical resistance to both water and ethanol. The $Cu^+$ content of the dried coating was 2.0 wt %. This procedure was repeated except using the nano-powders of CuI described above to give coated surfaces with different concentrations/types of $Cu^+$. These coated substrates were tested for antimicrobial activity against *P. aeruginosa* using a method as described below. As a comparison point a metal coated with DuPont antimicrobial (commercial powder coating) ALESTA™ was also tested (obtained from Dupont, Inc. (Industrial Coatings Division, Wilmington, Del.)). The antimicrobial materials in these coatings were zeolite particles (about 2 to 3 µm in size) infused with silver and zinc ions.

Test coupons (50×50 mm) were prepared by spraying with 70% ethanol to reduce bacterial background presence. Sample coupons were allowed to air dry before re-spraying with 70% ethanol and allowed to dry completely before testing. Polyethylene (PE) cover slips (40×40 mm) were sterilized via bactericidal UV for 30 minutes per side. These polymer coated surfaces were tested as discussed earlier using JIS Z2801-2000. The coating compositions and the results are summarized in Table 11.

These results show that functionalized CuI particles delivered significantly better antimicrobial performance as compared to the commercial antimicrobial coating, especially at the 6-hour mark. It is notable that the use of CuI (as received) as non-functionalized particles in the coatings when used at about 2 µm in size did not result in any perceived antimicrobial activity (see also Table 12, where coatings containing 1% or less $Cu^+$ comprising functionalized nanoparticles were notably antimicrobial).

Example 25: Preparation of Urethane Coatings Containing Wet Ground CuI Dispersion in Urethane (Emulsion) Resin A sample of liphatic urethane 71/N aqueous dispersion was divided in two parts. In one part CuI was added and ground to a small particle size for a duration of 240 minutes as described in Example 15 so that the smaller CuI particles being formed were functionalized by the PU dispersion. These two parts were then mixed in different proportions to vary the amount of copper in the coating formulation. As an example a formulation where these were mixed in a proportion of 50% each by weight was made as follows. To a beaker was added 3 g of an aliphatic urethane 71/N aqueous dispersion was added 3 g of the CuI comprising dispersion. This was mixed well to form a homogeneous material. While stirring 0.12 g of the cross linking agent PZ28 (polyfunctional aziridine manufactured by PolyAziridine, LLC Medford, N.J.) was added to this mixture. The urethane formulation was applied to stainless steel substrates 2"×2" by brush application and cured at room temperature for 12 hours followed by two hours at 70° C. The cured formulation was transparent with a slight brown tint. It was durable and hard with good chemical resistance to both water and ethanol. The $Cu^+$ content of the dried coating was 3.51 wt %. This procedure was repeated by varying the ratio of PU71/N to CuI urethane dispersion to give coated surfaces with different concentrations of $Cu^+$ as listed in Table 12. These were tested against *P. aeruginosa* as described in the above example, and the results are shown in Table 12. In this example, it should be emphasized that polyurethane 71/N aqueous dispersion is an emulsion of a hydrophobic urethane, as after it is coated and dried, this cannot be solvated in water.

TABLE 11

| Wt % $Cu^+$ in Coating | Type of CuI used | Particle size* | $Log_{10}$ Reduction (*P. aeruginosa*) 6 hr | 24 hr |
|---|---|---|---|---|
| 2.0 | Bulk Powder (99.5%) | 1 to 2 µm | 0.31 ± 0.03 | 0.29 ± 0.08 |
| 4.3 | CuI nanoparticles (60 wt % in PVP) | 254 nm | >5.69 ± 0.00 | >5.69 ± 0.00 |
| 3.0 | CuI nanoparticles (50 wt % in PVP) | 241 nm | >5.49 ± 0.17 | >5.69 ± 0.00 |
| 0.0 | None | | −0.02 ± 0.10 | −0.02 ± 0.05 |
| DuPont Crystal Clear AM coating | None | 2 to 3 µm | 0.89 ± 0.08 | 4.52 ± 0.00 |

*Particle size of CuI or the antimicrobial material (optical microscope used to characterize bulk powder).

TABLE 12

| Ratio PU:(CuI ± PU) (by weight) | Wt % Cu⁺ in Dried Coating | Log₁₀ Reduction 6 hours | Log₁₀ Reduction 24 hours |
|---|---|---|---|
| 10:90 | 6.33 | >6.08 ± 0.05 | >5.98 ± 0.05 |
| 50:50 | 3.51 | 3.24 ± 0.05 | >5.82 ± 0.05 |
| 75:25 | 1.76 | 3.71 ± 0.05 | >5.76 ± 0.05 |
| 90:10 | 0.70 | 3.24 ± 0.05 | >5.98 ± 0.05 |
| 100:0 | 0.00 | 0.55 ± 0.05 | −0.04 ± 0.08 |

The above results show that incorporation of functionalized CuI particles in coatings which were prepared by grinding in a polymeric emulsion process resulted in polymer-functionalized CuI particles having high antimicrobial activity. The polymeric emulsion functionalized the CuI surfaces and stabilized the particles as it was pulverized. PU coatings without the copper-based additive did not demonstrate antimicrobial properties, as demonstrated in the 100:0 result of Table 12. Further, the antimicrobial activity increased with the increased CuI content. It is interesting to note that all of these coatings with CuI had better performance at short times as compared to the commercial coating in Table 11. Further, sample with less than 5% CuI (the 90:10) formulation resulted in high antimicrobial efficacy.

Example 26: Povidone-Iodine Plus Copper Iodide/Polyvinylpyrrolidone Antimicrobial Solution A copper iodide polyvinylpyrrolidone (PVP) powder is prepared by dissolving 0.0476 g of CuI (99.999% Sigma Aldrich) in 50 ml of anhydrous acetonitrile. To this solution is added 10 g of PVP (10,000 MW Sigma Aldrich) and stirred to form a pale yellow solution. The acetonitrile is removed under reduced pressure at 30° C. to form a pale green powder. This powder contains 0.158 wt % Cu⁺.

To 10 ml of a 10% solution of Povidone-iodine (CVS brand, obtained from CVS Pharmacy, Tucson, Ariz.) is added 0.38 g of the CuI/PVP powder previously described to give a 60 ppm concentration of Cu⁺ in the solution. This forms the Povidone-iodine-CuI/PVP antimicrobial solution.

Example 27: Topical Cream Comprising CuI Nanoparticles: Zone of Inhibition

To prepare this cream, functionalized CuI particles with two different sizes were prepared in PVP.

For the first preparation, the particle size was 241 nm and was made by the procedure described in Example 24 which used 10,000 molecular weight PVP from Sigma Aldrich. This is called 50% Powder (as this had 50% by weight of CuI in the dry powder).

For the second preparation, the particle size was predominantly 4 nm and was prepared in the following fashion. To a reaction flask containing 80 ml of anhydrous acetonitrile, (99.8% Sigma Aldrich Cat. #271004), was added 4.75 g of PVP (Luvitec™ K17 from BASF) and stirred to form a light yellow solution. To this solution was added 0.25 g of CuI (99.999% Sigma Aldrich Cat. #205540) and after stirring for 30 minutes this resulted in a clear pale green solution. Then the bulk of the acetonitrile was removed under reduced pressure at 30° C. to form a viscous paste. The temperature was then increased to 60° C. to completely remove the solvent to give a pale yellow solid. Dynamic light scattering on a dilute sample of the dispersion showed a mean particle size of 4 nm for 85% of the particulate volume, and the others were larger. This had 5 weight % of CuI in the dry powder, and was called 5% Powder.

The cream was prepared in a beaker by adding 0.06 g of Carbomer (obtained from Lubrizol Inc, Wickliffe, Ohio) and 2.0 ml of deionized water (18 Mohm-cm). This was mixed to give a slightly hazy non colorless liquid. To this mixture was added 0.2 g of PVP (Sigma Aldrich, 10,000 molecular weight) and the mixture stirred vigorously. The addition of PVP caused a slight decrease in the viscosity. To this solution was added while stirring 1.96 g of CuI/PVP 50% Powder followed by 1.45 g of CuI/PVP 5% Powder. The final concentration of Cu⁺ in the cream was 2.1 wt %. This cream was tested against *P. aeruginosa* and *S. aureus* using the zone of inhibition method as described below.

Petri dishes for the test were prepared by dispensing 25 ml of sterile agar medium into sterile plates. Overnight cultures were diluted to final working optical density 600 nm of 0.100 and uniformly streaked over the agar using sterile swabs. Cylindrical plugs having a diameter of approximately 5.3 mm were removed from the solidified agar plates by means of a sterile cork borer. Approximately 75 μl of cream were added to the wells. Triple antibiotic first aid ointment from Walgreens Pharmacy (Walgreens Brand, obtained from Walgreens Pharmacy, Tucson, Ariz.) was used as a control material. This cream (control) listed Bacitracin zinc 400 units, Neomycin 3.5 mg and Polymyxin B sulfate at 5,000 units as active ingredients in white petrolatum. Plates as described were incubated in a humidified chamber at 37° C. for 24 hours at which time the plates were examined for bactericidal and growth inhibition effects.

Upon examination of the plates a slight bluish-green hue halo was observed around the wells along with a zone of inhibition for CuI comprising creams. A three scale measure was used to determine the zone of inhibition, "0" for no inhibition, which was indicated by complete absence of the zone of inhibition; "1" as limited inhibition, where the zone diameter (including the well) was in the range of 6 to 8 mm; and significant inhibition designated as "2", when this zone (including the well) exceeded 8 mm. The results are shown in Table 13 below.

TABLE 13

| Material | Inhibition against *P. aeruginosa* | Inhibition against *S. aureus* |
|---|---|---|
| Control | 0 | 2 |
| Cream with CuI | 2 | 2 |

The control cream is known to be effective against Gram positive microorganisms, and the results show the controls inhibited *S. aureus*, as expected. The CuI creams of the current formulation show equal effectiveness against *S. aureus*. Against the Gram negative *P. aeruginosa*, the control creams were not expected to show efficacy, and they did not. However, the CuI-based cream did show substantial effectiveness, further bolstering the broad antimicrobial nature of the invention.

Example 28: Preparation of CuI Particles Surface Modified by Sodiumdodecylsulfate (SDS) by Grinding Process CuI (99.5% from Aldrich) and SDS (Aldrich#436143) were used for this preparation. The same mill that was used in Example 15 was used to prepare this sample. The mill parameters were: 4200 RPM, Pump=600 RPM, Media used=100 µm diameter in YZT, Grinding time=1260 min Water was allowed to circulate with pump on at 25 rpm and the mill on at 1000 rpm while 94.2854 g CuI (99.5%), and 17.142 g SDS were added (85.7% CuI and 14.3% SDS). This was done to prevent overloading or clogging the mill. The pump and mill speed were then increased to 600 and 4200 respectively. This mixture was ground at these speeds for 1260 minutes using 4.13 kWh. A chiller was used to cool the slurry being ground. A pink mixture was removed from the mill and dried in a blowing furnace because the foaming action of SDS prevents drying on a rotary evaporator. The product was dried in a covered pan at 70° C. until the product was completely dry. This formed a pink/tan solid powder with a yield of 107 g (97.3% yield). Table 14 shows the particle size from dynamic light scattering measurements when this powder was redispersed in water. This table also shows the antimicrobial properties of the liquid suspension when tested at a copper concentration of 59 ppm. The particle size here is relatively large, which may have reduced its efficacy at shorter times as compared to the results in Tables 5 and 6.

TABLE 14

| Particle size (DSL) | | | Antimicrobial activity (59.07 ppm Cu), | |
|---|---|---|---|---|
| Particle Size | | | $\log_{10}$ reduction | |
| (nm) | % polydispersity | Time | P. aeruginosa | S. aureus |
| 372.2 | 59.4 | 15 min | 3.60 ± 0.21 | 1.53 ± 0.08 |
| | | 1 hr | 3.97 ± 0.30 | 3.57 ± 0.04 |
| | | 3 hr | >4.66 ± 0.00 | >4.50 ± 0.00 |
| | | 6 hr | >4.66 ± 0.00 | >4.50 ± 0.00 |

Example 29: Preparation of Precipitated Porous Silica Infused with CuI (a) Copper iodide (2 g, 99.5%, Aldrich) was added to a 250 ml round bottom flask along with a stir bar and acetonitrile (40 ml) to give a saturated solution. This saturated solution was then left to stir at room temperature for several hours. The resulting solution was a pale yellow color with a pale yellow precipitate.

(b) This CuI saturated solution was filtered via vacuum filtration using a 0.8 µm MAGNA, nylon, supported plain filter paper by Osmonics.

(c) The clear, pale yellow filtered solution was added to a clean 250 ml round bottom flask with a stir bar and 3.5 g of porous silica (Sipernat 22 LS, 9 µm in size, precipitated Silica with a specific surface area of 180 m²/g, obtained from Evonik Industries). This solution was stirred at 25° C. for one hour.

(d) The solution was again filtered via vacuum filtration using a 0.8 µm MAGNA, nylon, supported plain filter paper by Osmonics (Obtained from Fisher Scientific, Pittsburgh, Pa.). A white silica and CuI containing powder was collected and was left to dry overnight at 100° C.

(e) Copper iodide (2 g, 99.5%) was added to a 250 ml round bottom flask along with a stir bar and acetonitrile (40 ml) to give a saturated solution. This saturated solution was then left to stir at room temperature for several hours. The resulting solution was a pale yellow color with a pale yellow precipitate.

(f) This CuI saturated solution was filtered via vacuum filtration using a 0.8 µm MAGNA, nylon, supported plain filter paper by Osmonics.

(g) The clear, pale yellow filtered solution was added to a clean 250 ml round bottom flask with a stir bar and 3.5 g of porous silica+CuI which was prepared in step "d". This solution was stirred at 25° C. for one hour.

The solution was again filtered via vacuum filtration using a 0.8 µm MAGNA, nylon, supported plain filter paper by Osmonics. A white powder was collected and was left to dry overnight at 100° C. An analysis showed that this powder was 76.6% silica and 23.4% CuI. Its antimicrobial properties in a suspension at 59 ppm of Cu is shown in table 15, and it is likely that the availability of Cu+ ions from antimicrobial particles in porous particles is lower than from the assembly of individual nanoparticles, which leads to lower efficacy as compared to the results in Table 5

TABLE 15

| Antimicrobial activity (59.07 ppm Cu), $\log_{10}$ reduction | |
|---|---|
| Time | P. aeruginosa |
| 30 min | 3.23 ± 0.62 |
| 3 hrs | 2.96 ± 0.35 |

Example 30: Preparation and Testing of Antimicrobial Powder Coatings

The coatings were prepared by first dry blending the functionalized CuI particles (SDS functionalized particles as prepared in Example 28, or porous silica infused with CuI as prepared in Example 29) with a carboxylated polyester resin (Crylcoat 2471 obtained from Cytec, Woodland Park, N.J.) containing a crosslinking agent triglycidylisocyanurate (TGIC, obtained from Aal Chem, Grand rapids, Mich.), a flow/leveling agent Powdermate 570 (obtained from Troy Chemical, Newark, N.J.) and a degasser Powdermate 542 (obtained from Troy Chemical). The concentration of CuI was varied. This mixture was then extruded in a two zone temperature process (zone 1=109° C. and zone 2=86° C.) and roller cooled to form a ribbon. This ribbon was crushed and dry blended to form a fine powder. This powder was ultrasonically fed into a Corona gun for powder coating onto 2"×2"×0.025" aluminum coupons. The coated aluminum substrates were cured at 204° C. for ten minutes under ambient atmosphere. The various coatings had a thickness ranging from high 50 to 75 µm and had a gloss (at 60°) between 100.3 to 126.3). The antimicrobial results are shown in Table 17. These coatings are compared with coatings deposited from a commercial antimicrobial powder material Alesta PFC609S9A from Dupont (Experimental Station, Delaware) which was also deposited in a similar fashion as above on similar substrates. These coatings have silver and zinc ions to provide antimicrobial properties. All of these coatings with antimicrobial material (including the one from Dupont) resulted in antimicrobial surfaces. However, at shorter times, all of the coatings with CuI provided superior efficacy as seen by greater log reduction.

TABLE 17

| Sample | $Log_{10}$ reduction of the microbe | | | |
|---|---|---|---|---|
| | P. aeruginosa (6 Hrs) | P. aeruginosa (24 Hrs) | S. aureus (6 hrs) | S. aureus (24 hrs) |
| 0.25% Cu (with SDS) | >5.63 | >5.43 | >4.77 | >5.31 |
| 1.0% Cu (with SDS) | >5.63 | >5.83 | >5.72 | >5.31 |
| 3.0% Cu (with SDS) | >5.63 | >6.03 | >5.72 | >5.31 |
| 0.25% Cu (in Silica) | >5.53 | 4.34 | 5.23 | >5.31 |
| DuPont AM coating | 1.79 | 5.73 | 3.29 | 4.65 |
| Standard polyester resin (No AM) | −0.19 | −0.59 | 0.16 | 0.57 |

The samples were cleaned after the evaluation by rinsing them twice in ethanol, washing them with a dish washing liquid and followed by another two rinses in ethanol. The antimicrobial effectiveness of the samples was evaluated against S. aureus. The results are shown in Table 18 and demonstrate that the samples are durable to washing and repeated use.

TABLE 18

| Sample | $Log_{10}$ reduction of the microbe | |
|---|---|---|
| | S. aureus (6 hrs) | S. aureus (24 hrs) |
| 0.25% Cu (with SDS) | 4.58 | >4.65 |
| 1.0% Cu (with SDS) | >5.35 | >4.75 |
| 3.0% Cu (with SDS) | >5.35 | >4.65 |
| 0.25% Cu (in Silica) | 4.23 | >4.31 |
| Standard polyester resin (No AM) | −0.09 | 0.53 |

Another set of ground CuI/SLS was made where the proportion was 75/25 by weight. The grinding parameters were the same as in Example 28, but the grinding time was reduced to 300 minutes. This was added to the powder coatings as discussed above in a concentration of 0.25 and 0.05% Cu (as CuI). The coatings with 0.25% Cu had a slight haze, whereas coatings with 0.05% Cu were clear. The results on the 0.25% coatings are shown in Table 19.

TABLE 19

| Sample Traetment | $Log_{10}$ reduction of the microbe (S. aureus, ATCC#25923), 24 hours | | | |
|---|---|---|---|---|
| | Initial | Washed 1X | Washed 50 times | Washed 50 times and scratched |
| Washed with water | >4.21 | >4.31 | >4.31 | >4.31 |
| Washed with Windex ® | >4.21 | >4.31 | >4.31 | >3.91 |
| Washed with Pine-sol ® | >4.21 | >4.31 | >4.31 | >4.31 |
| Ultrasonicated in water for 5 minutes @ 20 KHz | >6.01 | >6.01 | | |

Pine-Sol® and Windex® are commercial cleaners made by Chlorox (Oakland, Calif.) and by S. C. Johnson (Racine, Wis.) respectively. Each wash cycle with cleaners comprised of spraying of cleaner and then covering the surface with a wipe by going in a zig-zag motion horizontally, vertically and then horizontally. The surfaces were scratched with heavy duty scour pads, Target Brand, Obtained from a Target store in Tucson, Ariz.

The results on coatings with 0.05% Cu are shown below in Table 20.

TABLE 20

| | $Log_{10}$ reduction of the microbe | | | |
|---|---|---|---|---|
| | S. Aureus (ATCC25923) | | P. Aeruginosa (ATCC 9027) | |
| Sample Type | 6 hrs | 24 hrs | 6 hrs | 24 hrs |
| Coating without antimicrobial additive | 0.9 | 1.37 | 0.39 | 0.01 |
| Coating with antimicrobial additive | >3.59 | >4.17 | >3.86 | >3.61 |
| Dupont AM coating | 1.82 | >4.17 | 2.27 | >4.16 |

The results ($Log_{10}$ Reduction) on coatings with 0.05% Cu and 0.25% Cu against salmonella (S. typimurium, ATCC#23564) are compared to coatings without antimicrobial (AM) agent in Table 21.

TABLE 21

| Time | Coating without AM | Coating with 0.05% Cu | Coating with 0.25% Cu |
|---|---|---|---|
| 6 hours | 0.06 ± 0.08 | 1.78 ± 0.25 | >4.59 ± 0.28 |
| 24 hours | 0.11 ± 0.03 | 2.64 ± 1.10 | >4.54 ± 0.35 |

Example 31: Formation of Functionalized Particles by Wet Grinding

The samples were ground in a wet grinding mill produced by Netzsch Premier Technologies LLC (Exton Pa.), equipment model was Minicer®. The grinding beads were made of YTZ ceramic. The interior of the mill was also ceramic lined. The materials used for these preparations are outlined in Table 22.

TABLE 22

| Material | Description |
|---|---|
| Material | Description |
| AuI | Gold iodide, Aldrich 398411 |
| AgI | Silver iodide, 204404 |
| Bioterge | Sodium capryl sulfonate (aq); BIOTERGE PAS-8S (obtained from Stepan, Northfield, IL) |
| Chitosan | Deacetylated chitin, medium molecular weight, Aldrich 448877 |
| CuI | Copper iodide 99.5% Aldrich 03140 |
| CuSCN | Copper thiocyanate, Aldrich 298212 |
| PEG | Polyethylene glycol CARBOWAX ™ SENTRY ™ PEG 8000 NF, FCC Grade; Macrogol 8000 Ph. Eur. Granular, (obtained from Dow Chemical, Midland, MI) |
| PVP-A | Polyvinylpyrrolidone Avg MW = 10,000, Aldrich PVP10 |
| PVP-B | Polyvinylpyrrolidone Avg MW = 10,000, Luvitex K17 57858045 (Obtained from BASF, Germany) |

TABLE 22-continued

| Material | Description |
| --- | --- |
| Material | Description |
| SDS | Sodium dodecyl sulfate, Aldrich 436143 |
| ZnO | Zinc oxide, Aldrich 251607 |
| H2O | Deionized water, 18 megaohm-cm |
| Ascorbic Acid | L-Ascorbic acid >99%, Aldrich 95210 |
| UV stabilizer | 2-Hydroxy-4-(octyloxy)benzophenone 98%, Aldrich 413151 |
| IPA | Isopropyl alcohol, 99.5% Aldrich 278475 |

Table 23 shows various samples which were processed along with the conditions under which these were made. During grinding operation, the grinding head was chilled using a coolant at 5° C. However, depending on the viscosity, volume of material being ground and grinding conditions the grinding liquid temperature varied between 10 and 30° C. The quantity of grinding beads was measured volumetrically as approximately 140 ml.

TABLE 23

| Sample | Solids Proportion by Weight % | | Total Solids (g) | Water (mL) | Mill (RPM) | Pump (RPM) | Media Size (mm) | Grinding Time (min) |
| --- | --- | --- | --- | --- | --- | --- | --- | --- |
| | Metal Compound, % | Functionalization agent(s), % | | | | | | |
| 1. CuI/PEG | CuI, 15 | PEG, 85 | 10 | 100 | 4200 | 600 | 0.1 | 960 |
| 2. CuI/PEG/SDS | CuI, 20 | PEG, 77.61; SDS, 2.39 | 10 | 100 | 4200 | 600 | 0.1 | 60 |
| 3. CuI/PVP | CuI, 0.47 | PVP-B, 99.53 | 60.29 | 300 | 3800 | 500 | 0.1 | 360 |
| 4. CuI/PVP | CuI, 10 | PVP-B, 90 | 10 | 100 | 4200 | 600 | 0.1 | 60 |
| 5. CuI/PVP/SDS | CuI, 20 | PVP-A, 77.61; SDS, 2.39 | 10 | 100 | 4200 | 600 | 0.1 | 300 |
| 6. CuI/SDS | CuI, 85.7 | SDS, 14.3 | 0.7 | 140 | 2500 | 350 | 0.3 | 420 |
| 7. CuSCN | CuSCN, 10 | PVP-A, 90 | 1 | 100 | 4200 | 600 | 0.1 | 172 |
| 8. AuI | AuI, 0.21 | PVP-A, 99.79 | 5.01 | 100 | 4200 | 600 | 0.1 | 120 |
| 9. AgI | AgI, 10 | PVP-A, 90 | 10 | 100 | 4200 | 600 | 0.1 | 1070 |
| 10. ZnO | ZnO, 10 | PVP-B, 90 | 10 | 100 | 4200 | 600 | 0.1 | 60 |
| 11. CuI/CH (Chitosan) | CuI, 50 | Chitosan, 50 | 2 | 100 mL + 2 g acetic acid | 4200 | 600 | 0.1 | 60 |
| 12. CuI/CH/PVP | CuI, 10 | Chitosan, 10; PVP-B, 80 | 10 | 100 mL + 1.5 g acetic acid | 4200 | 600 | 0.1 | 60 |
| 13. CuI/PEG/Bioterge | CuI, 85.7 | Bioterge, 4.3; PEG, 10 | 3 | 200 | 4200 | 600 | 0.1 | 30 |
| 14. CuI/Ascorbic acid | CuI, 85.7 | Ascorbic acid, 14.3 | 0.7 | 200 | 4200 | 600 | 0.1 | 30 |
| 15. CuI/UV Stabilizer | CuI, 20 | UV Stabilizer, 80 | 2.5 | 10 mL + 190 mL IPA | 4000 | 600 | 0.1 | 1000 |
| 16. AgBr/PVP | AgBr, 10 | PVP-B, 90 | 10 | 100 | 4000 | 600 | 0.1 | 60 |

Table 24 shows the results of average particle size. Tables 25 and 26 show antimicrobial activity of select samples against *P. aeruginosa* and *S. aureus* respectively. Some of these formulations were made to verify the viability of grinding different materials with different functionalizing agents and to see if these will result in particle sizes with good antimicrobial activity. Under the specific processing conditions utilized for that sample, sometimes a bimodal or a trimodal particle size distribution was seen (measured by light scattering). In those cases where most of the mass was represented by a single fraction, other fractions are not shown. Unless stated otherwise, the antimicrobial properties were typically measured at 59 ppm of metal concentration (concentration in the testing solution). The concentrations of the functionalization agents in the testing solutions are also shown in Tables 25 and 26.

By varying the conditions of grinding and the formulation composition it was possible to vary the average particle size from about 3 to about 1,000 nm. It was also possible to obtain larger particle sizes, but attention was focused on obtaining particles smaller than about 200 nm. In general long grinding times and small, concentration of the material being ground favored the formation of smaller particles (e.g., see sample#3). It was also found, however, that it was possible to achieve attractive antimicrobial properties with modest grinding times (e.g., see samples 2, 4 and 11 to 14). It is also possible to introduce large fractions of CuI (greater than 10%) relative to the functionalizing agents, e.g., in samples 6, 13 and 14 the amount exceeds 80%. This stands in contrast to most chemical syntheses of CuI (see Examples 7 to 9) where the percentage of CuI to the surface functionalizing agent does not exceed 5% and is typically notably smaller than 5%

When such high concentration of functionalizing materials are used as in the chemical synthesis route, then the addition of the functionalized antimicrobial material to a matrix material involves the introduction of a large amount of functionalizing material, This can often impact negatively the properties of the end-products produced, particularly for solid products.

It has also been demonstrated that it is possible to grind and functionalize other metal salts including metal halides, and metal oxides, e.g. CuSCN, AuI, AgI, ZnO and AgBr samples 7, 8, 9, 10 and 16 respectively. Sample 15 shows preparation of CuI functionalized with a UV stabilizer.

TABLE 24

Particle Size

| Sample | Solids Proportion by Weight % | | Particle Size* by Mass % |
|---|---|---|---|
| | Metal Compound, % | Functionalization agent(s), % | |
| 1. CuI/PEG | CuI, 15 | PEG, 85 | 95% is 10 nm |
| 2. CuI/PEG/SDS | CuI, 20 | PEG, 77.61; SDS, 2.39 | 83% is 26 nm, 17% is 140 nm |
| 3. CuI/PVP | CuI, 0.47 | PVP-B, 99.53 | 93% is 3 nm, 5% is 17 nm |
| 4. CuI/PVP | CuI, 10 | PVP-B, 90 | 65% is 10 nm, 35% is 120 nm |
| 5. CuI/PVP/SDS | CuI, 20 | PVP-A, 77.61; SDS, 2.39 | 89% is 6 nm, 11% is 117 nm |
| 6. CuI/SDS | CuI, 85.7 | SDS, 14.3 | 75% is 20 nm, 25% is 120 |
| 7. CuSCN | CuSCN, 10 | PVP-A, 90 | 75% is 180 nm, 25% is 50 nm |
| 8. AuI | AuI, 0.21 | PVP-A, 99.79 | 99% is 4 nm |
| 9. AgI | AgI, 10 | PVP-A, 90 | 99% is 3 nm |
| 10. ZnO | ZnO, 10 | PVP-B, 90 | 93% is 120 nm |
| 11. CuI/CH (Chitosan) | CuI, 50 | Chitosan, 50 | 22% is 14 nm, 78% is 1371 nm |
| 12. CuI/CH/PVP | CuI, 10 | Chitosan, 10; PVP-B, 80 | 81% is 9 nm, 19% is 808 nm |
| 13. CuI/PEG/Bioterge | CuI, 85.7 | Bioterge, 4.3; PEG, 10 | 82% is 30 nm, 18% is 150 |
| 14. CuI/Ascorbic acid | CuI, 85.7 | Ascorbic acid, 14.3 | N/A |
| 15. CuI/UV Stabilizer | CuI, 85.7 | UV Stabilizer, 14.3 | 100% is 410 nm |
| 16. AgBr/PVP | AgBr, 10 | PVP-B, 90 | 96% 744 nm, 4% 165 nm |

Some of the dry powders (after grinding was over and the particles were dried in a roto-evaporator) were examined under an optical microscope. The particles of the dried cluster were found to be in the range of 570 nm to 2 microns for sample 6 and for sample 13 it was in the range of about 1 to 2 microns. This shows clusters of particles are formed upon drying, particularly when a polymeric agent (PEG in this case) is present.

TABLE 25 antimicrobial test results against *P. aeruginosa*

| Sample | Metal, (ppm) | Functionalization agent(s) (ppm) | $Log_{10}$ reduction of *P. aeruginosa* after given time | | | | | |
|---|---|---|---|---|---|---|---|---|
| | | | 5 min | 15 min | 30 min | 1 hr | 3 hr | 6 hr |
| 1. CuI/PEG | | | Not tested | | | | | |
| 2. CuI/PEG/SDS | Cu, (59.07) | PEG, (688); SDS (21) | | | >4.77 ± 0.00 | | >4.77 ± 0.00 | |
| 3. CuI/PVP | Cu, (59.07) | PVP-B, (37527) | | 4.33 ± 0.34 | | 4.57 ± 0.00 | >4.42 ± 0.21 | >4.57 ± 0.00 |
| 4. CuI/PVP | Cu, (59.07) | PVP-B, (1595) | | >4.64 ± 0.00 | | >4.64 ± 0.00 | >4.64 ± 0.00 | |
| 5. CuI/PVP/SDS | Cu, (59.07) | PVP-A, (688); SDS (1) | | | 4.59 ± 0.00 | | >4.60 ± 0.00 | |
| 6. CuI/SDS | Cu, (59.07) | SDS, (30) | | 3.60 ± 0.21 | | 3.97 ± 0.30 | >4.66 ± 0.00 | >4.66 ± 0.00 |
| 7. CuSCN | Cu, (59.07) | PVP-A, (1015) | | 0.51 ± 0.04 | | 3.95 ± 0.21 | 4.88 ± 0.00 | |
| 8. AuI | Au, (59.07) | PVP-A, 46034 | | | >5.07 ± 0.00 | | >5.07 ± 0.00 | |
| 9. AgI | Ag, (10) | PVP-A, (196) | | 0.10 ± 0.09 | | −0.07 ± 0.15 | 0.19 ± 0.21 | |
| | Ag, (59.07) | PVP-A, (1159) | | | | | | |
| | Ag, (200) | PVP-A, (3924) | | | | | | |
| 10. ZnO | | | Not tested | | | | | |
| 11. CuI/CH (Chitosan) | Cu, (59.07) | Chitosan, (177) | 1.36 ± 0.11 | >4.60 ± 0.00 | | >4.60 ± 0.00 | | |
| 12. CuI/CH/PVP | Cu, (59.07) | Chitosan, (177); PVP-B, (1418) | 1.63 ± 0.04 | >4.60 ± 0.00 | | >4.60 ± 0.00 | | |
| 13. CuI/PEG/Bioterge | Cu, (59.07) | Bioterge, (9); PEG, (21) | | | | | | |
| 14. CuI/Ascorbic acid | Cu, 59.07 | Ascorbic acid, (30) | | | | | | |

TABLE 26 antimicrobial test results against *S. aureus*

| Sample | Metal, (ppm) | Functionalization agent(s) (ppm) | $\log_{10}$ reduction of *S. aureus* after given time | | | | | |
|---|---|---|---|---|---|---|---|---|
| | | | 5 min | 15 min | 30 min | 1 hr | 3 hr | 6 hr |
| 1. CuI/PEG | | | Not Tested | | | | | |
| 2. CuI/PEG/SDS | Cu, (59.07) | PEG, (688); SDS (21) | | | 3.97 ± 0.00 | | >4.27 ± 0.00 | |
| 3. CuI/PVP | Cu, (59.07) | PVP-B, (37527) | | | | | | |
| 4. CuI/PVP | Cu, (59.07) | PVP-B, (1595) | | 2.36 ± 0.06 | | >4.38 ± 0.00 | >4.38 ± 0.00 | |
| 5. CuI/PVP/SDS | Cu, (59.07) | PVP-A, (688); SDS (21) | | | | | | |
| 6. CuI/SDS | Cu, (59.07) | SDS, (30) | | 1.53 ± 0.08 | | 3.57 ± 0.04 | >4.50 ± 0.00 | >4.50 ± 0.00 |
| 7. CuSCN | Cu, (59.07) | PVP-A, (1015) | | 0.27 ± 0.06 | | 0.56 ± 0.01 | 2.83 ± 0.07 | |
| 8. AuI | Au, (59.07) | PVP-A, (46034) | | 0 | | | | |
| 9. AgI | Ag, (10) | PVP-A, (196) | | 0.08 ± 0.05 | | 0.01 ± 0.00 | 0.14 ± 0.00 | |
| | Ag, (59.07) | PVP-A, (1159) | | | 0.59 ± 0.02 | | 3.94 ± 0.10 | |
| | Ag, (200) | PVP-A, (3924) | | | >4.71 ± 0.00 | | >4.71 ± 0.00 | |
| 10. ZnO | | | Not tested | | | | | |
| 11. CuI/CH (Chitosan) | Cu, (59.07) | Chitosan, (177) | | | | | | |
| 12. CuI/CH/PVP | Cu, (59.07) | Chitosan, (177); PVP-B, 1418 | | | | | | |
| 13. CuI/PEG/Bioterge | Cu, (59.07) | Bioterge, (9); PEG, (21) | 0.019 ± 0.06 | 1.68 ± 0.07 | | >4.53 ± 0.00 | | |
| 14. CuI/Ascorbic acid | Cu, (59.07) | Ascorbic acid, (30) | >4.60 ± 0.00 | >4.60 ± 0.00 | | >4.60 ± 0.00 | | |

The antimicrobial properties of the samples in Tables 23 and 24 are shown in Tables 25 and 26. Table 25 shows the antimicrobial properties when tested against *P. aeruginosa* and Table 26 shows the antimicrobial properties against *S. aureus*. Some materials were tested for both microbes and several were only tested for one of them. Good antimicrobial properties were obtained with the AuI suspensions. However, such suspensions were black in color and for those objects where color is an issue; this material will not meet the product requirements. The tests for AgI were carried out at 10, 59 and 200 ppm Ag and for CuI at 59 ppm Cu. These results on *S. aureus* in Table 26 show that AgI was quite ineffective at 10 and 59 ppm Ag, whereas it showed good antimicrobial property at 200 ppm. This shows that copper iodide is a more effective antimicrobial material as compared to silver iodide at lower concentrations (see several results on CuI at 59 ppm) in this table and also results presented previously (e.g., Tables 5 and 6).

It was also found that CuI exhibited greater antimicrobial effectiveness at short times (e.g., 15 minutes) than CuSCN (compare sample 3 vs sample 7 in Table 25), although CuSCN exhibited attractive antimicrobial properties at longer times. Chitosan is not soluble in water, but it is soluble in water when a small amount of acetic acid was added, and hence could be used as a functionalization agent in aqueous media. Chitson functionalized CuI (sample 11) exhibited high antimicrobial effectiveness in times as short as 15 minutes. CuI functionalized with ascorbic acid exhibited outstanding antimicrobial effectiveness in times as short as after 5 minutes (see sample 14 in Table 26). In several cases more than one functionalization agent was used, e.g., samples 2, 5, 12 and 13. All of these produced attractive antimicrobial effectiveness.

Although the copper concentration (as copper salt) in most formulations was 59 ppm, changes in the copper concentration would lead to changes in antimicrobial effectiveness. For example, increasing the copper concentration would produce increased antimicrobial effectiveness at a given time and comparable antimicrobial effectiveness at shorter times.

Example 32: Antimicrobial Activity Against *Trichophyton mentagrophytes* Fungus

*T. mentagrophytes* is a common nail fungus. To test the efficacy of the AM material, CuI nanoparticles functionalized with PVP were made following Example 24. The proportions of the materials used were different. 300 ml of acetonitrile, 60 g of PVP along with 0.2856 of CuI was used. The particle size of the functionalized particles was 6 nm. The $\log_{10}$ reduction in the fungus using a liquid suspension with Cu concentration at 59 ppm (as CuI) was evaluated at 6, 24 and 48, hr and was found to be 1.02, 2.93 and 2.99, respectively, which shows a high degree of effectiveness.

Example 33: Wound Dressing Preparation and Antimicrobial Testing (a) Solution for Preparation of Wound Dressings without Antimicrobial Material A solution was made with (a) 1.62 g sodium carboxymethyl cellulose (molecular weight (Mw) 700,000 obtained from Sigma Aldrich, Cat#419338) and (b) 80 g DI-H2O. This solution was stirred while heating at 70° C. to give a clear, viscous, colorless solution.

(b) Solution for Preparation of Wound Dressings with Functionalized CuI Particles (Resulted in 1 wt % Cu (as CuI) in Dry Solid)

A solution was made with (a) 0.0590 g CuI/PEG/Bioterge Powder (28.57% Cu (as CuI) in powder), prepared as Sample 13 in Example 31 except that the grinding time was 13 minutes instead of 30 minutes (the average CuI particle size was about 320 nm with polydispersity being 168%), (b) 80 g DI-H2O. This solution was stirred at room temperature and sonicated to give an opaque, white solution. At the end of this process, 1.62 g sodium carboxymethyl cellulose (molecular weight (Mw) 700,000). This solution was stirred while heating at 70° C. to give an opaque, viscous, slightly green solution.

(c) Preparation of Wound Dressing

One ply, white Kimtech Pure CL5 #06179, 50% rayon/ 50% polyester cleanroom wipes from Kimberly Clark Professional (Roswell, Ga.) were cut into 2"×2" pieces to use as gauze pieces for coating the above solutions for testing of wound dressings. The 2"×2" gauze pieces were first weighed before coating. They were then placed on a piece of glass and were pre-wetted by hand with 0.9 ml DI-H2O using a syringe. Solutions used for the wound dressing application were prepared as given below and 1 ml volume of one of these solutions was then evenly applied to the pre-wetted wipe by hand using a syringe.

The coated gauze pieces were then dried in the oven for 30-40 minutes at 70° C. Once dried the gauze pieces were removed from the glass and were weighed again to determine the total solids content. Applying 1 ml of the coating solutions to the gauze gave an average solid content of 0.02 g. Wipes were also prepared with solids content higher than 0.02 g, including single and multiple coating applications. After coating, the standard gauze pieces (no antimicrobial) were white in color and the copper containing gauze pieces were a pale green color. These coated gauze pieces were then tested against *P. aeruginosa* as follows.

(d) Testing of Dressings Against *P. aeruginosa*

A single colony of *P. aeruginosa* was cultured overnight to stationary phase in tryptic soy broth (TSB). The following day, the culture was diluted in TSB to read 0.1 optical density in a Synergy 2 reader (from Biotek Instruments Inc, Winooski, Vt.). Following this, 0.25 ml of culture was plated onto petri dishes containing tryptic soy agar (TSA). Gauze samples were then placed onto individual plates, one sample per plate. The total solid content on each gauze piece averages 0.02 g, with the copper content (in the form of CuI) being 1% of this mass. Each section was pressed firmly onto the agar on the plate to ensure homogeneous surface contact. The bacteria in contact with the gauze were allowed to grow for 72, and 96 hours, one plate per time-point. After each time-point the respective gauze sample was removed and the newly exposed area was swabbed with a sterile loop, which in turn was spread over a clean agar plate. This was allowed to grow for 24 hrs, after which visual inspection of the plate produces the following observations: 72 hrs Cu-gauze completely killed the bacteria originally plated under it, while the standard gauze displayed a heavy bacterial growth. The 96 hour gauze assay produced results identical to the 72 hr testing.

Example 34: Comparison of PU Coatings Made by Grinding CuI in Emulsion, Vs, Grinding CuI with SDS and then Adding these to the Emulsion In this preparation, CuI was ground with SDS (see Example 28). The composition after grinding was dried and then added to the polyurethane emulsion described in Example 24. In this example the CuI was not ground with the emulsion, but particles functionalized (pre-functionalized) with the surfactant were added and mechanically mixed into the PU emulsion. These were then coated on 5 cm×5 cm stainless steel coupons and evaluated for antimicrobial efficacy with and without CuI additive. The samples with CuI had a copper concentration of 1% in the dry coating. The results in Table 33 show that these samples were antimicrobial. These samples can be compared to coatings prepared by grinding CuI in PU emulsion, where this data is shown in Table 34. Samples produced by both methods exhibited very attractive antimicrobial properties.

TABLE 27

Pre-functionalized CuI particles added to PU coating emulsion

| Time | $Log_{10}$ Reduction *P. aeurginosa* | | $Log_{10}$ Reduction *S. aureus* | |
|---|---|---|---|---|
| | With CuI | Without CuI | With CuI | Without CuI |
| 24 hr | 4.05 | −0.49 | >4.47 | 0.21 |

TABLE 28

Functionalized particles formed by grinding CuI in PU coating emulsion

| Time | $Log_{10}$ Reduction *P. aeurginosa* | | $Log_{10}$ Reduction *S. aureus* | |
|---|---|---|---|---|
| | With CuI | Without CuI | With CuI | Without CuI |
| 24 hr | >5.04 | −0.49 | >5.15 | 0.15 |

Example 35: Nail Polish with Antimicrobial Additive and Testing

In order to demonstrate the incorporation of antimicrobial particles in to a nail polish, a commercial water based nail polish was evaluated. A water-based nail polish WaterColors Clear water-based nail enamel, was obtained from Honeybee Gardens Inc. (Leesport, Pa. The ingredients from the labels of these products were listed in Table 29.

TABLE 29

| Ingredients |
|---|
| Water, water-miscible acrylic, polyurethane formers and thickeners, non-ionic soaps. May contain: ultramarine blue, carmine, mica, iron oxides, and/or titanium dioxide |

The weight percent solids of the nail polish was determined by allowing a measured amount to dry in air for greater than 24 hours at ambient temperature and determining the weight loss upon drying.

The particles used were prepared by the grinding method with a composition of 85.7% CuI and 14.3% Bioterge PAS-8S. The grinding conditions are shown in Table 30. The average particle size was 320 nm. Dry copper iodide based antimicrobial powders were incorporated in the nail polishes at 1 wt % Cu (3 wt % CuI) by mechanical mixing.

TABLE 30

| Solids Proportion by Weight % | | Total Solids (g) | Water (mL) | Mill (RPM) | Pump (RPM) | Media Size (mm) | Grinding Time (min) |
|---|---|---|---|---|---|---|---|
| Metal Compound, % | Functionalization agent(s), % | | | | | | |
| CuI, 85.7 | Bioterge, 14.3 | 3 | 200 | 4200 | 600 | 0.1 | 30 |

Nail polish with the antimicrobial additive were coated on 2-inch square, stainless steel substrates and allowed to dry for greater than 24 hours. Nail polishes without the antimicrobial additive were coated in the same fashion to serve as standards. All of these coatings were evaluated for antimicrobial activity in the manner discussed earlier for other coatings. Over 24 hour period the control sample showed a $\log_{10}$ reduction of −1.16 (which shows growth), while the reduction in samples with the antimicrobial additive was 5.89. This shows a strong antimicrobial activity in samples with functionalized CuI particles.

Example 36: Preparation of Antimicrobial CuI Infused in Porous Silica and Treated with Surfactant Copper iodide (7.89 g) was added to a 1 L pear shaped flask along with a stir bar and acetonitrile (400 ml). This solution was then left to stir at room temperature for several hours. The resulting solution was clear and pale yellow in color.

The clear, pale yellow solution was then mixed with 25 g of Zeothix™ 265, a 3 µm silica (obtained from Huber). This solution was left to stir for one hour at room temperature to give a viscous, milky white/off-white solution. This solution was then dried on the rotary evaporator at room temperature, 30° C. and 60° C. to give a pink powder.

The resulting pink powder was then dispersed in 300 ml of deionized water along with 0.3945 g Stepanol™ WA-100 (sodium lauryl sulfate obtained from Stepan). The solution was stirred at room temperature for two hours and was a milky, pale yellow color. The solution was then dried overnight in the oven at 85° C. to give a pale green/orange/brown solid. When well mixed the solid was tan in color. This powder can now be used as an additive to polymeric and liquid antimicrobial formulations.

Example 37: Copper (I) Iodide Particle Dispersion Formation and Stabilization Using Water Soluble and Insoluble Polymers To a 250 ml round bottom flask fitted with a stir bar and stopper was added 0.123 g of copper iodide, 50 ml of anhydrous acetonitrile and 1.0 ml of poly(dimethylsiloxane). The poly(dimethylsiloxane) had a formula weight of 162.38, boiling point of 101° C./760 mmHg and a viscosity of 0.65 cST. The mixture was stirred at room temperature for 2 hours to give a pale green/blue solution. To this solution was added 2.578 g of polyvinylpyrrolidone with an average molecular weight of 10,000. Upon stirring this resulted in a green solution. The volatiles were removed slowly under reduced pressure (87 mmHg) at 25° C. and after approximately 4 hours a viscous slurry was obtained. The vacuum was increased to 5 mmHg and the bath temperature increased to 30° C. and after 30 minutes a fine dry green powder was obtained. It appeared that any excess poly(dimethylsiloxane) which was not attached to the surface of the particles was removed during the drying process. This powder was dispersed in 25 ml of de-ionized water by stirring to give an opaque white dispersion. This dispersion without agitation was stable for over 24 hours at room temperature. Dynamic light scattering analysis on a diluted sample of the dispersion gave an average particle radius of 160 nm.

Example 38: Formation of Fluorosurfactant Functionalized Copper Iodide Particles and their Use in Coatings 200 mL deionized water with 1.5 g 3M Novec FC 4430 (perfluorobutane sulfonate based surfactant from 3M as surface functionalizer) and 8.5 g copper iodide were processed in a ceramic ball mill (see Example 15) using 100 micron yttria stabilized zirconia grinding media at a mill speed of 4200 RPM and recirculation pump speed of 600 RPM for 180 minutes to form an opalescent milky green dispersion. This aqueous dispersion was concentrated by removing water under reduced pressure. To disperse the particles in an organic solvent, a small amount was dried to a green and grey, tacky solid. This material disperses well in methyl ethyl ketone (MEK). This material also redisperses well in water. Dynamic light scattering showed that the average particle size in water was 150 nm and in MEK it was 100 nm. This material can be used as an antimicrobial additive both in coating and other products formulated in water based systems and solvent based systems which are compatible with MEK.

To test its use in coatings, this material was added to a water based polyurethane coating formulation PU-73 (aliphatic urethane aqueous dispersion (35% solids) sold under the Tradename of ESACOTE™ obtained from Lambeth SpA, (Gallarate, Italy)). 50.0 g of this urethane dispersion was mixed with 1.0 g PZ-28 crosslinking agent (polyfunctional aziridine manufactured by PolyAziridine, LLC Medford, N.J.). This was coated on an aminosilane primed substrate by dip coating and cured for 2 hours at 70° C. to form a clear antimicrobial coating. The amount of copper was 0.25% (as copper iodide, similar to Example 25). In a similar fashion an acrylic antimicrobial coating was made from an MEK based system with copper content (as copper iodide) of 0.25% cured by UV. These coatings were clear.

Example 39: Formation of Antimicrobial Solvent Based Coatings with CuI Functionalized by Aminosilane Surface functionalized CuI additive was made forming a solution of 0.560 g 3-Aminopropyltriethoxysilane (APTES), 20 mL acetonitrile, 0.560 g CuI. This was stirred at room temperature and formed a brown solution. Acetonitrile was partially removed under reduced pressure to form a dispersion of CuI particles in a concentration of 12.5% by weight which were functionalized by APTES. The weight fraction of APTES in this formulation was also 12.5 wt %. This additive was soluble in methyl ethyl ketone (MEK) for use as an additive in coatings.

Example 40: Formation of Citric Acid Functionalized Copper Iodide Particles and formation of an antimicrobial solution 200 mL deionized water was mixed with 1.5 g citric acid (surface functionalizing agent) and 8.5 g copper iodide. This was processed by grinding in a ceramic ball mill using 100 micron yttria stabilized zirconia as in Example 28 for a period of 180 minutes to form a milky white dispersion. This was diluted in water to result in an antimicrobial solution. Solutions were produced with copper concentration ranging from 0.97% by weight down to 10 ppm by weight.

Example 41: Preparation of an Antimicrobial Cleaning (Disinfectant) Solution 1.36 g sodium lauryl surfate (functionalizing agent), 25.7 g CuI, and 257 mL deionized water were combined and processed in a ceramic ball mill as described in Example 28, with a pump speed of 100 RPM for 1300 minutes to form a milky white dispersion of surface functionalized CuI at 6.550 wt % solids.

This was combined with 5% aqueous solution of citric acid to form a 60 ppm Cu dispersion at pH of 2 to form an antimicrobial solution which may be applied by putting them in wipes or applied on surfaces, e.g., by spraying. Dynamic light scattering showed that the average particle size was 100 nm after aging for one week.

Another cleaning solution was formed by taking the above and adding a vinyl acetate-PVP copolymer (VA64 from BASF)) to a final concentration 3400 ppm. This polymer would leave a film on the surface (film former) after the solution is wiped and or dried with trapped antimicrobial particles so that the surface will continue to be microbe resistant long after the cleaning/application of this material. These cleaning solutions may also be formed by adding porous particles with antimicrobial additives loaded in the pores (see Example 36)

Example 42: Mill with Water-Acetonitrile Mixture 4.25 g CuI, 0.75 g sodium lauryl sulfate (surface functionalizer) was combined with 30 g acetonitrile, 170 g deionized water, This mixture was processed in a ceramic ball mill using 100 micron yttria stabilized zirconia grinding media at a mill speed of 4200 RPM and recirculation pump speed of 600 RPM for 300 minutes to form a foamy, milky dispersion. Upon completion of the above process additional 200 mL of deionized water was added and milling continued for 30 minutes to form an opalescent, foamy, white dispersion. This dispersion (in liquid form or after drying) forms additive to liquid or solid formulations and products.

Example 43: Antimicrobial Solvent Based Nail Polish

A mixture of 42.5 g CuI and 7.5 g Novec FC 4430 (3M) in 200 ml deionized water was milled for 1000 minutes at 4200 rpm mill speed with a pump speed of 600 rpm using the 100 μm YZT media. Other milling details were as in Example 28. This dispersion, after milling was then dried on the rotary evaporator at 40° C. The resulting solid was green in color.

The solvent based nail polish used was Nina Ultra Pro Salon Formula Super Dry Topcoat #709290 (produced by Cosmetic Design Group, Culver city, CA). The nail polish was clear and colorless and was found to have a solids content of 25.93%.

The CuI/Novec FC 4430 additive (0.0018 g) was mixed with 0.5 ml acetonitrile and 0.25 ml isopropanol and was easily dissolved at room temperature with stirring. This solution was clear and colorless. The Nina Ultra Pro Salon Formula Super Dry Topcoat (2 g) was added to the CuI/Novec FC 4430 solution and was left to stir for 10 minutes to give a clear, colorless solution.

A 5 cm×5 cm aluminum substrate was coated with the Nina Ultra Pro Salon Formula Super Dry Topcoat containing the CuI/Novec FC 4430 additive from above. One coating was painted by hand and was left to dry at room temperature. The coating was clear and colorless. A coating of Nina Ultra Pro Salon Formula Super Dry Topcoat with no additive was also painted by hand onto a 5 cm×5 cm aluminum substrate and was left to dry at room temperature. This coating was also clear and colorless. Upon examination, the coating with the CuI/Novec FC 4430 additive was indistinguishable from the polish coating with no additive.

Example 44: Preparation of Masterbatch and their Incorporation on Thermoplastic Products 300 mL deionized water with 6.25 g sodium lauryl sulfate and 118.75 g copper iodide were processed in a ceramic ball mill (see example 15) using 100 micron yttria stabilized zirconia grinding media at a mill speed of 4200 RPM and recirculation pump speed of 600 RPM for 240 minutes to form a milky white dispersion. 13.97 g PEG (Carbowax 8000, Dow) was added to the slurry and processed for an additional 120 minutes. This dispersion was dried to form a pink powder by removing water under reduced pressure.

This material was incorporated into a thermoplastic polyester (crystalline polyethylene terephalate-fiber grade) masterbatch. Two masterbatches were made by incorporating 7 and 17.6% of the above blend in virgin PET. Incorporation of these masterbatches in a concentration of 5% in additional PET to make antimicrobial PET results in copper concentration of 0.1 and 0.25%, respectively.

Example 45: Formation of Block Copolymer Functionalized Copper Iodide Particles and their Use in Coatings 300 mL deionized water with 20 g DisperBYK-190 (solution of high molecular weight block copolymer with pigment affinic groups from BYK USA Inc, Wallingford, Conn.) and 80.0 g copper iodide were processed in a ceramic ball mill (see Example 15) using 100 micron yttria stabilized zirconia grinding media at a mill speed of 4200 RPM and recirculation pump speed of 600 RPM for 1000 minutes to form an opalescent milky green dispersion. This aqueous dispersion was concentrated by removing water under reduced pressure. Dynamic light scattering showed that the average particle size in water was 150 nm. This concentrated dispersion can be dispersed in water based coating formulation. When a dilute aqueous dispersion of this material was tested for antimicrobial properties (with copper concentration being 59 ppm), in 30 minutes, the $\log_{10}$ reduction for $P.$ Aeruginosa (ATCC 9027) was >4.93, and the $\log_{10}$ reduction for $S.$ aureus (ATCC 25923) was 3.42.

To test its use in coatings, this material was added to a water based polyurethane coating formulation PU-73 (aliphatic urethane aqueous dispersion (35% solids) sold under the Tradename of ESACOTE™ obtained from Lambeth SpA, (Gallarate, Italy)). 50.0 g of this urethane dispersion was mixed with 1.0 g PZ-28 crosslinking agent (polyfunctional aziridine manufactured by PolyAziridine, LLC Medford, N.J.). This was coated on an aminosilane primed substrate by dip coating and cured for 2 hours at 70° C. to form a clear antimicrobial coating. The amount of copper was 0.25% (as copper iodide, similar to Example 25).

Example 46: Formation of Polyamine Amide and Acidic Polyester Functionalized Copper Iodide Particles 200 mL ethanol with 0.5 g Anti-Terra-U (solution of a salt of unsaturated polyamine amides and low molecular weight acidic polyesters from BYK) and 10.0 g copper iodide were processed in a ceramic ball mill (see Example 15) using 100 micron yttria stabilized zirconia grinding media at a mill speed of 4200 RPM and recirculation pump speed of 600 RPM for 180 minutes to form an opalescent ethanol green dispersion. This dispersion was dried to form a pink powder by removing water under reduced pressure. This powder disperses well in various organic solvents including butyl acetate. When a dilute aqueous dispersion of this material was tested for antimicrobial properties (with copper concentration being 59 ppm), in 30 minutes, the $\log_{10}$ reduction for *P. Aeruginosa* (ATCC 9027) was >4.93

Example 47: Formation Acidic Polyester Functionalized Copper Iodide Particles 300 mL ethanol with 5.0 g BYK-W 985 (solution of acidic polyester from BYK) and 92.5 g copper iodide were processed in a ceramic ball mill (see Example 15) using 100 micron yttria stabilized zirconia grinding media at a mill speed of 4200 RPM and recirculation pump speed of 600 RPM for 1000 minutes to form an opalescent milky green dispersion. This aqueous dispersion was dried to form a pink powder by removing ethanol under reduced pressure.

Example 48: Formation of Alkylol Ammonium Salt Copolymer (Ionic Polymer) Functionalized Copper Iodide Particles and their Use in Coatings 200 mL ethanol with 1.85 g DisperBYK-180 (alkylol ammonium salt of a copolymer with acid groups from BYK) and 10.0 g copper iodide were processed in a ceramic ball mill (see example 15) using 100 micron yttria stabilized zirconia grinding media at a mill speed of 4200 RPM and recirculation pump speed of 600 RPM for 330 minutes to form an opalescent milky green dispersion. This ethanol dispersion is compatible with water based coatings and many solvent systems. When a dilute aqueous dispersion of this material was tested for antimicrobial properties (with copper concentration being 59 ppm), in 30 minutes, the $\log_{10}$ reduction for *P. Aeruginosa* (ATCC 9027) was >4.78.

To test its use in coatings, this dispersion was added to a water based polyurethane coating formulation PU-73. 50.0 g of this urethane dispersion was mixed with 1.0 g PZ-28 crosslinking agent. This was coated on an aminosilane primed substrate by dip coating and cured for 2 hours at 70° C. to form a clear antimicrobial coating. The amount of copper was 0.25% (as copper iodide, similar to Example 25). In a similar fashion an acrylic antimicrobial coating was made from an MEK based system with copper content (as copper iodide) of 0.25% cured by UV. These coatings were clear.

The acrylic coatings were tested for their antimicrobial properties by evaluating them against *S. aureus* (ATCC #25923) using JIS2801-2000 as described earlier. The acrylic coating without the antimicrobial additive showed a decrease in this strain of 0.10±0.11 and 1.05±0.92 $\log_{10}$ reductions in a period of 6 and 24 hr respectively, for the same time periods coatings with antimicrobial additive (0.25 wt % copper) resulted in reductions of 3.47±0.61 and >4.40±0.00.

Example 49: Formation of Copper-Silver-Iodide-Bromide Solid Solution for Wound Dressings (1 wt % Cu (as CuI) in Dry Solid)

30 mL acetonitrile, 0.066 g silver bromide, 0.933 g copper iodide, and 31.1 g PVP-10K were stirred to form a clear green solution. This solution was dried to form a white powder by removing acetonitrile under reduced pressure. This powder was dispersed in water. This aqueous dispersion was used to form a wound dressing as in Example 33c. This was tested as in Example 33d. A complete kill of bacteria was observed within 24 hours.

Example 50: Formation of Copper-Potassium-Iodide Solid Solution for Wound Dressings (1 wt % Cu (as CuI) in Dry Solid)

30 mL acetonitrile, 1.0 g potassium iodide, 1.0 g copper iodide, and 32.33 g Copolymer Vinyl acetate-Vinyl pyrrolidone (Luvitec VA64, BASF, Germany) were stirred to form a clear orange solution. This solution was applied to form a wound dressing. Upon drying, copolymer functionalized CuI particles were formed. This wound dressing was tested as in Example 33d. A complete kill of bacteria was observed within 24 hours. A potassium iodide wound dressing was similarly prepared and did not appear to kill bacteria following the same procedure.

Example 51: Formation of Acidic Polyester Modified Copper Iodide Silica Blend 400 mL deionized water, 15 g acidic polyester modified copper iodide (see Example 46), and 15 g 3μ silica (Zeothix 265) were processed in a ceramic ball mill (see Example 15) using 100 micron yttria stabilized zirconia grinding media at a mill speed of 4200 RPM and recirculation pump speed of 600 RPM for 180 minutes to form an opalescent milky dispersion. This dispersion was dried by removing water under reduced pressure to form a gray to pink solid.

Example 52: Formation of Antimicrobial Dental Adhesive with an Inorganic Copper Salt Kerr Optibond XTR dental adhesive (Kerr Corporation, Orange, Calif.) was combined with an inorganic copper salt. This copper salt was surface functionalized (copper iodide functionalized with bioterge, see Example 35). Ethanol (solvent) was added to the adhesive to reduce its viscosity in order to effectively mix the functionalized CuI particles. Ethanol was removed under reduced pressure to form a viscous CuI containing dental adhesive paste. This dental adhesive was coated on to aluminum substrates and cured under UV. The substrates were further cured at 130° C. under nitrogen at 60 psi for 20 minutes using a BelleGlass™ HP Curing Unit (Kerr Corporation, Orange, Calif.).

Dental adhesive coatings were formed at 0.5, 0.25, and 0.0% Cu by weight (as CuI). These coatings were evaluated against *streptococcus mutans* over a period of six hours using JIS2801-2000 procedure as described above. The $\log_{10}$ reductions of the microbes in these coatings were >3.93, >3.81 and 0.59 respectively.

Example 53: Improved Dispersibility of CuI by Addition of Soluble Iodide Salt To a round bottom flask was added 30 mL of anhydrous acetonitrile, 15 g of PVP 10K. This was stirred to form a clear solution. To this was added copper iodide or copper iodide along with sodium iodide. Clear solutions were formed in all cases. Both of these solutions was dried under reduced pressure and redispersed separately in water and linear alcohols methanol, ethanol, propanol, and butanol. These solutions were monitored for clarity (stability) for 1 month as described in the table below.

TABLE 31

| Sample ID | CuI (g) | Salt, NaI (g) | PVP 10K (g) | Redisperses in Water as a clear dispersion | Redisperses in Alcohol as a clear dispersion |
|---|---|---|---|---|---|
| A | 0.367 | 0.133 | 15 | Yes, Stable | Yes, Stable |
| B | 0.367 | 0.000 | 15 | No | No |

Example 54: Improved Dispersibility of a Salt with Low Water Solubility with Addition of a High Water Solubility Salt The use of sodium iodide (a water soluble salt) was evaluated to improve dispersability of functionalized copper iodide particles. A clear solution was made with 200 ml of deionized water and 0.399 g of NaI. To this solution 1.01 g of copper iodide was added. To this mixture 45 g of PVP 10K (PVP with a molecular weight of 10,000) was added and still CuI did not dissolve. 200 mL deionized water with 45 g PVP 10K, 1.101 g copper iodide, and an amount of sodium iodide or sodium chloride (see table below) were processed in a ceramic ball mill (see Example 15) using 100 micron yttria stabilized in zirconia grinding media at a mill speed of 4200 RPM and recirculation pump speed of 600 RPM for 1000 minutes. Sample was also made without any sodium iodide but with PVP (sample C). Particle size was measured of the as prepared dispersions by dynamic light scattering. Particle size was also measured for the dispersions after being dried under reduced pressure and redispersed in water by dynamic light scattering. Also to be noted that addition of soluble iodide salt (as sodium iodide) along with PVP helped in decreasing the particle size of CuI more efficiently, and further, such dispersions were highly stable.

In another experiment the benefits seen by adding soluble iodide were reevaluated by lowering its concentration relative to the CuI used. In addition, relative amount of PVP was also decreased. 200 mL deionized water with 1.0 g PVP 10K, 4.0 g copper iodide, and 0.1 g of sodium iodide were processed in a ceramic ball mill (see Example 15) using 100 micron yttria stabilized zirconia grinding media at a mill speed of 4200 RPM and recirculation pump speed of 600 RPM for 250 minutes. Particle size was measured of the as prepared dispersion by dynamic light scattering to be 10-80 nm. Particle size was also measured for the dispersion after being dried under reduced pressure and redispersed in water by dynamic light scattering to be 10-80 nm. Both the as prepared and dried and redispersed dispersions exhibit a much stronger resistance to settling than similar preparations without the addition of sodium iodide.

Example 55: Efficacy in CuI Containing Wound Dressings by Addition of Acids and Salts In this example the CuI/PVP samples were made using PVP with a molecular weight of 10,000 and along with sodium iodide and was prepared as detailed in Example 53, Sample A.
  a) To a round bottom flask was added 0.2 g Citric Acid (Citric acid >99%, Aldrich C0759), 1 g of prepared CuI/PVP 10 k powder (2.38 wt % CuI) and 5 mL DI-water.
  b) a) To a round bottom flask was added 0.2 g Citric Acid (Citric acid >99%, Aldrich C0759), 1 g of PVP 10K powder and 5 mL DI-water.
  c) To a round bottom flask was added 0.2 g Ascorbic Acid (L-Ascorbic acid >99%, Aldrich 95210), 1 g of prepared CuI/PVP 10K powder (2.38 wt % CuI) and 5 mL DI-water.
  d) a) To a round bottom flask was added 0.2 g Ascorbic Acid (L-Ascorbic acid >99%, Aldrich 95210), 1 g of PVP 10K powder and 5 mL DI-water.
  e) To a round bottom flask was added 0.2 g Citric Acid (Citric acid >99%, Aldrich C0759), 0.1 g Sodium Bicarbonate, and 5 mL DI-water. This was allowed to react to form a citrate salt and form a clear solution with a pH of 4. Then 1 g of prepared CuI/PVP 10 k powder (2.38 wt % CuI) was added.
  f) To a round bottom flask was added 0.2 g Ascorbic Acid (L-Ascorbic acid >99%, Aldrich 95210), 0.1 g Sodium Bicarbonate, and 5 mL DI-water. This was allowed to react to form a citrate salt and form a clear solution with

TABLE 32

| Sample ID | CuI (g) | Salt, (g) | PVP K17 (g) | Water | Average particle Size (as prepared) | Average particle Size (dried and redispersed) | Remarks |
|---|---|---|---|---|---|---|---|
| A | 1.101 | NaI, 0.399 | 45 | 200 mL | 5 nm | 5 nm | Clear green dispersion |
| B | 1.101 | NaCl, 0.399 | 45 | 200 mL | >1 micron | >1 micron | Hazy yellow dispersion, Large amount of sediment |
| C | 1.101 | None, 0.000 | 45 | 200 mL | >1 micron | >1 micron | Hazy yellow dispersion, Large amount of sediment | a pH of 4. Then 1 g of prepared CuI/PVP 10 k powder (2.38 wt % CuI) was added.

These aqueous dispersions were used to form wound dressing as in Example 33c. E. coli (ATCC#25922) was used instead of P. Aeruginosa to test the antimicrobial properties. These were tested by culturing a single colony of E. coli (ATCC #25922) overnight to stationary phase in tryptic soy broth (TSB). The following day, the culture was diluted in TSB to read optical density in a Synergy 2 reader (from Biotek Instruments Inc, Winooski, Vt.). Following this, 0.25 ml of culture was plated onto petri dishes containing tryptic soy agar (TSA). 10 mm circular pieces of gauze samples were then placed onto inoculated plates. Each piece of gauze was lightly pressed to ensure contact with the agar and then the plate was inverted and incubated at 37° C. for 16-24 hours. After this time period, a zone of inhibition (ZOI) was observed around the wound dressings which was optically clear (not hazy) showing that no bacteria grew in this zone. The size of this zone (zone of inhibition) was noted in mm from the perimeter of the wound dressings after 24 hours. The zone of inhibition around sample (a) was 5.0 mm, (b) 2.5 mm, (c) 3.0 mm, (d) 0.5 mm, (e) 5 mm, (f) 3 mm.

Example 56: Efficacy in CuI Containing Wound Dressings by Addition of Citrate Salt at Different Concentrations In this example the CuI/SLS powder used was 75/25 by weight and was produced by grinding as described in Example 28.

(a) To a round bottom flask was added 0.2 g Citric Acid (Citric acid >99%, Aldrich C0759), 0.0875 g Sodium Bicarbonate (Aldrich 56014) and 5 g DI-water. The mole ratio of citric acid to sodium bicarbonate was 1. This was allowed to react and form a clear solution with a pH of 3.5. To this solution was added 1 g of PVP 10K and 0.3 g of prepared CuI/SLS powder (25% Cu). The pH remained constant and a blue or green color developed.

(b) A sample was prepared as in example (a) with an increased amount of sodium bicarbonate. The amount of sodium bicarbonate used was 0.175 g. The mole ratio of citric acid to sodium bicarbonate was 2. The pH was 5.5. All other parameters remained as in example (a).

(c) A sample was prepared as in example (a) with an increased amount of sodium bicarbonate. The amount of sodium bicarbonate used was 0.263 g. The mole ratio of citric acid to sodium bicarbonate was 3. The pH was 7. All other parameters remained as in example (a).

(d) To a round bottom flask was added 0.2 g Citric Acid (Citric acid >99%, Aldrich C0759), 0.263 g Sodium Bicarbonate (Aldrich S6014) and 5 g DI-water. The mole ratio of citric acid to sodium bicarbonate was 3. This was allowed to react and form a clear solution with a pH of 7. To this solution was added 1.225 g of PVP 10K and 0.075 g of SLS powder.

These aqueous dispersions were used to form wound dressing and tested as in Example 55 and tested against E. coli (ATCC#25922). The zone of inhibition around sample (c) was larger than (a) and (b). The zone of inhibition around sample (b) was larger than (a). Sample (d) showed no zone of inhibition. After testing it was observed that sample (c) had a stronger blue color, followed by samples (b) and (a).

Example 57: Improved Dispersibility of CuI by Milling with Soluble Salts and Polymer, and Use of Metals a) Copper iodide, sodium iodide, polyvinvylpyrrolidone K17, and deionized water were combined as described in the table below. These materials were processed together in a ceramic ball mill (see Example 15) using 100 micron grinding media (3M™ Micro Milling Media ZGC) at a mill speed of 4200 RPM and recirculation pump speed of 600 RPM.

TABLE 33

| CuI (g) | PVP (g) | NaI (g) | DI-Water (mL) | Grinding Time (min) |
|---------|---------|---------|---------------|---------------------|
| 9       | 40      | 1       | 150           | 1000                |
| 9       | 2       | 1       | 200           | 350                 |
| 9       | 2       | 0.25    | 200           | 1200                |
| 9       | 0.9     | 0.1     | 200           | 450                 |
| 9       | 0.95    | 0.05    | 200           | 350                 |
| 18      | 1.95    | 0.05    | 200           | 1000                |
| 90      | 9       | 1       | 140           | 350                 |
| 90      | 9.5     | 0.5     | 200           | 1330                |

Each milled product appeared as a semi translucent opalescent dispersion that was stable against settling with particle sizes around 10-30 nm. The dispersions were dried to form purple colored solids under reduced pressure. Subsequent redispersal formed dispersions similar to as before drying with particle sizes around 10-30 nm.

b) 18 g Copper iodide, 0.05 g sodium iodide, 1.95 g copovidone VA64 (copolymer of polyvinvylpyrrolidone and vinyl acetate), and 200 mL deionized water were combined and processed together in a ceramic ball mill (see Example 15) using 100 micron grinding media (3M™ Micro Milling Media ZGC) at a mill speed of 4200 RPM and recirculation pump speed of 600 RPM for 350 minutes. This milled mixture appeared as a semi translucent opalescent dispersion. This dispersion was dried to a solid under reduced pressured and subsequently redispersed to form a similar dispersion as before drying with a particle size around 10-30 nm.

c) 9 g Copper iodide, polyvinvylpyrrolidone 0.9 g PVP K17, 0.1 g silver nitrate, and deionized water were combined and processed together in a ceramic ball mill (see Example 15) using 100 micron grinding media (3M™ Micro Milling Media ZGC) at a mill speed of 4200 RPM and recirculation pump speed of 600 RPM for 400 minutes. A translucent dispersion was formed after processing.

d) 9 g of copper iodide and 0.9 g PVP K17 were processed as in (c) using 0.1 g copper(I) acetate rather than silver nitrate. A translucent dispersion was formed after processing.

e) 9 g of copper iodide and 0.9 g PVP K17 were processed as in (c) using 0.1 g elemental silver (10 micron powder) rather than silver nitrate. A translucent dispersion was formed after processing.

f) 9 g of copper iodide and 0.9 g PVP K17 were processed as in (c) using 0.1 g elemental copper (10 micron powder) rather than silver nitrate. A translucent dispersion was formed after processing.

g) 9 g of copper iodide and 0.9 g PVP K17 were processed as in (c) using 0.1 g elemental zinc (10 micron powder) rather than silver nitrate. A translucent dispersion was formed after processing.

h) 9 g of copper iodide and 0.9 g PVP K17 were processed as in (c) using 0.1 g elemental iodine rather than silver nitrate. A translucent dispersion was formed after processing.

Example 58: Improved Dispersibility of AgI by Milling with Soluble Iodide and Polymer a) 9 g Silver iodide, 0.1 g potassium iodide, 0.9 g polyvinylpyrrolidone K17, and 200 mL deionized water were combined and processed together in a ceramic ball mill using 100 micron grinding media (3M™ Micro Milling Media ZGC) at a mill speed of 4200 RPM and recirculation pump speed of 600 RPM for 350 minutes.

This milled mixture appeared as a semi translucent green dispersion. This dispersion was dried to a solid under reduced pressured and subsequently redispersed to form a similar dispersion as before drying with a particle size around 10-30 nm.

Example 59: Wound Dressing Compositions a) To a round bottom flask was added 10 g trisodium citrate (Aldrich), 6.67 g of copper iodide powder as prepared in example 88 as 90% CuI, 9% PVP, and 1% NaI, 83.33 g PVP K17, and 300 mL deionized water. This aqueous dispersion had 25% solids and was used to form wound dressing by applying 1 g of liquid dropwise to a 2×2 inch cellulose polyester fabric and drying the fabric in an oven at 75° C. on a glass tray.

b) Similar wound dressings were prepared with 6.67 g of copper iodide powder as prepared in example 89 as 90% CuI, 9% PVP, and 1% NaI, 93.33 g PVP K17, and 300 mL deionized water.

c) Standard wound dressings were similarly prepared and consisted of 10% trisodium citrate and 90% PVP K17.

d) These wound dressings were tested by applying a 10 mm circular swatch to a bacterial *pseudomonas aeruginosa* (ATCC#9027) biofilm, such that the biofilm was completely covered by the wound dressing. The biofilm had been grown overnight on a 0.2 micron membrane on agar and transferred to fresh agar upon application of the wound dressing. Bacterial reductions were determined by removing the wound dressing, sonicating the membranes in PBS, and plating the PBS at 10× dilutions to count viable colony forming units.

e) In biofilm testing described above the samples containing both copper iodide and trisodium citrate (sample a) performed superior to samples without citrate and without both citrate and copper iodide (sample b and c).

Example 60: Preparation and Testing of Wound Dressings a) Preparation of Wound Dressings
i) Wound dressings were prepared by combining 0.0667 g copper iodide powder as described in Example 57a (90% CuI, 1% NaI, 9% PVPK17), 1.733 g PVP K17, 0.20 g trisodium citrate, and 6 mL deionized water. This dispersion was applied to a 4 sq in piece of gauze as in Example 55 at 0.25 g solids per 4 sq in. This was subsequently dried and further processed to form wound dressings as described in Example 55.
ii) 0.0667 g copper iodide powder as described in Example 57c (90% CuI, 1% AgNO$_3$, 9% PVPK17), 1.733 g PVP K17, 0.20 g trisodium citrate, and 6 mL deionized water were mixed to form wound dressings as in (i).
iii) 0.0667 g copper iodide powder as described in Example 57a (90% CuI, 1% NaI, 9% PVPK17), 1.333 g PVP K17, 0.20 g trisodium citrate, 0.40 g ascorbic acid, and 6 mL deionized water were mixed form wound dressings as in (i).
iv) 1.733 g PVP K17, 0.20 g trisodium citrate, and 6 mL deionized water mixed to form wound dressings as in (a).

b) Testing of Wound Dressings
Wound dressings (i-iv) were tested as described in Example 55 using *Pseudomonas aeruginosa* (ATCC#9027), *Staphylococcus aureus* (ATCC#25923, and *Escherichia coli* (ATCC#25922). Unless mentioned otherwise only these bacterial strains were used to test the wound dressings in other examples.

The zone of inhibition (ZOI) for (i) and (ii) were equivalent for all three microbes. The ZOI for (iii) was larger than both (i) and (ii) for all three microbes. There was no ZOI for (iv) for *Pseudomonas aeruginosa* and *Escherichia coli*, however, there was a ZOI smaller than (i) or (ii) against *Staphylococcus aureus*.

Example 61: Preparation and Testing of Wound Dressings a) Preparation of Copper Iodide Wound Dressing
0.133 g copper iodide powder as described in Example 57a (90% CuI, 1% NaI, 9% PVPK17), 1.266 g PVP K17, 0.20 g trisodium citrate, 0.40 g ascorbic acid, and 6 mL deionized water were mixed form wound dressings as in Example 33c. The loading of solids was at 0.50 g per 4 sq in.

b) Preparation of Control Wound Dressing
1.333 g PVP K17, 0.20 g trisodium citrate, 0.40 g ascorbic acid, and 6 mL deionized water mixed to form wound dressings as in Example 33c. The loading of solids was at 0.50 g per 4 sq in. This sample had no copper.

c) Testing of Wound Dressings
Copper iodide and Standard wound dressings were tested along with Aquacel Ag (silver containing commercial wound dressing) as described in Example 55 using *Pseudomonas aeruginosa* (ATCC#9027), *Staphylococcus aureus* (ATCC#25923), and *Escherichia coli* (ATCC#15597). Zone of inhibition results are described in the table below.

TABLE 34

| Plate # | Organism | Sample | ZOI (mm) |
|---|---|---|---|
| 1 | *Psudomonas aeruginosa* (ATCC# 9027) | Control | 0.0 |
|   |   | Aquacel Ag | 1.6 |
| 2 | *Psudomonas aeruginosa* (ATCC# 9027) | CuI | 1.6 |
|   |   | Aquacel Ag | 1.6 |
| 3 | *Staphylococcus aureus* (ATCC# 25923) | CuI | 1.6 |
|   |   | Aquacel Ag | 1.6 |
| 4 | *Escherichia coli* (ATCC# 15597) | CuI | 1.6 |
|   |   | Aquacel Ag | 1.6 |

Example 62: Wound Dressings Prepared with Alternative Polymers 0.133 g copper iodide powder as described in Example 57a (90% CuI, 1% NaI, 9% PVPK17), 1.266 g of polymer as described in the table below, 0.20 g trisodium citrate, 0.40 g ascorbic acid, and 6 mL deionized water were mixed form wound dressings as in (a) at 0.75 g per 4 sq inch. These wound dressings were tested against *Pseudomonas aeruginosa* (ATCC#9027) as described in Example 55. All samples had equivalent zones of inhibition as described in the table below.

TABLE 35

| Polymer | Zone of Inhibition (mm) |
|---|---|
| PVP K17 | 1.5 |
| PVP MW = 55,000 | 1.5 |
| VA64 Copolymer | 1.5 |

TABLE 35-continued

| Polymer | Zone of Inhibition (mm) |
|---|---|
| 80% PVP K17, 20% Carboxymethylcellulose | 1.5 |
| PEG MW = 8,000 | 1.5 |
| None | 1.5 |

Example 63: Wound Creams a) Antimicrobial wound creams were prepared by sodium carboxymethycellulose, trisodium citrate, and copper iodide powder as prepared in Example 57a as 90% CuI, 9% PVP, and 1% NaI. These creams were prepared at 6% sodium carboxymethycellulose, 10% trisodium citrate, and copper levels of 0.00%, 0.25%, 0.50%, 1.00%, and 5.00%.

b) These wound creams were tested using a zone of inhibition method. A 6 mm well was formed in the center of an inoculated agar plate and filled with the wound cream. Each cream was run in triplicate on three separate plates. Each plate was allowed to incubate overnight at 37° C. and then the zone of inhibition was measured. Each cream was tested against *Pseudomonas aeruginosa* ATCC#9027) and *Staphylococcus aureus* (ATCC#25923).

c) The zone of inhibition measured results of wound creams described in (a) along with commercial bacitracin ointment tested as in (b). These measurements are in cm for the diameter of the zone of inhibition including the well.

TABLE 36

| | 0.00% Cu | 0.25% Cu | 0.50% Cu | 1.00% Cu | 5.00% Cu | Bacitracin |
|---|---|---|---|---|---|---|
| P. aeruginosa | 1.0 ± 0.3 | 1.2 ± 0.2 | 1.1 ± 0.0 | 1.4 ± 0.2 | 2.1 ± 0.0 | 0.6 ± 0.1 |
| S. aureus | 1.5 ± 0.1 | 1.6 ± 0.1 | 1.8 ± 0.1 | 2.2 ± 0.2 | 4.4 ± 0.4 | 0.6 ± 0.1 |

Example 64: Functionalization of CuI with $SiO_2$

To a one liter flask was added 200 mL deionized water (18 mΩ-cm) with pH adjusted to 2.0 using dilute HCl and 10.0 g (0.05251 m) of cuprous iodide. The mixture was stirred using a high shear mixer (Ross LSK Mixer) at a maximum speed of 20,000 rpm. While mixing at 15,000 rpm 4.75 g (0.228 m) of tetraethylorthosilicate (Aldrich, 99%) was added dropwise. This resulted in a fine white dispersion. This mixture was processed in a ceramic ball mill (see example 15) using 100 micron grinding media (3M™ Micro Milling Media ZGC) at a mill speed of 4200 RPM and recirculation pump speed of 600 RPM for 1300 minutes. After 4 hours of milling the pH had increased to 4.0, after 6 hours of milling the pH had increased to 5.6, and after completion of milling (1300 min) the pH had increased to 6.3. The dispersion had developed an opaque white appearance with pink foam.

This dispersion was then removed from the mill and placed under high speed stirring at 3000 rpm; 0.2 mL of dilute ammonia (3 ml of 28% ammonia solution in 25 ml of deionized water) was added and allowed to mix for 1 hour. The pH initially went basic and then decreased to a steady value of 6.0. This dispersion was heated to reflux under magnetic stirring for 2 hours cooled to room temperature and left stirring overnight.

This dispersion was filtered on a 0.8 micron nylon filter (Osmonics) and washed with excess water and ethanol. The filtrate was clear and without color. The dry product was cured in a convection oven at 200° C. overnight to give an off white fine powder of composition 12 wt % $SiO_2$ and 88 wt % CuI. This powder was dispersed in water and its efficacy tested against *P. aeruginosa* (ATCC#9027) at a copper concentration of 60 ppm. Table 37 shows the results after 15 minutes compared to the PBS control. The starting bacterial titer concentration was $2.4 \times 10^6$ cfu/ml.

TABLE 37

| Time | PBS Control | CuI/SiO2 |
|---|---|---|
| 15 min | 0.07 ± 0.03 | 3.73 ± 0.07 |

The CuI/$SiO_2$ powder was added to Harmony White Paint (Sherwin Williams Interior Acrylic Latex semi gloss "green sure designation") at a copper concentration of 0.1 wt % stirred and stored for six days and the color coordinates (CIE 1931 color space) determined as shown below in the Table below.

TABLE 38

Liquid Paint color properties with and without CuI/$SiO_2$

| Sample | Storage time | CIE Color Coordinates | | |
|---|---|---|---|---|
| | | L* | a* | b* |
| Harmony White Paint Liquid | Initial | 88.43 | −0.93 | 2.60 |
| Harmony White Paint Liquid | Six days | 88.39 | −0.93 | 2.57 |
| Harmony Paint Liquid with 0.1 wt % Cu | Initial | 87.77 | −2.30 | 3.86 |
| Harmony Paint Liquid with 0.1 wt % Cu | Six days | 87.16 | −2.59 | 3.60 |

The paint with and without CuI/$SiO_2$ as described in the above table was applied to a 2"×2" aluminum substrate and cured at 85° C. The color coordinates were determined for the painted substrates initially and after storage at 85° C. for six days. The results are listed below in the table.

TABLE 39

Cured paint on aluminum substrate with and without CuI/$SiO_2$ added

| Sample | Storage time | CIE Color Coordinates | | |
|---|---|---|---|---|
| | | L* | a* | b* |
| Harmony White Paint Liquid | Initial | 93.98 | −0.84 | 1.80 |
| Harmony White Paint Liquid | Six days at 85° C. | 94.44 | −1.31 | 3.63 |

TABLE 39-continued

Cured paint on aluminum substrate with and without CuI/SiO₂ added

| Sample | Storage time | CIE Color Coordinates | | |
|---|---|---|---|---|
| | | L* | a* | b* |
| Harmony Paint Liquid with 0.1 wt % Cu | Initial | 93.31 | −2.96 | 4.61 |
| Harmony Paint Liquid with 0.1 wt % Cu | Six days at 85° C. | 92.01 | −2.81 | 7.03 |

Example 65: Silica Functionalized Copper Iodide a) 200 mL deionized water (18 mΩ-cm) with pH adjusted to 2.0 using Acetic Acid and 10.0 g (0.05251 m) of cuprous iodide were processed in a ceramic ball mill (see Example 15) using 100 micron grinding media (3M™ Micro Milling Media ZGC) at a mill speed of 4200 RPM and recirculation pump speed of 600 RPM for 350 minutes. 4.75 g (0.228 m) of tetraethylorthosilicate (Aldrich, 99%) was added and milling was continued for another 10 minutes.

This dispersion was then removed from the mill and placed under high speed stirring at 3000 rpm; 0.2 mL of dilute sodium hydroxide was added and allowed to mix for 1 hour. This dispersion was heated to reflux under magnetic stirring for 1 hour and then cooled to room temperature and left stirring overnight.

This dispersion was filtered on a 0.8 micron nylon filter (Osmonics) and washed with excess water and ethanol. The filtrate was clear and without color. The dry product was cured in a convection oven at 120° C. overnight to give an off white fine powder of composition 12 wt % $SiO_2$ and 88 wt % CuI.

b) Another formulation was processed where 10.0 g of Copper iodide and 4.75 g of tetraethylorthosilicate were milled as in (a) using ethanol rather than deionized water. This dispersion was dried under reduced pressure at room temperature to give a fine powder. All of the other steps were similar.

c) Copper iodide was processed as in (b), where ammonia was used rather than sodium hydroxide.

Example 66: Disinfectant with Acids

Disinfectant solutions D1, D3 and D5 were respectively prepared in deionized water with 5% of ascorbic acid, 5% nitric acid and 5% citric acid as shown in the table below. In addition three additional formulations D2, D4 and D6 were also prepared with these respective acids along with CuI particles functionalized with sodium lauryl sulfate (SLS) to yield a final copper concentration of 60 ppm in these formulations. These were prepared by stirring the components for one hour in sure seal bottles. All of the samples with CuI/SLS were slightly hazy.

TABLE 40

| Ingredient (g) | Formulations | | | | | | | |
|---|---|---|---|---|---|---|---|---|
| | D1 | D2 | D3 | D4 | D5 | D6 | D7 | D8 |
| Water | 50 | 50 | 50 | 50 | 47.5 | 50 | | |
| Ascorbic acid | 2.63 | 2.63 | | | | | | |
| Citric acid | | | 2.63 | 2.63 | | | | |
| Acetic acid | | | | | 2.5 | 2.5 | | |
| CuI/SLS | | 0.0126 | | 0.0126 | | 0.0126 | | |

Ascorbic acid (>99%, Fluka, United Kingdom)
Citric acid, 99% (Sigma-Aldrich Corp., St. Louis, MO)
Acetic acid, ≥99.7% (Sigma-Aldrich Corp., St. Louis, MO)
CuI/SLS (75/25% by weight prepared as in Example 62)

The pH of both of the acetic acid containing formulation was measured and found to be 2.383 for D5 and 2.346 for D6. This was done using an Orion 290A+pH meter equipped with an Orion Ross Sure-flow Glass Combination pH Electrode. The pH meter was calibrated with pH standards 4, 7 and 10 (all pH standards from ACROS Organics, Geel, Belgium) to give a slope of 98.5.

All of the solutions above were analyzed for their antimicrobial properties by testing them against *Staph aureus*. A hard surface tile (10.8×10.8 cm) was inoculated with $10^9$ CFU *Staph aureus* and spread over the surface. After drying this tile was sprayed with the test solution to cover the tile completely (~2 ml) and was swabbed after a period of two minutes, and the swab was dropped in a DE neutralizing solution diluted 100 times with PBS buffer to ensure that the acidity of the spray solution did not change the pH of the neutralizing solution. These solutions were then cultured on agar plates as described earlier. The results are seen in the Table below.

TABLE 41

Testing Results against *S. aureus* (2 minutes of contact time)
Testing against *S. aureus* ATCC 25923

| PBS Control $Log_{10}$ Reduction | 5% ascorbic acid solution (D1) $Log_{10}$ Reduction | 5% ascorbic acid + CuI/SLS (D2) $Log_{10}$ Reduction | 5% citric acid solution (D3) $Log_{10}$ Reduction | 5% citric acid + CuI/SLS (D4) $Log_{10}$ Reduction | 5% acetic acid solution (D5)* $Log_{10}$ Reduction | 5% acetic acid + CuI/SLS (D6)* $Log_{10}$ Reduction |
|---|---|---|---|---|---|---|
| 0.08 ± 0.07 | 0.65 ± 0.11 | 1.05 ± 0.14 | 0.65 ± 0.08 | 1.78 ± 0.19 | 0.91 ± 0.13 | 1.68 ± 0.14 |

Original titer = 6.80E+07 cfu/mL
*These tests were done separately, the PBS standards for this series read −0.24 ± 0.12

Example 67: Disinfectant with Chitosan

A water based disinfectant solution was prepared with 8% of acetic acid, 60 ppm Cu, 3% Isopropanol and 3400 ppm Chitosan as follows:

In a sure seal bottle equipped with a stir bar, 0.0131 g of copper (I) iodide (75%)/sodium lauryl sulfate (25%) powder, prepared in Example 28, was mixed with 0.186 g chitosan (Sigma-Aldrich Corp., St. Louis, Mo.), 1.65 g isopropanol, 99.5% (Sigma-Aldrich Corp., St. Louis, Mo.) and 48.35 g deionized water. Lastly, 4.4 g acetic acid, ≥99.7% (Sigma-Aldrich Corp., St. Louis, Mo.) was added. This solution was stirred at room temperature for one hour to give a translucent, slightly hazy, colorless solution. The pH of this solution was found to be 2.534 using an Orion 290A+pH meter equipped with an Orion Ross Sure-flow Glass Combination pH Electrode. The pH meter was calibrated with pH standards 4, 7 and 10 (all pH standards from ACROS Organics, Geel, Belgium) to give a slope of 97.9. This solution was also then sent for 2 minute contact testing against staph aureus as in Example 66. The results showed that $Log_{10}$ reduction for the sample in two minutes was >4.25±0.00 and for the PBS buffer the result was 0.53±0.38. The original titer bacterial concentration was 8.85E+06 cfu/mL.

Example 68: Pet Chews

The pet chews examined here were Dentley's Natural Flavor Pig Ears, Prime Cuts for Medium Dogs. They are made in the USA and are distributed by Pacific Coast Distributing, Inc. in Phoenix, Ariz.

These ears were cut into pieces about 6 to 7 sq cm in size. Some of these pieces delaminated on cutting. The experiments reported below were only done on non-delaminated samples.

Each pig ear piece was first weighed and then soaked with stirring in liquid medium of choice for a specific amount of time at room temperature. The pig ear pieces were then removed from the medium, were blotted dry with a kim-wipe and were weighed so the % weight increase could be monitored.

The pieces were first evaluated for ethanol soak for various periods of time and the average weight gain was 0.1% after a soak period of one hour. We used this soak to kill any bacteria on the surface of these pieces. This was then followed by a water soak (deionized water) for various periods of time and found out that it absorbed about 43% of water in a period of 90 minutes. We also tested some pieces which were directly soaked in water (without ethanol soak) and the weight gain was within one percent of the above value. Ethanol was obtained from Pharmco-Aaper, Brookfield, Conn.

In order to treat the pig ear pieces with functionalized CuI particles, we adopted one hour soak in ethanol followed by a 90 minute soak in water comprising functionalized CuI particles. After the ethanol soak the samples were wiped dry and left for about 15 minutes at room temperature for further drying. After the water soak, the samples were wiped and dried at 85° C. for 90 minutes. The amount of CuI uptake was estimated from the concentration of the CuI in water and the calculated water uptake (43%) from the above experiments.

The CuI functionalized with PVP and NaI was used as prepared in Example 57a (CuI/PVP/NaI weight ratio was 90/9/1). When the soaking solution had 116.4 ppm of CuI, then it resulted in imparting 0.005% of CuI by weight to the pig ear. When the concentration of CuI was doubled, the calculated copper intake increased proportionately. The pig ear after it absorbed 0.005% CuI did not look different from the original pig ear. At 0.01% CuI uptake to about 0.2% uptake, the pig ear looked unchanged except that a slight green color was seen at the edges of these pieces.

Example 69: Body Cleaner (Shampoo) Include Color Change and Efficacy Results A solution of body cleaner was prepared by combining 85.5 g Steol 4N (Stepan Company, Northfield, Ill.) with 29.04 g Amphosol HCG (Stepan Company, Northfield, Ill.) and 185.46 g deionized water in a glass bottle equipped with a stir bar. The solution was stirred for one hour at room temperature to give a clear, colorless, foamy solution.

After preparing the above body cleaner, the other ingredients were added and stirred for additional three hours at room temperature. The proportion of these is shown below. Each of these formulations were prepared with had 60 ppm copper concentration. Sodium citrate tribasic hydrate, ≥99% was obtained from Sigma-Aldrich Corp., St. Louis, Mo. CuI/SDS was 75/25 in weight proportion and made as in Example 28. CuI/Silica was 88% CuI and 12% silica made as in Example 64, and CuI/PVP/NaI was in 90/9/1% in weight proportion and made as in Example 57a.

TABLE 42

| Ingredients (g) | Formulation | | |
| --- | --- | --- | --- |
|  | F1 | F2 | F3 |
| De-ionized water | 61.82 | | |
| Steol 4N | 28.5 | | |
| Amphosol HCG | 9.68 | | |
| Sodium citrate | 0.03 | 0.03 | 0.03 |
| CuI/SLS | 0.0241 | | |
| CuI/Silica | | 0.0205 | |
| CuI/PVP/NaI | | | 0.02 |

Antimicrobial testing results after 24 hours are shown below in the table below. In these tables the original titer for P. aeruginosa (ATCC#9027) was 3.43E+07 cfu/mL, and for S. aureus (ATCC#25923) 1.11E+07 cfu/mL.

TABLE 43

| Microbe | Solution Without CuI $Log_{10}$ Reduction | F1 $Log_{10}$ Reduction | F2 $Log_{10}$ Reduction | F3 $Log_{10}$ Reduction |
| --- | --- | --- | --- | --- |
| P. aeruginosa | 1.53 ± 0.09 | 5.31 ± 0.16 | 5.76 ± 0.67 | 5.58 ± 0.07 |
| S. aureus | 1.39 ± 0.05 | 3.32 ± 0.03 | 3.27 ± 0.06 | 3.35 ± 0.30 |

Example 70: Solvent Based Nail Polish

A solution of 0.05% Cu in the dried coating was prepared by mixing 0.0014 g CuI functionalized with silica powder (88% CuI and 12% by weight as prepared in Example 64) with 4 g Orly Bonder Rubberized nail polish Basecoat (orange color, available from in Orly International Inc, Los Angeles, Calif.)) in a small glass vial equipped with a stir bar. Orly bonder is a solvent based nail polish base and comprises of butyl acetate, isopropyl alcohol, heptane, ethyl acetate, trimethyl pentanyl diisobutyrate, tosylamide/epoxy resin, polyvinyl butyral, nitrocellulose, benzophenone-1, red 17, violet 2, yellow11 and upon drying at room temperature has a solid content of 20.3%. This solution was stirred at room temperature for 1 hour and was sonicated for 1 hour. It was then left to stir overnight at room temperature. The resulting solution is slightly hazy and orange in color. No precipitate is seen when sitting for several hours at room temperature. The coatings with and without the CuI/silica powder could not be distinguished by eye.

Functionalized CuI particles were made as described in Example 54(Sample A), excepting that instead of PVP a PVP-olefin copolymer Ganex® V516 was used and the grinding medium was isopropanol. The composition by weight was CuI90%/9% V516 copolymer/1% NaI. This material was also compatible with solvent based Orly Bonder Rubberized nail polish Basecoat.

Example 71: Testing of Antimicrobial Properties Against *Mycobacterium smegmatis*, *Mycobacterium fortuitum* and *Candida albicans* (Yeast)

a) Copper iodide powder was prepared as in Example 28 as 75% copper iodide and 25% sodium lauryl sulfate.

b) Copper iodide powder was prepared as in example 57a as 90% copper iodide, 9.75% polyvinylpyrrolidone, 0.25% sodium iodide.

c) Copper iodide powders as described in (a) and (b) were tested against the yeast *Candida albicans* (ATCC #10231), *Mycobacterium smegmatis* (ATCC #14468) and *M. fortuitum* (ATCC #6841) at 60 ppm Cu. $Log_{10}$ reductions in colony forming units are shown in the tables below (">" indicates no viable colony forming units). Both *M. Fortuitum* and *M. Smegmatis* were harvested after 48 hours of growth before subjecting them to the antimicrobial testing.

TABLE 44

$Log_{10}$ Reductions against *C. albicans*

| Time | PBS Control | CuI/SLS | CuI/PVP/NaI |
|---|---|---|---|
| 1 min | — | 0.11 ± 0.04 | 0.05 ± 0.03 |
| 5 min | — | 3.21 ± 0.44 | 0.51 ± 0.03 |
| 15 min | 0.02 ± 0.04 | 4.12 ± 0.00 | 2.75 ± 0.05 |
| 1 hour | −0.01 ± 0.11 | >4.12 ± 0.00 | >3.89 ± 0.34 |
| 6 hour | 0.11 ± 0.16 | >4.12 ± 0.00 | 3.74 ± 0.12 |
| 24 hour | 0.14 ± 0.08 | >4.12 ± 0.00 | >4.12 ± 0.00 |
| 48 hour | 0.30 ± 0.13 | >4.12 ± 0.00 | >4.12 ± 0.00 |

Original titer = 6.65E+5 cfu/ml

TABLE 45

$Log_{10}$ Reductions against *M. fortuitum*

| Time | PBS Control | CuI/SLS | CuI/PVP/NaI |
|---|---|---|---|
| 15 min | 0.03 ± 0.02 | 0.00 | 0.69 ± 0.03 |
| 1 hour | 0.06 ± 0.11 | 1.81 ± 0.04 | 1.76 ± 0.01 |
| 24 hour | 0.30 ± 0.30 | 4.24 ± 0.13 | 4.05 ± 0.20 |

Original titer = 1.40E+7 cfu/ml

TABLE 46

$Log_{10}$ Reductions of against *M. smegmatis*

| Time | PBS Control | CuI/SLS | CuI/PVP/NaI |
|---|---|---|---|
| 15 min | 0.03 ± 0.02 | 0.00 | 2.61 ± 0.01 |
| 1 hour | −0.14 ± 0.13 | 2.46 ± 0.54 | 4.40 ± 0.36 |
| 24 hour | 0.63 ± 0.27 | >5.35 ± 0.00 | >5.35 ± 0.00 |

Original titer = 1.12E+7 cfu/ml

These results on *M. smegmatis* and *M. fortuitum* suggest that the present functionalized particles would also be effective against *M. tuberculosis*, and even against the strains of *M. tuberculosis* which are resistant to conventional antibiotics—since the mechanism of antimicrobial activity of the present antimicrobial agents is very different from the antimicrobial mechanisms of conventional antibiotics. Similarly, the results on *C. albicans* show the potential of these materials to control yeast infections.

Example 72: Antimicrobial Efficacy of an Aqueous Acrylic Indoor Paint

The CuI/SLS powder (as prepared in Example 28 with a weight proportion of 75:25 of CuI and SLS), an antimicrobial (AM) additive was added to Harmony White Paint (Sherwin Williams (Cleveland, Ohio) Interior Acrylic Latex semi gloss "green sure designation") at a copper concentration of 0.1 wt % and at 0.25% wt. and stirred into the paint. The a* and b* color coordinates of the dry paint were measured after applying to the aluminum substrates and waiting for one week and these for the paint without and with (0.1% Cu) antimicrobial additive were −0.9, 1.3 and −4.6, 5.9 respectively. The antimicrobial properties of these coatings were measured after exposing these coatings to growth culture as described earlier for 6 hours to *P. aeruginosa*. The results ($Log_{10}$ reduction) are in the table below.

TABLE 47

| Time | Paint without AM additive | Paint with 0.1% Cu | Paint with 0.25% Cu |
|---|---|---|---|
| 6 hours | 1.05 ± 0.15 | >6.06 ± 0.00 | >6.06 ± 0.00 |

Original Titer = 5.77E+06 cfu/mL

Example 73: Preparation of Polyurethane Foam with Copper Iodide a) Preparation of Copper Iodide Dispersion for Polyurethane Incorporation: Block copolymer functionalized copper iodide was prepared as in Example 45 as 90.9% CuI and 9.1% DisperBYK-190® in the solids. Water was exchanged with 1,4-butanediol by addition of 1,4-butanediol and removal of water under reduced pressure. The resultant dispersion in 1,4-Butanediol was at 38.96% solids as measured by thermogravimetric analysis.

b) Preparation of Standard Polyurethane Foam: FlexFoam-iT!® 25 (Smooth-On, Inc. Easton, Pa.) was prepared by thoroughly mixing 1 part A (isocyanate component) and 2 parts B by weight. This was cast in a plastic dish to give an off-white foam.

c) Preparation of Antimicrobial Polyurethane Foam: 10 g of Part B of FlexFoam-iT!® 25 (from Smooth-On, Inc. Easton, Pa.) was mixed thoroughly with 0.66 g CuI/1,4-butanediol dispersion described in (a). This was then thoroughly mixed with 5 g Part A (isocyanate component). This was cast in a plastic dish to give an off-white foam that was similar to the standard foam described in (b).

Example 74: Antimicrobial Epoxy Coating

EPON SU-3 (Miller-Stephenson Chemical Company INC, Danbury, Conn.) and EPALLOY 9000 (CVC Thermoset Specialists Maple Shade, N.J.) were heated separately to 60° C. and while at temperature mixed to form a clear yellow resin. To this mixture was added the anhydride (4-Methylhexahydrophthalic anhydride obtained from Broadview Technologies INC. Newark, N.J.) and mixed well to form an opaque resin. To this mixture was added the CuI adduct and again mix well. The antimicrobial CuI functionalized particles were prepared by grinding in the following proportion—49.4% CuI, 49.5% Ganex WP-660 (polyvinylpyrrolidone with olefin or alkylated groups obtained from Ashland (New Milford, Conn.)), 1% NaI in isopropanol. After grinding, isopropanol was removed and the resulting powder was added to the resin. The CuI formulated powder dispersed very well in the epoxy medium to give a smooth free flowing resin. The curing agent (AJICURE MY-H an amine adduct obtained from AJINOMOTO CO., INC Japan) was then added and the mixture thoroughly mixed to give a red colored resin. This was degassed under vacuum at 25° C. until no bubbles were seen. The epoxy formulation was then brush coated onto cleaned aluminum substrates and pre-cured under ambient atmosphere at 85° C. for 30 minutes and complete cure at 150° C. for 45 minutes. Copper content in the final coatings was 0.1 weight % (based on 100% solids). The antimicrobial efficacy of the coatings was evaluated using JIS2801-2000 after exposing the microbial solution to the coating for a period of 24 hours. Coatings without antimicrobial additive were compared, and as shown below, the coatings with the additive were far superior in reducing the microbial population.

TABLE 48

| Log10 reduction of *P. aeruginosa* (ATCC # 9027) | | Log10 reduction of *S. aureus* (ATCC # 25923) | |
|---|---|---|---|
| Without antimicrobial additive | With antimicrobial additive | Without antimicrobial additive | With antimicrobial additive |
| −0.34 ± 0.14 | >3.61 ± 0.56 | 0.31 ± 0.04 | >4.44 ± 0.00 |

Epoxy-based coatings are routinely used to provide protection to pipes against corrosive environments and also used to coat proppants. Thus this example shows that coatings comprising these metal salts are feasible and are antimicrobially active. Since CuI particles have also been shown to be active against SRB (see Example 75), these results demonstrate the efficacy of such coatings in oil fields and specifically as coatings on proppants.

Example 75: Activity of CuI Particles Against Sulfate Reducing Bacteria (SRB)

The purpose of this experiment was to determine if copper (I) iodide particles could act as a bacteriocidal agent against *Desulfovibrio vulgaris* (ATCC 29579), an anaerobic sulfate reducing bacteria (SRB). The CuI particles were made as in Example 57a (CuI/PVP/NaI weight ratio was 90/9/1). *D. vulgaris* was cultured for 2 days prior to experiment in SRB 2 media (Intertek). From this culture, 2 ml of inoculum was added to 18 ml anaerobic phosphate buffered saline (PBS). CuI with NaI and PVP was tested at concentrations of 60 and 10 ppm copper (wt % Cu). CuI particles solutions were diluted in the inoculated PBS media to the above concentrations to produce vials with 20 ml solution. Each concentration was tested in duplicate. In addition, a positive control sample consisting of inoculated PBS without CuI was also tested. The sealed bottles were incubated at room temperature (23° C.) without agitation.

An initial sample was taken from the positive control to establish a starting concentration of bacteria for the experiment. 0.5 ml samples were taken at 1 hour time point and diluted in 4.5 ml anaerobic Dey/Engely (D/E) neutralizing broth to neutralize the Cu bacteriocide. A 1:10 dilution series was made using anaerobic PBS. Bacterial numbers were quantified by a 3-tube most probable number (MPN) method. Three tubes of anaerobic modified Baar's media (10 ml each) per dilution were inoculated with 1 ml each from their respective diluted sample. These tubes were incubated at 37° C. for 72 hours. Positive samples were evaluated based on the presence of iron sulfide (FeS), which forms a black precipitate as a byproduct of hydrogen sulfide produced by bacterial growth reacting with iron included in the modified Baar's media.

All test media (PBS, D/E and modified Baar's media) were pretreated with 100 µl Oxyrase oxygen scavengers (obtained from Oxyrase Inc, Mansfield, Ohio) to render the test media anaerobic. In addition, 100 µl of 3% cysteine were added to each bottle of modified Baar's media to further reduce oxygen contamination.

The starting concentration of the microbe in the experiment was $2.4 \times 10^4$ mpn/ml. At one hour time point the $\log_{10}$ reduction (mpn/ml) using 60 ppm Cu (as CuI) was greater than 3.90, for 10 ppm Cu it was greater than 3.84 and for control it showed no reduction.

In another experiment the starting concentration of the microbe was $2 \times 10^7$ mpn/ml and series of dilutions were made with the lowest at $10^3$ mpn/ml, and also SRB2 media was used instead of Barr's media. These results compared with functionalized particles of CuI (same as above, i.e., with PVP and NaI) to a solution of $CuCl_2$ ($Cu^{++}$) and also with gluteraldehyde solution—a material commonly used as a biocide in petroleum industry. The copper concentration in the first two formulations was 10 ppm, and the gluteraldehyde concentration in the solution was 10 ppm. The results after one hour of contact time showed that the $\log_{10}$ reduction for CuI was greater than 5.4, for gluteraldehyde this was greater than 4.23 and for $CuCl_2$ it was not effective at any of the dilutions which were evaluated, and the only inference that could be made was that this reduction if any, must be less than 3.

In summary, this application discloses proppants for use in oil & gas wells (petroleum extraction) having a polymeric coating containing within the said coating particles of an antimicrobial material. Geometrically such coated proppant particles look like a core-shell configuration where core is the proppant and the shell is the coating. These coatings release an antimicrobially active agent into the environment of the coated proppant when such proppants are deployed in the field. Preferably, the polymeric coating comprises at least one thermosetting polymer. Some examples of useful polymer constituents include epoxy, phenolic, silicone, urethane, polyester and alkyd. The coating formulation may comprise one or more polymers or their precursor monomers which react to form the desired polymers. The coating formulation containing the antimicrobial material is applied on the proppant and then the coating is dried by removal of a solvent and/or cured.

The antimicrobial material used is one which is released from the coating or which releases antimicrobially active constituents from the coatings when such proppants are deployed in the field. A preferred antimicrobial material is a low water solubility material which is preferably added as preformed particles in a size of 1,000 nm or smaller, more preferably less than 300 nm. It is preferred that such particles are surface modified to make them compatible with the polymer used in the coating material and to provide other advantages of functionalized particles discussed above. The molecular weight of the surface modifiers is at least 60. The antimicrobial agents may be metal compounds, such as compounds of oligodynamic metals preferably of copper and zinc. Some of the preferred compounds are Copper(I) iodide; Copper(I) chloride; Copper(I) bromide; Copper(I) acetate; Copper(I) sulfide; and Copper(I) thiocyanate, copper oxide and zinc pyrithione.

In addition, the foregoing disclosure provides coating formulations (or compositions) which comprises at least one of polymer and a polymer precursor (monomer) along with an antimicrobial compound which can be used to coat proppants. The antimicrobial compounds are preferably metal compounds of low water solubility. These are incorporated in the composition as preformed particles which are surface modified (functionalized). The preferred metals in the metal compounds are oligodynamic metals, and some of the preferred compounds are silver halide, Copper(I) iodide; Copper(I) chloride; Copper(I) bromide; Copper(I) acetate; Copper(I) sulfide; and Copper(I) thiocyanate, copper oxide and zinc pyrithione. The antimicrobial material used is one which is released from the coating or which releases an antimicrobially active constituent from the coatings into the environment of the coated proppant when such proppants are deployed in the field.

Further, this disclosure teaches a proppant having antimicrobial characteristics which is coated with a polymeric coating containing an antimicrobial compound. The coated proppant provides antimicrobial activity by release of an active agent when the said proppant contacts a microbial environment. The antimicrobial agents may also be incorporated in porous particles which are then added to the coating formulations. Preferred antimicrobial agents have low water solubility and are added as preformed particles into the coating. Less preferred, the particles of the antimicrobial agents (or domains of antimicrobially rich phase as compared to the surrounding matrix) may also be formed during the drying or curing of the coating due to phase separation. The antimicrobial agents may be soluble in the coating formulation but phase separate upon curing and/or drying.

This invention also discloses the use of masterbatches (or concentrates/intermediates) which contain copper iodide. Preferably copper iodide is added to these masterbatches in one of two ways (a) as particles in a size less than 1,000 nm containing at least 51% by weight of CuI where preferably the surfaces of these particles are modified by materials with a molecular weight of at least 60 and (b) in the pores of non-zeolytic porous particles. One may also form masterbatches of other cuprous salts such as cuprous oxide, cuprous thiocyanate, CuBr and CuCl by adding surface functionalized particles of these materials in a size less than about 1,000 nm or incorporating these salts in the pores of non-zeolytic porous particles. These masterbatches have a high concentration of copper iodide or copper salts relative to the end-product. Use of masterbatches to add cuprous iodide (or other cuprous salts) to articles of manufacture can impart antimicrobial characteristics to the finished articles of manufacture. The articles of manufacture may be thermoplastics or thermosets, where in the latter the masterbatch material is mixed with a monomeric formulation which is then polymerized and may also be crosslinked to form a thermosetting material. During use the antimicrobial properties of the articles of manufacture are mainly imparted by release of cuprous ions.

The concentration of cuprous iodide in the article of manufacture (end-product) is less than that in the masterbatch. The concentration of copper (from copper iodide or other copper salts) in typical masterbatch compositions is less than about 15% by weight. These masterbatches may be formed in a desired polymer matrix, and may be made as pellets or as powders. The masterbatch or concentrates may also be add to coating formulations (including liquid formulations) so as to deposit antimicrobial coatings on other articles.

Typically the concentration of CuI in the finished article is about 10 times lower than in the masterbatch. That is, the finished articles of manufacture have a copper content of less than about 10% of the master batch. Typically the concentration of copper as CuI or a cuprous salt in the finished product is less than about 1%. Antimicrobial agents also impart antiodor properties to the articles that these are present in by killing the microbes which are typically responsible for the odors. Fibers incorporating the antimicrobial agents can be made by forming fibers by mixing masterbatch with the appropriate polymers. Textiles containing such fibers would have antimicrobial and/or antiodor properties.

The masterbatch or the articles of manufacture may comprise antioxidant additives which protect cuprous ions from oxidation as cuprous ions have superior antimicrobial properties. Preferred antioxidant additives are selected from (a) organic acids and mineral acids; (b) salts and esters of organic acids; and (c) alcohols, aldehydes and polyols.

It will be understood that various modifications may be made to the embodiments disclosed herein. Hence the above description should not be construed as limiting, but merely as exemplifications of preferred embodiments. Those skilled in the art will envision other modifications that come within the scope and spirit of the claims appended hereto. All patent applications cited as priority (related applications) are explicitly incorporated herein by reference in their entirety.

The invention claimed is:

1. A method of producing an antimicrobial article of manufacture comprising:
   providing a masterbatch composition comprising:
   one or more cuprous salts in a concentration of 1 to 15% of copper by weight,
      wherein said cuprous salts are at least one of (a) particles containing the said cuprous salts, whose surfaces are modified by at least one functionalizing agent and (b) non-zeolitic porous particles containing the said cuprous salts; and
   incorporating the masterbatch composition in the article of manufacture and thereby providing antimicrobial properties to the article of manufacture by release of copper ions from the said article.

2. The method of claim 1, wherein said cuprous salt is cuprous thiocyanate, CuI, CuBr, CuCl, or a combination thereof.

3. The method of claim 1, wherein the masterbatch composition additionally comprises an antioxidant.

4. A textile having anti-odor properties, wherein said textile comprises the masterbatch composition made by the method of claim 1 incorporated therein.

5. A method of producing an antimicrobial article of manufacture comprising:
   providing a composition containing cuprous iodide and an alkali metal iodide,
   providing an article of manufacture, and
   incorporating said composition into said article of manufacture, wherein (i) the ratio of I:Cu is in the range of about 1 to about 1.5, and (ii) antimicrobial properties are provided to the article of manufacture by release of copper ions from the said article, thereby producing said antimicrobial article of manufacture.

6. A method of producing an antimicrobial article of manufacture comprising:

providing a composition containing cuprous iodide with no alkali metal iodide, providing an article of manufacture, and incorporating said composition into said article of manufacture, wherein (i) the ratio of I:Cu is in the range of about 1 to about 1.5, and (ii) antimicrobial properties are provided to the article of manufacture by release of copper ions from the said article, thereby producing said antimicrobial article of manufacture.

\* \* \* \* \*